(12) United States Patent
Hermsmeier et al.

(10) Patent No.: US 6,649,606 B1
(45) Date of Patent: Nov. 18, 2003

(54) TETRAHYDROISOQUINOLINE ANALOGS AS MODULATORS OF CHEMOKINE RECEPTOR ACTIVITY

(75) Inventors: Mark Alden Hermsmeier, Somerville, NJ (US); David B. Rawlins, Morrisville, PA (US); John Wityak, Robbinsville, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 10/289,671

(22) Filed: Nov. 7, 2002

Related U.S. Application Data

(60) Provisional application No. 60/346,377, filed on Nov. 9, 2001.

(51) Int. Cl.[7] ............... C07D 209/02; C07D 217/00; A61K 31/47; A61K 31/305
(52) U.S. Cl. ............... 514/217.01; 514/307; 514/412; 540/594; 546/139; 548/492
(58) Field of Search ............... 514/217.01, 307, 514/421; 540/594; 546/139; 548/492

(56) References Cited

U.S. PATENT DOCUMENTS

| | | |
|---|---|---|
| 5,206,235 A | 4/1993 | Fisher et al. |
| 5,283,241 A | 2/1994 | Bochis et al. |
| 5,284,841 A | 2/1994 | Chu et al. |
| 5,310,737 A | 5/1994 | Fisher et al. |
| 5,317,017 A | 5/1994 | Ok et al. |
| 5,374,721 A | 12/1994 | Schoen et al. |
| 5,430,144 A | 7/1995 | Schoen et al. |
| 5,434,261 A | 7/1995 | Schoen et al. |
| 5,438,136 A | 8/1995 | Devita et al. |
| 5,536,716 A | 7/1996 | Chen et al. |
| 5,545,735 A | 8/1996 | Bochis et al. |
| 5,578,593 A | 11/1996 | Chen et al. |
| 5,583,130 A | 12/1996 | Bochis et al. |
| 5,606,054 A | 2/1997 | Fisher et al. |
| 5,622,973 A | 4/1997 | Morriello et al. |
| 5,652,235 A | 7/1997 | Chen et al. |
| 5,663,171 A | 9/1997 | Chen et al. |
| 5,672,596 A | 9/1997 | Wyratt et al. |
| 5,726,307 A | 3/1998 | Schoen et al. |
| 5,811,402 A | 9/1998 | Klimkowski et al. |

FOREIGN PATENT DOCUMENTS

| | | |
|---|---|---|
| EP | 330 469 | 8/1989 |
| EP | 421 436 | 4/1990 |
| EP | 1113007 | 7/2001 |
| JP | 4099722 | 3/1992 |
| WO | WO93/02679 | 2/1993 |
| WO | WO93/20099 | 10/1993 |
| WO | WO94/19367 | 1/1994 |
| WO | WO95/16675 | 2/1995 |
| WO | WO95/13069 | 5/1995 |
| WO | WO96/22997 | 1/1996 |
| WO | WO96/05195 | 2/1996 |
| WO | WO96/22997 | 8/1996 |
| WO | WO97/24369 | 7/1997 |
| WO | WO98/18763 | 5/1998 |
| WO | WO95/58948 | 12/1998 |
| WO | WO98/58948 | 12/1998 |
| WO | WO00/10975 | 3/2000 |
| WO | WO00/010975 | 3/2000 |
| WO | WO00/24398 | 5/2000 |
| WO | WO00/54729 | 9/2000 |
| WO | WO01/13917 | 3/2001 |

OTHER PUBLICATIONS

Ornstein et al., "6–substituted Decahydroisoquinoline–3–carboxylic Acids as Potent and Selective Conformationally Constrained NMDA Receptor Antagonists", J. Med. Chem., (1992), 35, pp. 3547–3560.

Weisbach et al. "Synthesis and Pharmacology of Some alpha–Oxy–and alpha–Hydroxy–a–enzyltetrahydroisoquinolines", (1968) vol. II, pp. 752–760.

Anderson et al., Synthesis and Murine Antineoplastic Activity of Bis[(carbamoyloxy)methyl] Derivative of Pyrrolo[2, 1–a]isoquinoline, J. Med. chem., (1984) 27, pp. 1321–1325.

*Primary Examiner*—Zinna Northington Davis
(74) *Attorney, Agent, or Firm*—Laurelee A. Duncan

(57) ABSTRACT

Tetrahydroisoquinoline analogs are provided which are modulators of chemokine receptor activity.

The tetrahdroisoquinoline analogs thereof have the structure

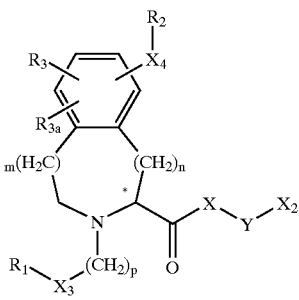

wherein $R_1$, $R_2$, $R_3$, $R_{3a}$, $X_1$, $X_2$, $X_3$, $X_4$, m, n and p are as described herein.

12 Claims, No Drawings

TETRAHYDROISOQUINOLINE ANALOGS AS MODULATORS OF CHEMOKINE RECEPTOR ACTIVITY

This application claims priority from U.S. provisional application Ser. No. 60/346,377 filed Nov. 9, 2001.

FIELD OF THE INVENTION

The present invention relates to tetrahydroisoquinoline analogs which are chemokine receptor modulators, and to methods for treating inflammatory diseases such as asthma, constrictive obstructive pulmonary disease (COPD), inflammatory bowel syndrome, allergic diseases, psoriasis, and arthritis.

BACKGROUND OF THE INVENTION

Chemokines are chemotactic cytokines that are released by a variety of cell types to attract and activate other cell types such as macrophages, T and B lymphocytes, basophils, neutrophils, mast cells, and eosinophils. They are broadly classified as C, CC, CXC, or $CX_3C$ chemokines dependent upon their amino acid sequence. For example, in CC chemokines the first two cysteines in the sequence are adjacent, while in CXC chemokines these cysteines are separated by one or more amino acid residues.

Chemokines bind to specific cell-surface receptors that belong to the family of G protein coupled seven transmembrane domain proteins. Upon ligand binding, chemokine receptors transduce an intracellular signal through the associated trimeric G proteins, resulting in calcium flux, changes in cell morphology, upregulated expression of cellular adhesion molecules, degranulation, and promotion of cell migration.

Chemokine receptors are implicated as key mediators of inflammatory, infectious, and immunoregulatory disorders and diseases, including asthma, COPD, and allergic diseases; rheumatoid arthritis, atherosclerosis, and psoriasis; solid organ transplant rejection, osteoarthritis, and inflammatory bowel syndrome. To illustrate, the CCR3 receptor appears to be a key mediator in attracting eosinophils and Th2 polarized CD4+ T cells to sites of inflammation in the lung, and also plays an important role in activating these cells. The ligands that bind CCR3 can induce a rapid increase in the intracellular calcium ion concentration (calcium flux), degranulation, increased expression of cell adhesion molecules, and cell migration. Agents that could modulate activity of the CCR3 receptor would have utility in the treatment of disorders and diseases in which eosinophils or Th2 CD4+ T cells appear to play a prominent role. A similar utility has been demonstrated using antibodies specific for the murine CCR3 chemokine receptor. Such antibodies can be used to deplete eosinophils in in vivo inflammatory models in mice.

Several mammalian viruses such as, but not limited to, cytomegaloviruses, herpesviruses, and poxviruses have been shown to express proteins with the binding properties of chemokine receptors in infected cells. In addition, several chemokine receptors have been demonstrated to act as cellular receptors for a variety of viruses, as well as some bacteria, and parasites. Thus, agents which modulate chemokine receptor activity may also have utility in infectious diseases. Examples would include, but not be limited to, blocking of HIV infection of CCR3, CCR5, or CXCR4 expressing cells; or in the prevention of manipulation of the immune response by viruses such as cytomegaloviruses that use a chemokine receptor for cellular infection.

SUMMARY OF THE INVENTION

In accordance with the present invention tetrahydroisoquinoline analogs are provided which are chemokine receptor modulators (especially modulators of CCR3) and have the structure

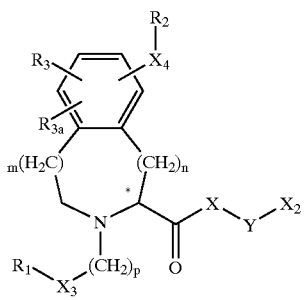

I wherein $R_1$ is alkyl, aryl, alkenyl, alkynyl, arylalkyl, arylalkenyl, cycloalkyl, arylcycloalkyl cycloalkylalkyl, cycloalkyl-alkoxy, alkoxyalkyl, alkylthioalkyl, aryloxyalkyl, arylalkoxyalkyl, cycloheteroalkyl, cycloheteroalkylalkyl, heteroaryl, or heteroarylalkyl, and where these groups may be optionally substituted with 1 to 3 J1 groups which may be the same or different and the $R_1$ aryls may be further optionally substituted with 1 to 5 halogens, aryl, $-CF_3$, $-OCF_3$, 1–3 hydroxyls, 2 of which substituents where possible, may be joined by a methylene bridge;

$R_2$ is H, alkyl, aryl, alkenyl, alkynyl, arylalkyl, arylalkenyl, cycloalkyl, cycloalkylalkyl, alkoxyalkyl, aryloxyalkyl, arylalkoxyalkyl, cycloheteroalkyl, cycloheteroalkylalkyl, cycloalkylalkoxy, heteroaryl, or heteroarylalkyl, and where these groups may be optionally substituted with a J1a group and the aryls may be further optionally substituted with 1 to 5 halogens, $-CF_3$, $-OCF_3$, or 1–3 hydroxyls;

X is a bond, $-O-$, or $-NR_4-$;

$R_3$ and $R_{3a}$ are the same or different and are independently selected from H, alkoxy, halogen, $-CF_3$, alkyl, or aryl;

$R_4$, $R_{4a}$, $R_{4b}$, $R_{4c}$, $R_{4d}$, $R_{4e}$, $R_{4f}$, $R_{4g}$, $R_{4h}$, $R_{4i}$, $R_{4j}$, $R_{4k}$, and $R_{4l}$ are the same or different and are independently selected from H, $C_1$-$C_6$alkyl, or aryl;

m, n and p are the same or different and are independently 0 or 1;

Y is a bond,

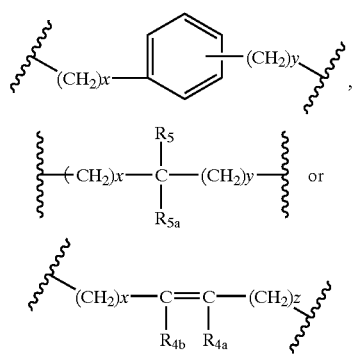

where x and y are the same or different and are independently 0 to 3 and z is 1 to 3;

$R_5$ and $R_{5a}$ are the same or different and are independently H, alkyl, alkoxy, hydroxyl, halogen, $-CF_3$, aryl, alkaryl, and cycloalkyl; or $R_5$ and $R_{5a}$ can be independently joined to one or both of $R_6$ and $R_7$ groups (see $X_2$) to form an alkylene bridge of 1 to 5 carbon atoms; or $R_5$ and $R_{5a}$ can be joined together to form a ring of from 4–7 carbon atoms;

$X_2$ is aryl optionally substituted with 1 to 3 J1 groups which may be the same or different, cycloheteroalkyl optionally substituted with 1 to 3 J1 groups which may be the same or different, pyridinyl optionally substituted with 1 to 3 J1 groups which may be the same or different,

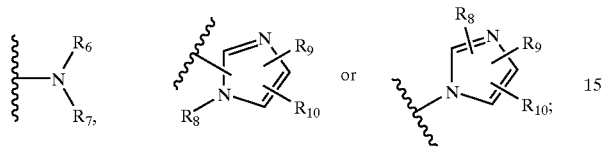

$R_6$ and $R_7$ are the same or different and are independently H or alkyl where the alkyl may be optionally substituted with halogen, 1 to 3 hydroxys, 1 to 3 $C_1$–$C_{10}$alkanoyloxy, 1 to 3 $C_1$–$C_6$ alkoxy, phenyl, phenoxy, or $C_{1-6}$alkoxycarbonyl; or $R_6$ and $R_7$ can together form —$(CH_2)_tX_5(CH_2)_u$— where $X_5$ is —$C(R_{4c})(R_{4d})$—, —$C(R_{4c})(NT_1T_{1a})$—, —O— or —$N(R_{4e})$—, t and u are the same or different and are independently 0 to 4;

$R_8$ is H, $C_1$–$C_6$alkyl, —$CF_3$, alkaryl, or aryl, and with the alkyl and aryl groups being optionally substituted with 1 to 3 hydroxys, 1 to 3 $C_1$–$C_{10}$alkanoyloxy, 1 to 3 $C_1$–$C_6$ alkoxy, phenyl, phenoxy or $C_1$–$C_6$alkoxycarbonyl;

$R_9$ and $R_{10}$ are the same or different and are independently H, $C_1$–$C_6$alkyl, —$CF_3$, alkaryl, aryl, or halogen, and with the alkyl and aryl groups being optionally substituted with 1 to 3 hydroxys, 1 to 3 $C_1$–$C_{10}$ alkanoyloxy, 1 to 3 $C_{1-6}$ alkoxy, phenyl, phenoxy or $C_1$–$C_6$ alkoxycarbonyl;

$X_3$ is a bond, —C(O)—, —C(O)O—, —C(O)N($R_{4f}$)—, —S(O)$_2$—, or —S(O)$_2$N($R_{4f}$)—;

$X_4$ is a bond, —O—, —OC(O)—, —N($R_{4g}$)—, —N($R_{4g}$)C(O)—, —N($R_{4g}$)C(O)N($R_{4h}$)—, —N($R_{4g}$)S(O)$_2$—, —N($R_{4g}$)S(O)$_2$N($R_{4h}$), —OC(O)N($R_{4g}$)—, —C(O)—, —C(O)N($R_{4g}$)—, —S—, —S(O)$_2$—, or —S(O)$_2$N($R_{4g}$)—;

J1 and J1a are the same or different and are independently nitro, halogen, hydroxyl, —$OCF_1$, —$CF_3$, alkyl, aryl, —$(CH_2)_vCN$, —$(CH_2)_vN(T_{1a})C(O)T_1$, —$(CH_2)_vN(T_{1a})C(O)OT_1$, —$(CH_2)_vN(T_{1a})C(O)N(T_{1a})T_1$, —$(CH_2)_vNT_1T_{1a}$ —$(CH_2)_vN(T_{1a})SO_2T_1$, —$(CH_2)_vC(O)N(T_{1a})T_1$, —$(CH_2)_vC(O)OT_1$, —$(CH_2)_vOC(O)OT_1$, —$(CH_2)_vOC(O)T_1$, —$(CH_2)_vOC(O)OT_1$, —$(CH_2)_vOC(O)T_1$, —$(CH_2)_vOC(O)N(T_{1a})T_1$, —$(CH_2)_vN(T_{1a})SO_2N(T_{1b})T_1$, —$(CH_2)_vOT_1$, —$(CH_2)_vSO_2T_1$, —$(CH_2)_vSO_2N(T_{1a})T_1$, —$(CH_2)_vC(O)T_1$, —$(CH_2)_vCH(OH)T_1$, or heteroaryl as defined below, with v being 0–3;

$T_1$, $T_{1a}$ and $T_{1b}$ are the same or different and are independently H, alkyl, alkenyl, alkynyl, lower alkythioalkyl, alkoxyalkyl, aryl, arylalkyl, heteroaryl, heteroarylalkyl, cycloheteroalkyl, or cycloalkyl, each of which may be optionally substituted with halogen, hydroxyl, —C(O)NR$_{4i}$R$_{4j}$, —NR$_{4i}$C(O)R$_{4j}$, —CN, —N(R$_{4i}$)SO$_2$R$_{11}$, —OC(O)R$_{4i}$, —SO$_2$ NR$_{4i}$R$_{4j}$, —SOR$_{11}$, —SO$_2$R$_{11}$, alkoxy, —COOH, cycloheteroalkyl, or —C(O)OR$_{11}$; with the proviso that $T_1$ cannot be hydrogen when it is connected to sulfur, as in SO$_2T_1$; or $T_1$ and $T_{1a}$ or $T_1$ and $T_{1b}$ can together form —$(CH_2)_r$ $X_{5a}(CH_2)_s$— where $X_{5a}$ is —C(R$_{4k}$)(R$_{4l}$)—, —C(R$_{4k}$)(NT$_1$T$_{1a}$)—, —O— or —N(R$_{4k}$)—, r and s are the same or different and are independently 0 to 4;

$R_{11}$ is $C_1$–$C_6$alkyl or aryl;

or a pharmaceutically acceptable salt thereof, or a prodrug ester thereof, and including all stereoisomers thereof;

(1) with the proviso that where m is 0 and n is 1, the moiety —$X_4$—$R_2$ is other than alkyl or alkoxy and (2) where X is a bond and $X_2$ is amino, then m is 1.

Thus, the compounds of formula I of the invention include compounds of the following structures.

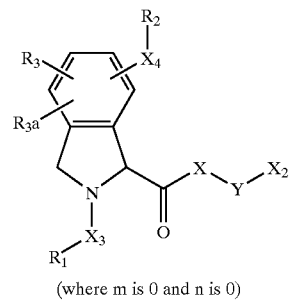

(where m is 0 and n is 0)

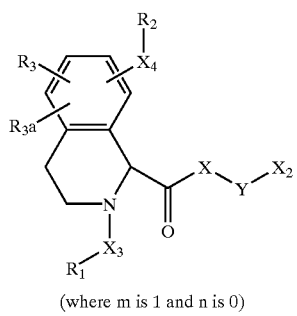

(where m is 1 and n is 0)

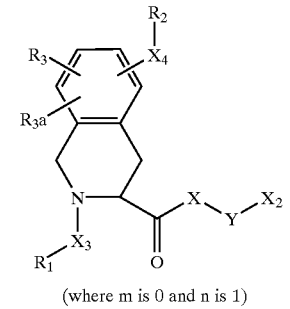

(where m is 0 and n is 1)

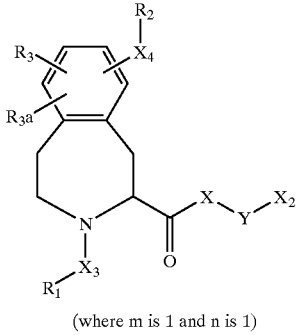

(where m is 1 and n is 1)

The compounds of the instant invention all have at least one asymmetric center as noted by the asterisk in structural formula I. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. The racemic mixtures may be separated into individual optical isomers employing conventional procedures such as by chromatography or fractional crystallization. In the case of the asymmetric center represented by the asterisk in formula I, it has been found that compounds with either the R or S configuration are of almost equal activity. Therefore one isomer might be only slightly preferred, therefore both are claimed.

The pharmaceutically acceptable salts of the compounds of formula I of the invention include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, and salts of naturally occurring amino acids such as arginine, lysine, alanine and the like, and prodrug esters thereof.

In addition, in accordance with the present invention, a method for increasing levels of endogenous growth hormone or increasing the endogenous production or release of growth hormone is provided wherein a compound of formula I as defined hereinbefore is administered in a therapeutically effective amount.

Furthermore, in accordance with the present invention, a method is provided for preventing or treating osteoporosis (improving bone density and/or strength), or treating obesity, or increasing muscle mass and/or muscle strength, or maintenance of muscle strength and function in elderly humans, or reversal or prevention of fraility in elderly humans, wherein a compound of formula I as defined hereinbefore is administered in a therapeutically effective amount.

DETAILED DESCRIPTION OF THE INVENTION

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 6 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 3 substituents including alkyl, aryl, alkenyl, alkynyl, hydroxy, arylalkyl, cycloalkyl, cycloalkylalkyl, alkoxy, arylalkyloxy, alkanoyl, amino, haloaryl, $CF_3$, $OCF_3$, aryloxy, heteroaryl, cycloalkyl-alkoxyalkyl, or cycloheteroalkyl.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl, cyclododecyl, cyclohexenyl,

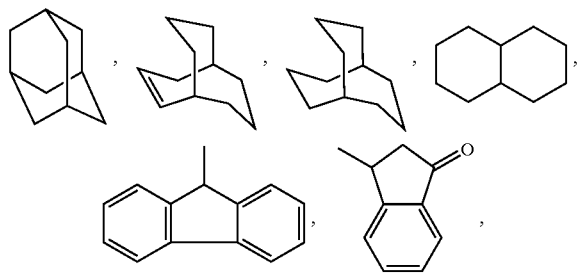

any of which groups may be optionally substituted with 1 to 3 substituents as defined above for alkyl.

The term "aryl" as employed herein alone or as part of another group refers to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or cycloheteroalkyl rings) and may be optionally substituted through available carbon atoms with 1 to 5 halo, 1, 2, or 3 groups selected from hydrogen, haloalkyl, alkyl, haloalkyl, alkoxy, haloalkoxy, alkenyl, trifluoromethyl, trifluoromethoxy, alkynyl, cycloalkylalkyl, fluorenyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or preferably any of the aryl substituents as set out above.

Preferred aryl groups include phenyl, biphenyl or naphthyl.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxyl", "alkoxyl", "aryloxyl" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl, aryl, arylalkyl, heteroaryl, heteroarylalkyl, cycloheteroalkyl, cycloheteroalkylalkyl and/or cycloalkyl.

The term "lower alkylthio", "alkylthio", "alkylthioalkyl", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include alkanoyl, alkenoyl, aroyl, aralkanoyl, heteroaroyl, cycloalkanoyl, and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 2 to 6 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio or any of the substituents for alkyl as set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normalchain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the substituents for alkyl as set out herein.

The term "alkylene" as employed herein alone or as part of another group refers to alkyl groups as defined above having single bonds for attachment to other groups at two different carbon atoms and may optionally be substituted as defined above for "alkyl".

The terms "alkenylene" and "alkynylene" as employed herein alone or as part of another group refer to alkenyl groups as defined above and alkynyl groups as defined above, respectively, having single bonds for attachment at two different carbon atoms.

Examples of $(CH_2)_m$, $(CH_2)_n$, $(CH_2)_p$, $(CH_2)_r$, $(CH_2)_s$, $(CH_2)_t$, $(CH_2)_u$, $(CH_2)_v$, $(CH_2)_x$, $(CH_2)_y$, $(CH_2)_z$, and other groups (which may include alkylene, alkenylene or alkynylene groups as defined herein, and may optionally include 1, 2, or 3 substituents which may be any of the substituents for alkyl set out herein), are as follows:

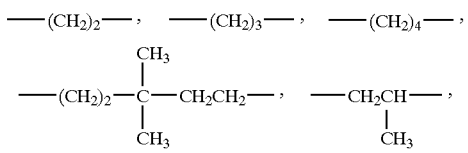

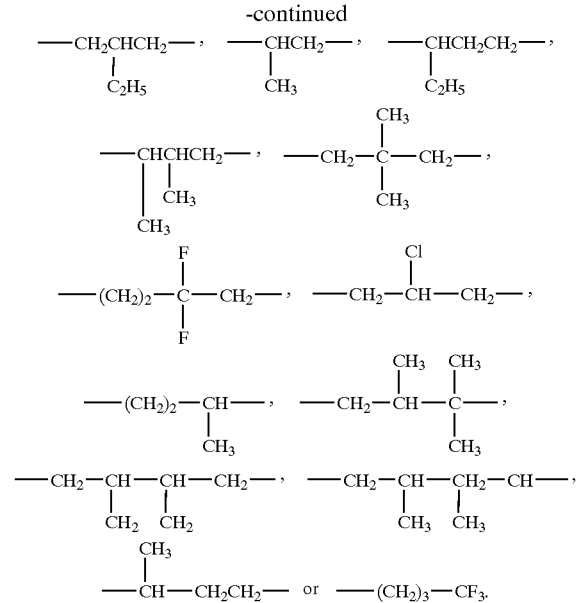

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "heterocyclic", "heterocyclo" or "heterocycle" as employed herein alone or as part of another group refers to "heteroaryl" groups or "cycloheteroalkyl" groups.

The term "cycloheteroalkyl" as used herein alone or as part of another group refers to a 4-, 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

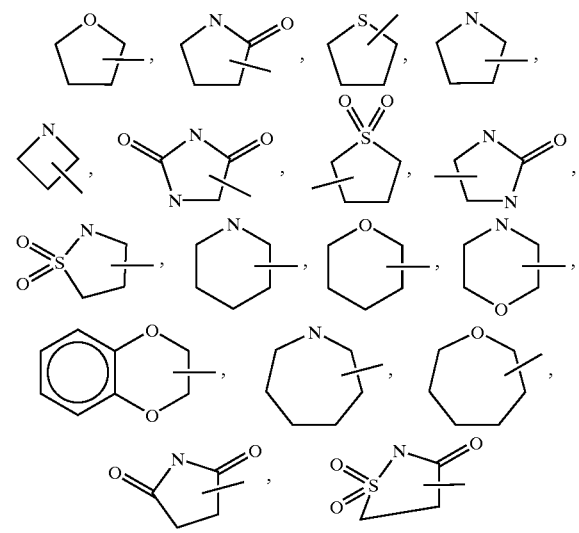

and the like. The above groups may include 1 to 4 substituents such as alkyl, halo, oxo and/or any of of the aryl substituents set out herein. In addition, any of the above rings can be fused to a cycloalkyl, aryl, heteroaryl or cycloheteroalkyl ring.

The term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides, such as

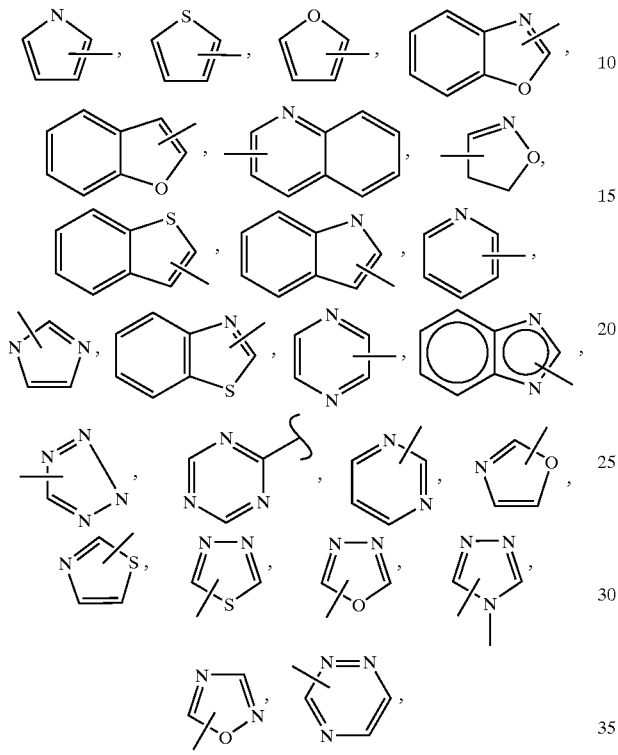

and the like.

The heteroaryl groups may optionally include 1 to 4 substituents such as any of the aryl substituents set out herein as well as carbonyl and arylcarbonyl. In addition, any of the above rings can be fused to a cycloalkyl, aryl, heteroaryl or cycloheteroalkyl ring.

Preferred are compounds of formula IB wherein $R_1$ is alkyl, aryl, arylalkyl, cycloalkyl, cycloalkylalkyl, alkoxyalkyl, aryloxyalkyl, heteroaryl, or heteroarylalkyl, and where these groups may be further optionally substituted with a J1 group;

$R_2$ is, alkyl, aryl, arylalkyl, alkoxyalkyl, aryloxyalkyl, heteroaryl, cycloalkyl, cycloalkylalkyl, or heteroarylalkyl, and these groups may be further optionally substituted by J1a;

X is —O— or —N—$R_4$;

$R_3$ and $R_{3a}$ are the same or different and are independently H, alkoxy, halogen, —CF3;

$R_4$ is H or $C_1$–$C_6$ alkyl;

m and n are independently 0 or 1;

Y is

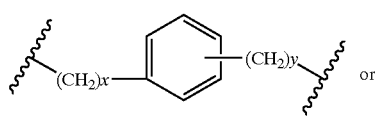 or

-continued

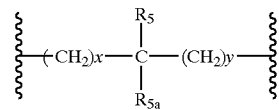

where x and y are independently 0 to 3;

$R_5$ and $R_{5a}$ are the same or different and are independently H, alkyl, —$CF_3$, or $R_5$ and $R_{5a}$ can be independently joined to one or both of $R_6$ and $R_7$ groups (see $X_2$) to form an alkylene bridge of 1 to 5 carbon atoms;

$X_2$ is

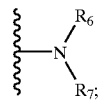

$R_6$ and $R_7$ are the same or different and are independently H or alkyl, where alkyl can optionally be substituted with halogen, 1 or 2 hydroxyls, 1 or 2 $C_1$–$C_{10}$ alkanoyloxy, 1 or 2 $C_1$–$C_6$ alkoxy, phenyl, phenoxy, $C_1$–$C_6$ alkoxycarbonyl; or $R_6$ and $R_7$ can together form —$(CH_2)_tX_5(CH_2)_u$— where $X_5$ is $C(R_4)(R_{4a})$ or O, t and u are independently 1–3;

$X_3$ is —C(O)—, —C(O)O—, or —S(O)$_2$N($R_4$)

$X_4$ is a bond, —O—, —OC(O)—, or —N($R_4$)C(O)—;

J1 is —$(CH_2)_v$CN, —$(CH_2)_v$N($T_{1a}$)C(O)$T_1$, —$(CH_2)_v$N($T_{1a}$)C(O)O$T_1$, —$(CH_2)_v$N($T_{1a}$)C(O)N($T_{1b}$)$T_1$, —$(CH_2)_v$SO$_2T_1$, —$(CH_2)_v$N($T_{1a}$)SO$_2T_1$, —$(CH_2)_v$C(O)$_v$N($T_{1a}$) $T_1$, —$(CH_2)_v$C(O)O$T_1$, —$(CH_2)_v$OC(O)$T_1$, —$(CH_2)_v$OC(O)N($T_{1a}$)$T_1$, —$(CH_2)_v$N($T_{1a}$)SO$_2$N($T_{1b}$)$T_1$, —$(CH_2)_v$O$T_1$, —$(CH_2)_v$SO$_2$N($T_{1a}$)$T_1$, —$(CH_2)_v$C(O)$T_1$, or heteroaryl, with v being 0–2;

J1a is halogen, —$(CH_2)_v$CN, —$(CH_2)_v$N($T_{1a}$)C(O)$T_1$, —$(CH_2)_v$C(O)N($T_{1a}$)$T_1$, —$(CH_2)_v$C(O)O$T_1$, —$(CH_2)_v$O$T_1$, or —$(CH_2)_v$C(O)$T_1$, with v being 0–2;

$T_1$, $T_{1a}$ and $T_{1b}$ are the same or different and are independently H, alkyl, aryl, alkaryl, or cycloalkyl; each optionally substituted with halogen, hydroxyl or alkoxy; with the proviso that $T_1$ cannot be hydrogen when it is connected to sulfur as in SO$_2T_1$;

Most preferred are compounds of the formula IB, wherein $R_1$ is alkyl, aryl, arylakyl, cycloalkyl, and cycloalkylalkyl and where these groups may be further optionally substituted with a J1 group;

$R_2$ is alkyl, aryl, arylalkyl, or cycloalkyl, and these groups may be further optionally substituted by J1a;

X is —NH or —NCH$_3$;

$R_3$ and $R_{3a}$ are each H;

m is 1;

n is 0;

Y is

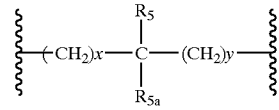

where x and y are independently 0 or 1, with the proviso that both cannot be 0;

$R_5$ and $R_{5a}$ are the same or different and are independently H, alkyl, —$CF_3$; or $R_5$ and $R_{5a}$ can be independently joined to one or both of $R_6$ and $R_7$ groups (see $X_2$) to form an alkylene bridge of 1 to 5 carbon atoms;

X₂ is

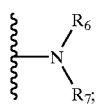

R₆ and R₇ are the same or different and are independently H or alkyl where alkyl may be optionally substituted with halogen, or 1 to 2 hydroxyls;

X₃ is —C(O)—, —C(O)O—, or —S(O)₂N(R₄ƒ);

X₄ is —O—, or —OC(O)—;

J1 is —(CH₂)vCN, —(CH₂)vN(T₁ₐ)C(O)T₁, —(CH₂)ᵥN (T₁ₐ)C(O)OT₁, —(CH₂)ᵥN(T₁ₐ)C(O)N(T₁ᵦ)T₁, —(CH₂)ᵥSO₂T₁, —(CH₂)ᵥN(T₁ₐ)SO₂T₁, —(CH₂)ᵥC(O)N(T₁ₐ)T₁, —(CH₂)ᵥC(O)OT₁, —(CH₂)ᵥOC(O)T₁, —(CH₂)ᵥOC(O)N(T₁ₐ)T₁, —(CH₂)ᵥN(T₁ₐ)SO₂N(T₁ᵦ)T₁, —(CH₂)ᵥOT₁, —(CH₂)ᵥSO₂N(T₁ₐ)T₁, —(CH₂)ᵥC(O)T₁, or heteroaryl, with v being 0–2;

J1a is halogen, —(CH₂)ᵥCN, —(CH₂)ᵥN(T₁ₐ)C(O)T₁, —(CH₂)ᵥC(O)N(T₁ₐ)T₁, —(CH₂)ᵥC(O)OT₁, —(CH₂)ᵥOT₁, or —(CH₂)ᵥC(O)T₁, with v being 0–2;

T₁, T₁ₐ and T₁ᵦ are the same or different and are independently H, alkyl, aryl or alkaryl, each optionally substituted with halogen, hydroxyl or alkoxy; with the proviso that T₁ cannot be hydrogen when it is connected to carbonyl or sulfur, as in C(O)T₁ or SO₂T₁;

Examples of preferred compounds of the invention include the following:

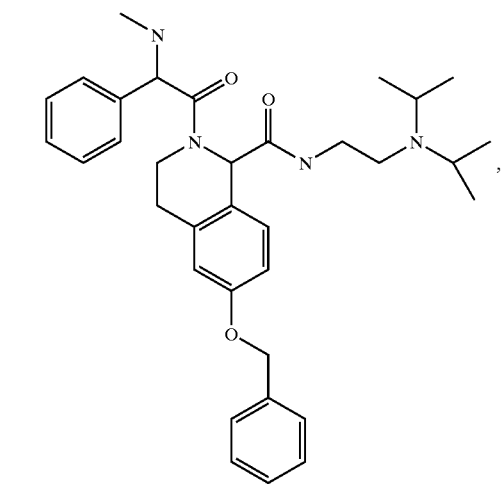

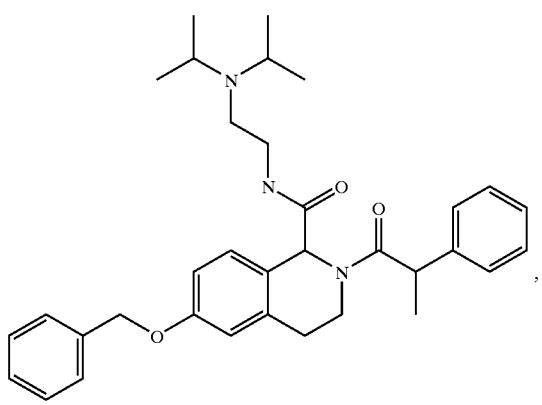

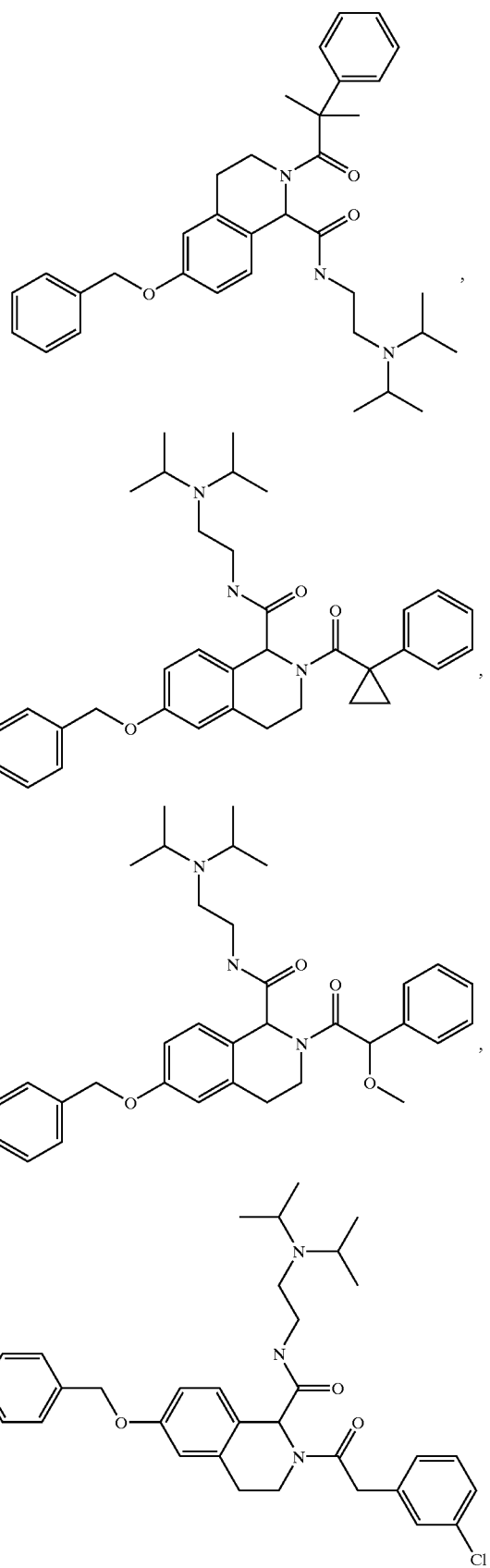

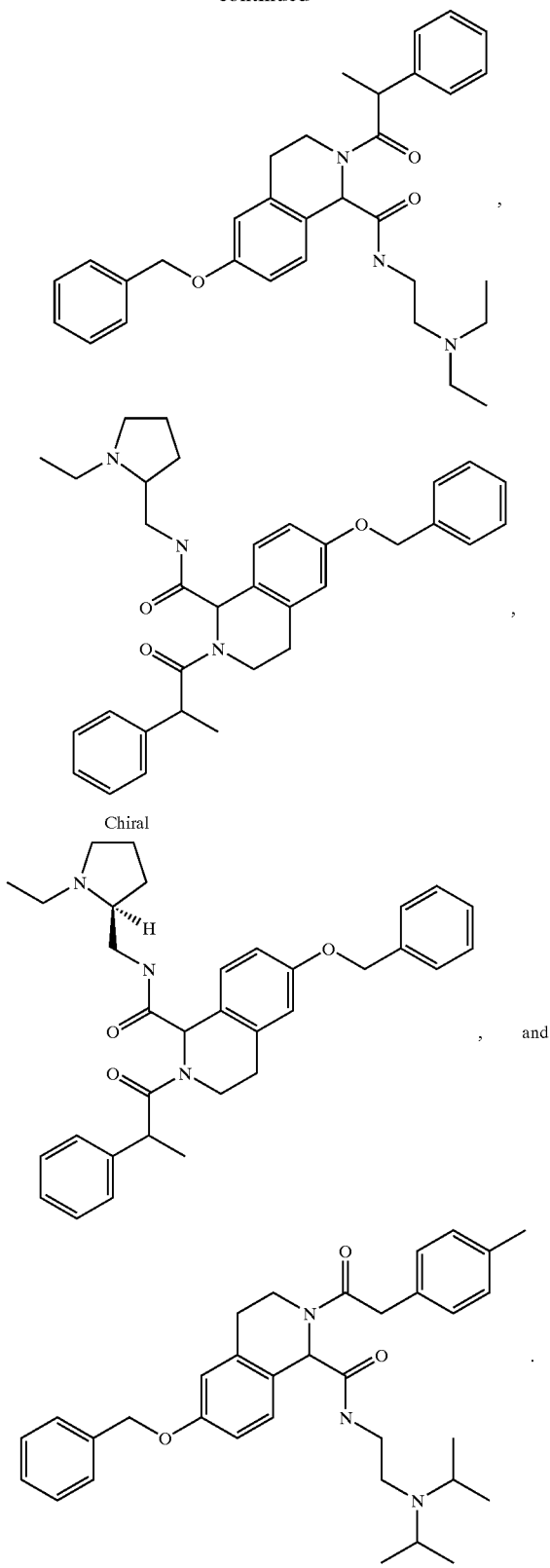

, , and

GENERAL SYNTHETIC SCHEMES

The compounds of the present invention may be prepared according to the following general synthetic schemes, as well as relevant published literature procedures that are used by one skilled in the art. Exemplary reagents and procedures for these reactions appear hereinafter and in the working Examples. Unless otherwise specified, the various substituents of the compounds are defined in the same manner as the formula I compound of the invention.

With respect to the following reaction schemes, amide bond forming reactions are conducted under standard peptide coupling procedures know in the art. Optimally, the reaction is conducted in a solvent such as DMF at 0° C. to room temperature using EDAC (WSC) (1-ethyl-3-(dimethyl-aminopropyl)carbodiimide), HOBt(1-hydroxybenzotriazole) or HOAt (1-hydroxy-7-aza-benzotriazole) and a base (Hunigs base). Carbamates of formula IE can be formed under standard conditions known in the art from chloroformates, the piperidine amine and a base.

Tetrahydroisoquinolines can be formed as shown in Scheme 1. Suitable cyclization procedures are described in J. Med. Chem., 87, 1821–1825 (1984), Tet. Lett, 21, 4819 (1980), Synthesis, 824 (1987). Alternative examples are shown in Scheme 8 (J. Org. Chem., 61, 8103–8112 (1996); Tetrahedron, 43, 5095 (1987)), Scheme 9 (Syn. Com. 23, 473–486 (1993); J Chem. Soc., Perkin Trans 1, 2497 (1996); Tet. Lett., 37, 5329 (1996)), and Scheme 10 (Tetrahedron, 50, 6193 (1994); Tet. Lett., 34, 5747–5750 (1993); J Chem Soc, Chem Commun, 11, 966 (1993)) and Scheme 11. The intermediate A in Scheme 8 can be prepared by suitable methods known in the art, such as in Tet. Lett, 37, 5453 (1996) and Synthesis, 824 (1987). The protecting group Pc in Scheme 8 can be chiral (formamidine activation Meyers, A. I., J. Org. Chem., 61, 8103–8112 (1990)), imparting chirality to compounds 48–50. The synthesis outlined in Scheme 10 can also lead to chiral induction in intermediates 66–71. Intermediates 49, 50, 61, 71 and 78 in Schemes 8 to 11 can be further transformed by methods disclosed in Schemes 1–7.

Protection and deprotection in the Schemes below may be carried out by procedures generally known in the art. See, for example, T. W. Greene, Protecting Groups in Organic Synthesis, Second Edition, 1991. P in the Schemes below denotes a nitrogen protecting group, optimally BOC or Cbz. The BOC group can be removed under acidic conditions, optimally HCl or trifluoroacetic acid. The Cbz group can be removed via hydrogenolysis, optimally using a palladium catalyst and hydrogen, or using TMSI. P1 in the Schemes below denotes a phenol protecting group such as BOC (removed by acid or base hydrolysis) or benzyl (removed by hydrogenolysis or TMSI).

Phenol intermediates shown in the General Schemes below may be acylated by methods known in the art to prepare esters and carbamates. The same phenol intermediates may be transformed into anilines by methods known in the art, such as Rossi, J Org Chem, 37 (1972). The anilines may be acylated by methods known in the art to prepare amides, ureas, and other derivatives covered by X4. The same phenol intermediates can be transformed to acids, esters or amides through an activated intermediate, such as triflate, by methods known in the art; phenol to acid: Jutand J Chem Soc., 23, 1729–1730 (1992), Wang Tet. Lett., 37, 6661–6664 (1996); to esters: Fretz Tet. Lett., 37, 8475–8478 (1996), Horikawa Heterocycles, 40, 1009–1014 (1995) ; to amides: Cacchi Tet. Lett., 27, 3931 (1986); to sulfides: Arould Tet. Lett., 37, 4523–4524 (1996), Percec J Org Chem, 60, 6895–6903 (1995), Meier Angew Chem, 106, 493–495 (1994), Wong J Med Chem, 27, 20 (1984). The resulting sulfides can be oxidized to sulfones and sulfoxides by standard methods known in the art, such as meta-chloroperoxybenzoic acid.

The arylation reaction covered in Scheme 2 can be performed under the coupling conditions in the literature described in Evans et al, *Tet Lett*, 39, 2937–2940 (1998).

Please note that in the following Schemes 1–10 the compounds of formula IB (m=1 and n=0) are shown. However, the schemes are also applicable in preparing all compounds of the formula I invention including compounds of formulae IA, IC and ID of the invention employing reagents or starting materials analogous to those shown in the schemes as will be apparent to one skilled in the art. In the following schemes $R_2$ is other than hydrogen.

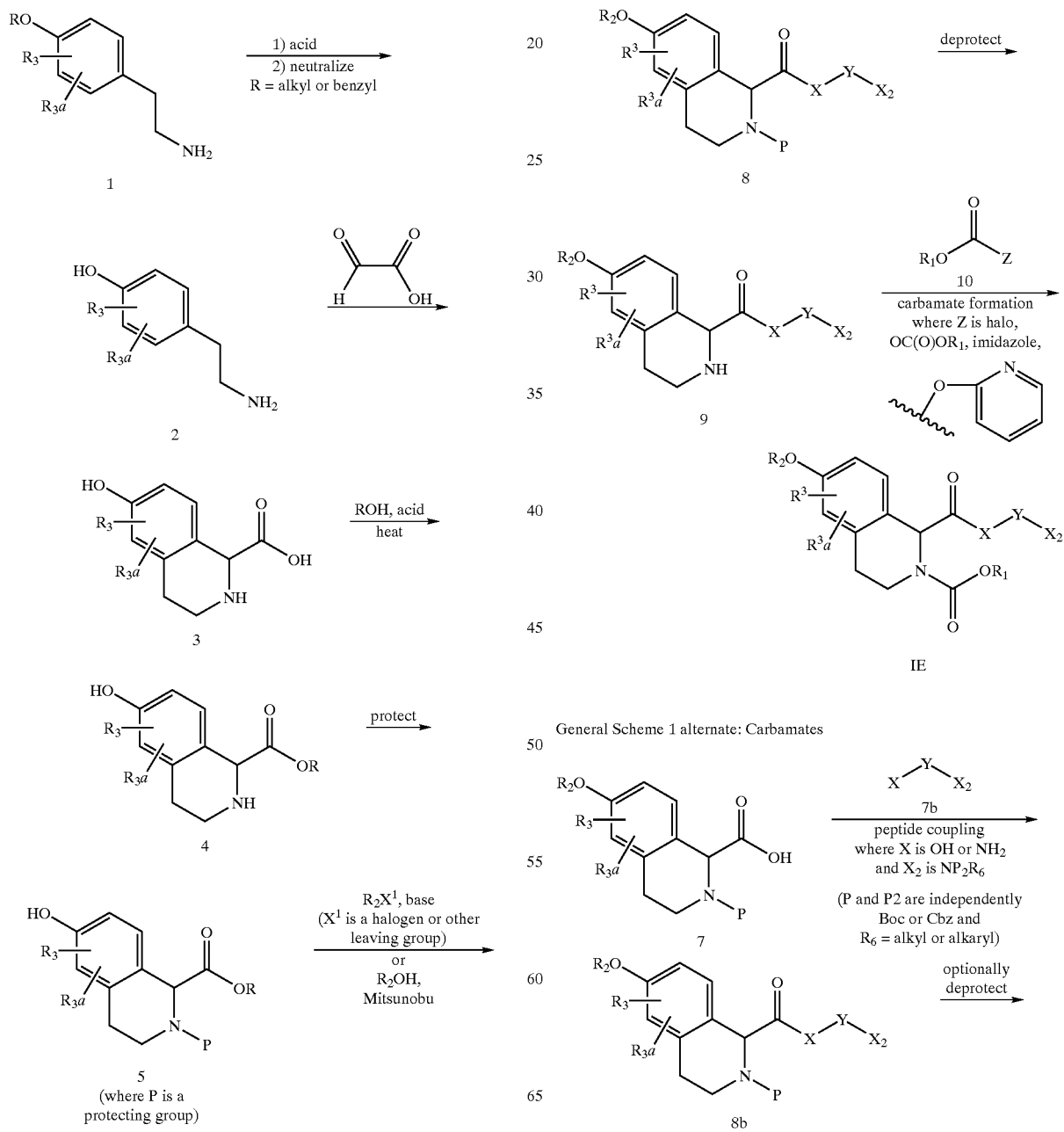

17
-continued
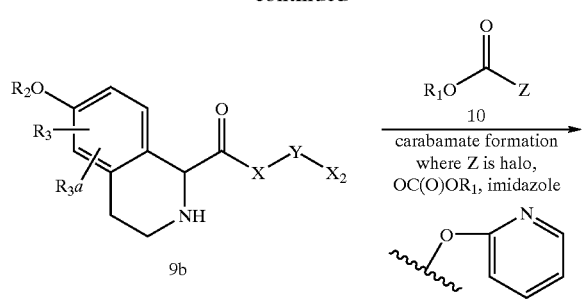
9b
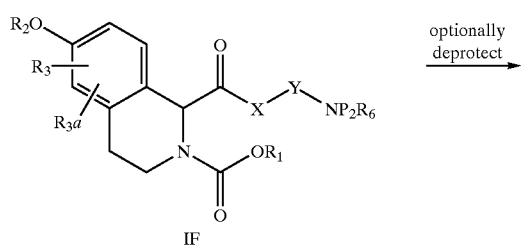
IF
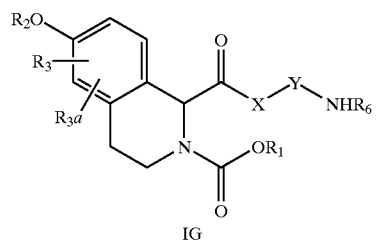
IG
IG $\xrightarrow[\text{or } R_7\text{CHO,}]{R_7X, \text{ base}}$ IE
reductive amination
General Scheme 1a: Ureas
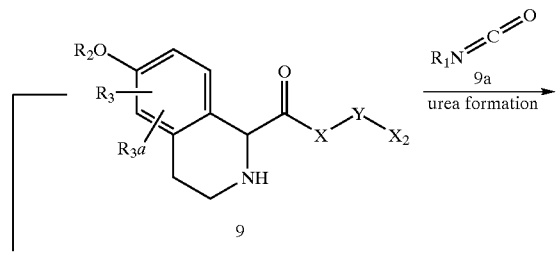
9
18
-continued
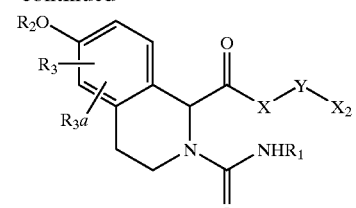
IH
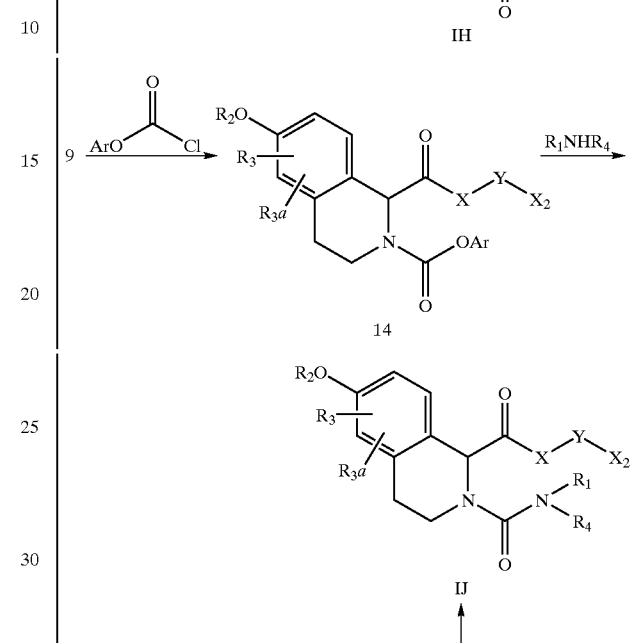
14
IJ
General Scheme 1b: Amides
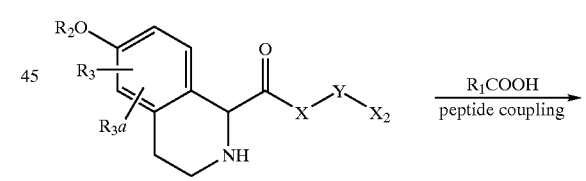
9
9 $\xrightarrow[\text{base}]{R_1C(O)Cl}$ IK
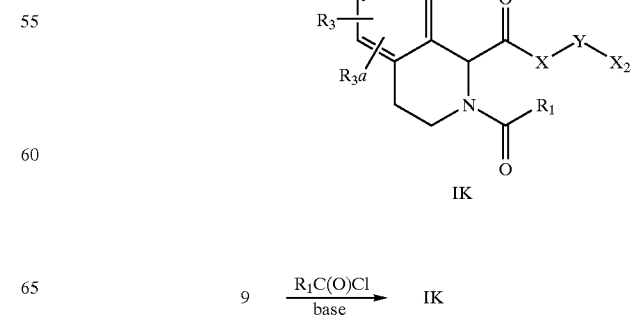
IK General Scheme 1c: SulfonylUreas
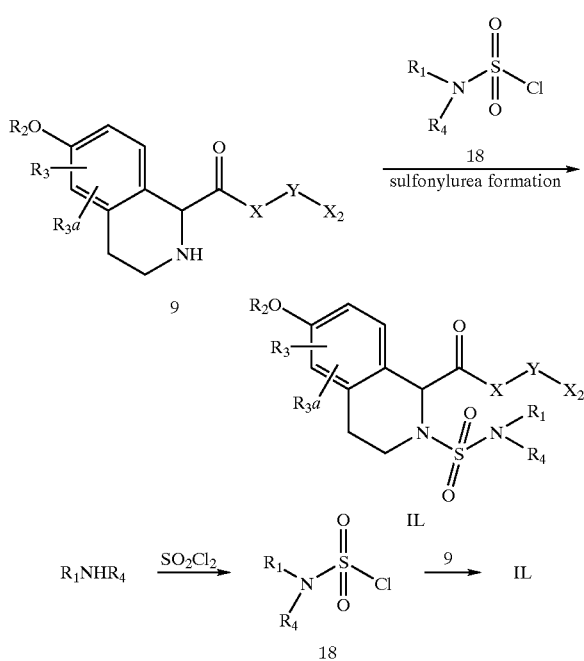
General Scheme 1d: Sulfonylamides
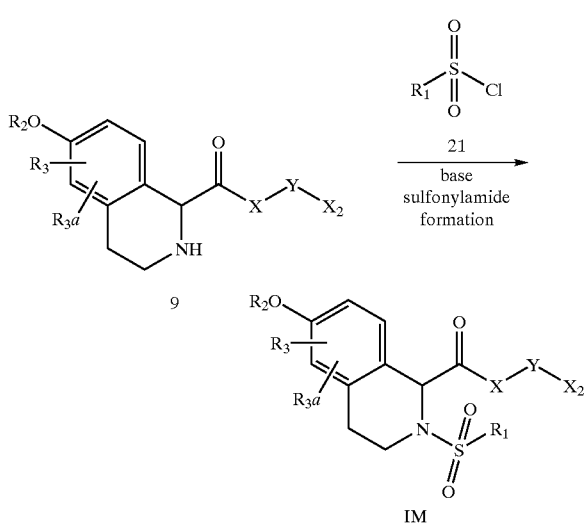
General Scheme 1e: Amines
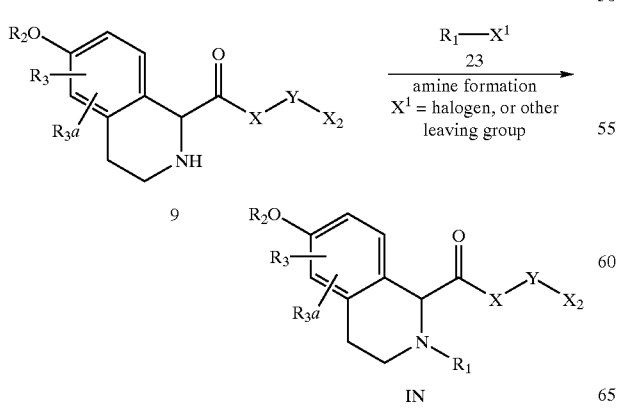
General Scheme 1f
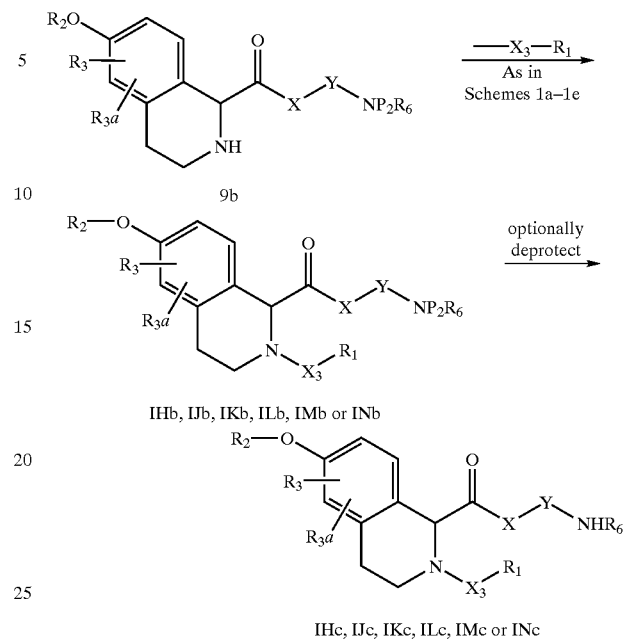
General Scheme 2: Arylation: Where $R_2$ is Phenyl
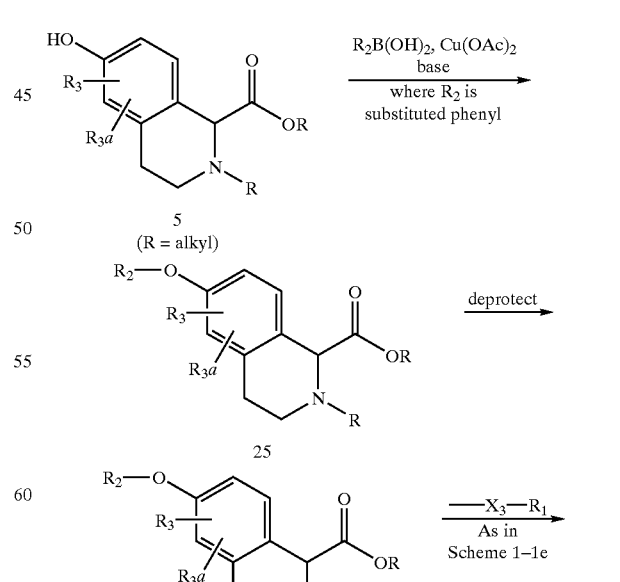

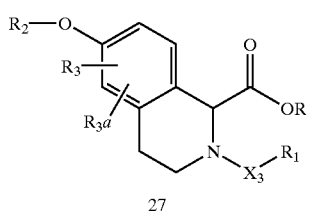

27 hydrolysis →

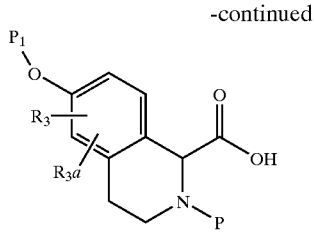

32

$X-Y-X_2$
7a or 7b
peptide coupling
where X is OH or NH$_2$
and X$_2$ is not NH$_2$
→

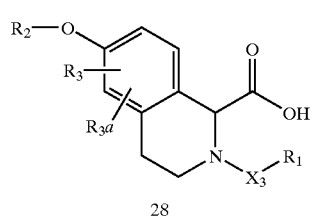

28

$X-Y-X_2$
7a or 7b
peptide coupling
where X is OH or NH$_2$
and X$_2$ is not NH$_2$
→

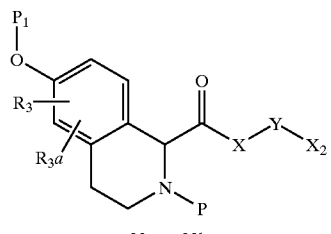

33a or 33b optionally deprotect →

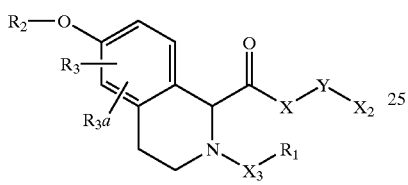

IO (X$_2$ is not NH$_2$)
IP (X$_2$ = NP$_2$R$_6$)

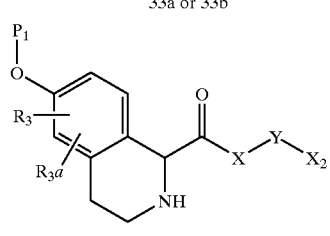

34a or 34b

—X$_3$—R$_1$
As in Schemes 1–1e

IP where X$_2$ is NP$_2$R$_6$ — deprotect →

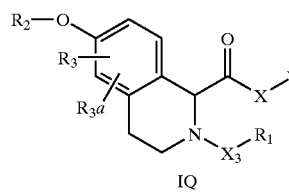

IQ

R$_7$X$^1$, base or R$_7$CHO, reductive amination → IO

General Scheme 3

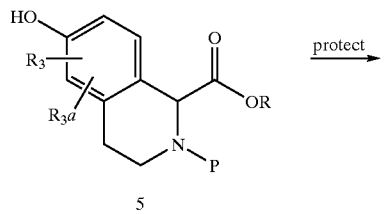

5 protect →

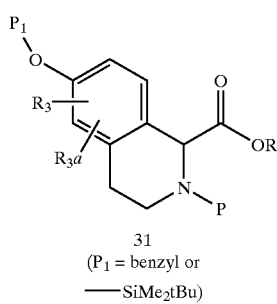

31
(P$_1$ = benzyl or —SiMe$_2$tBu)

hydrolysis →

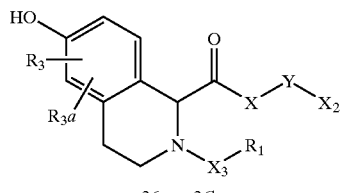

35a or 35b optionally deprotect →

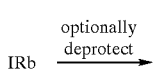

36a or 36b

R$_2$X, base
R$_2$OH, Mitsunobu
or
R$_2$B(OH)$_2$, Cu(OAc)$_2$, base
→

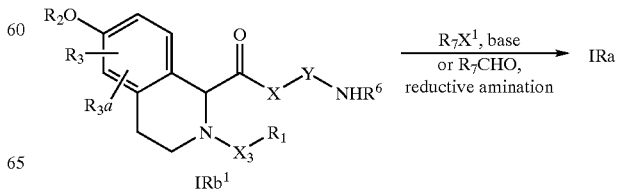

IRa or IRb
(X$_2$ ≠ NH$_2$)   (X$_2$ = NP$_2$R$_6$)

IRb — optionally deprotect →

IRb$^1$

R$_7$X$^1$, base or R$_7$CHO, reductive amination → IRa

General Scheme 4: Alternate to 9 or 9b
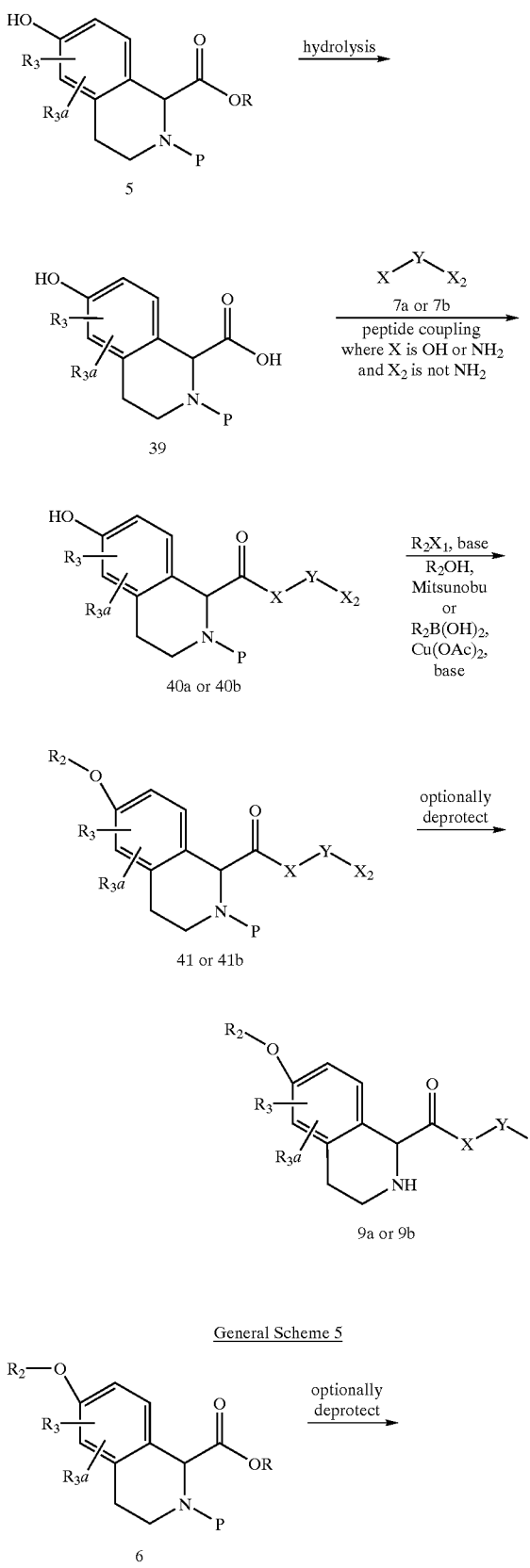
General Scheme 5
General Scheme 6: Intermediate 39
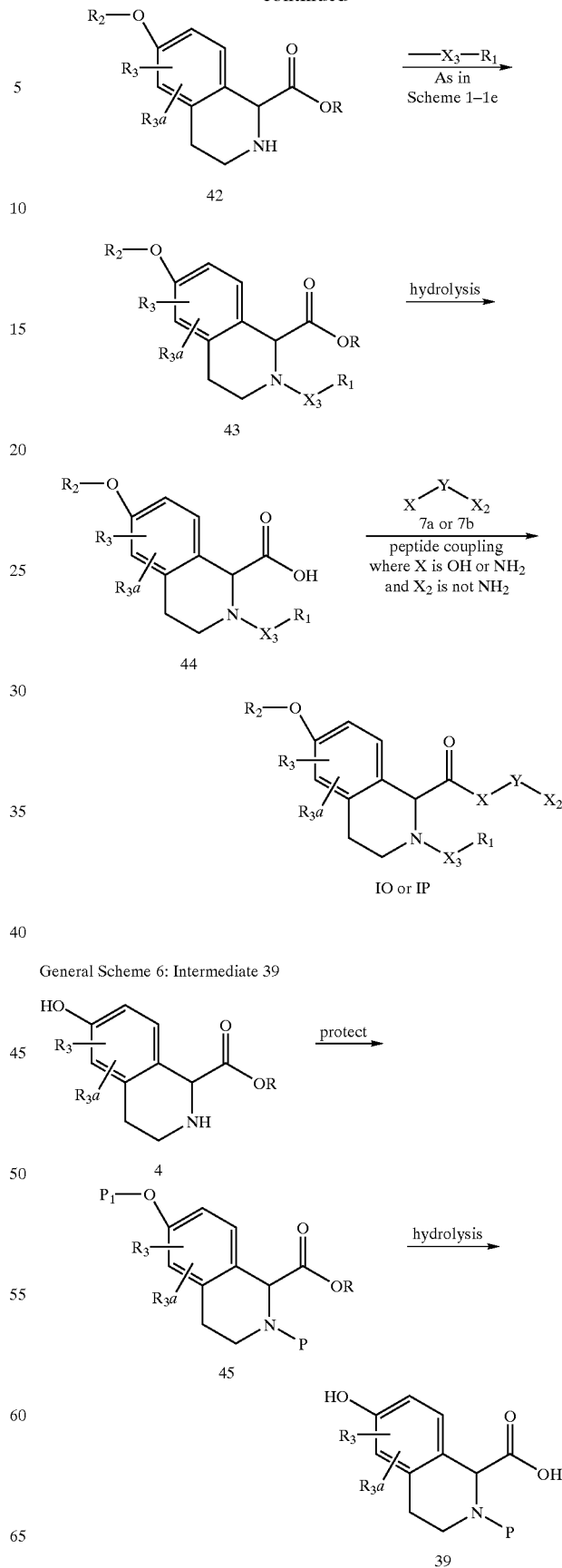

General Scheme 7
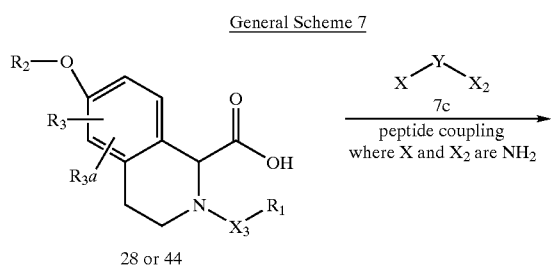
28 or 44
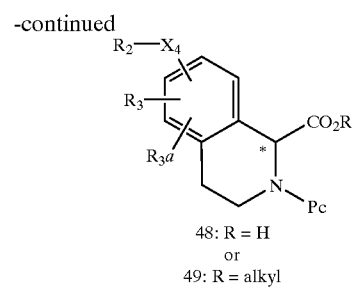
48: R = H
or
49: R = alkyl
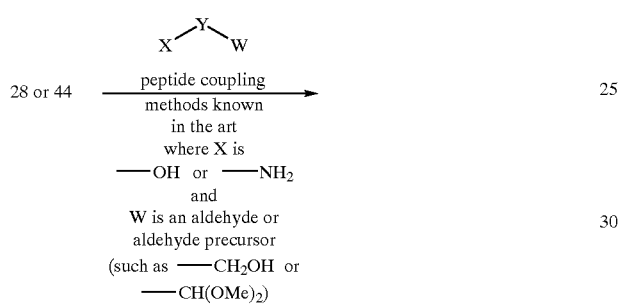
46
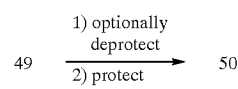
49
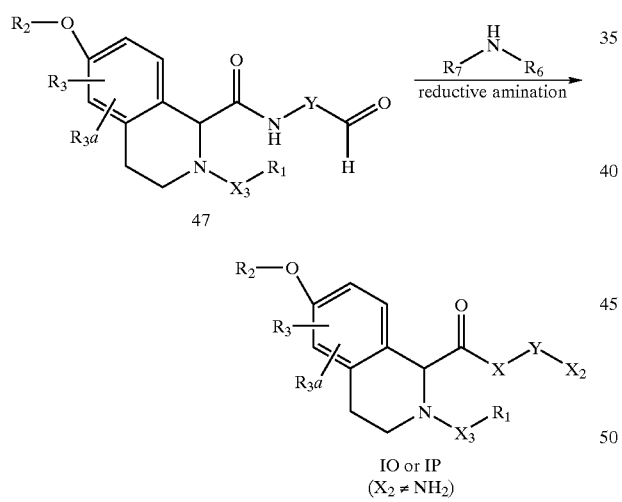
47
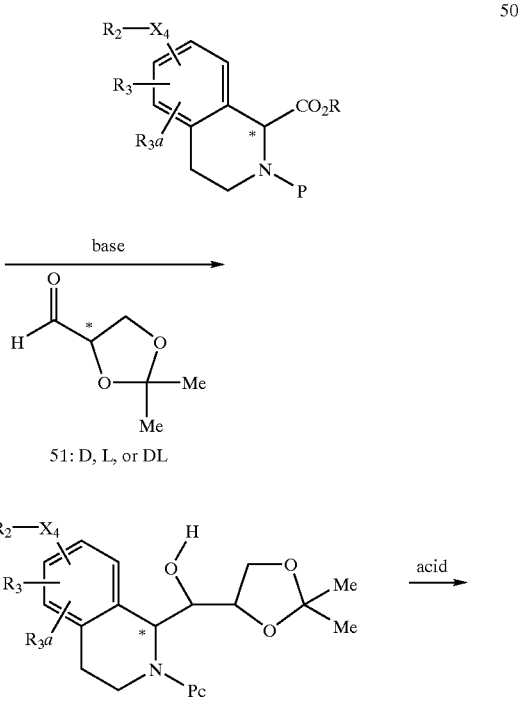
51: D, L, or DL
52
53
General Scheme 8: Alternate Routes to Core
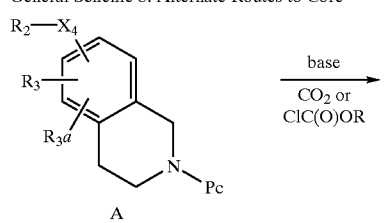
A
(Pc is protecting group such as Boc or a chiral imine)
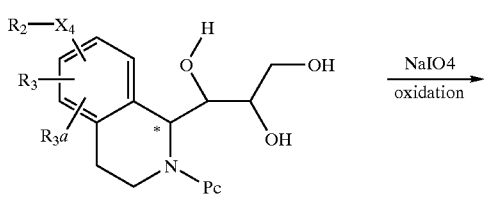

-continued

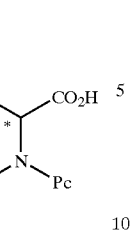

49

General Scheme 9: Alternate Routes to Core

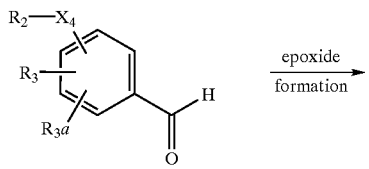

54

$\xrightarrow{\text{epoxide formation}}$

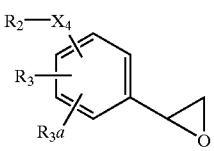

55

$\xrightarrow{\text{P}_1\text{OH, base}}$

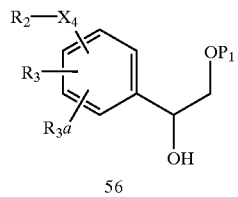

56

$\xrightarrow{\text{oxidation}}$

[Structure 57]

$\xrightarrow[\text{reductive amination, where R is alkyl}]{\begin{array}{c}\text{OR}\\|\\\text{OR}\\|\\\text{NH}_2\end{array}}$

57

[Structure 58]

$\xrightarrow{\begin{array}{c}\text{1) acid}\\\text{2) reduction}\end{array}}$

58

[Structure 59]

$\xrightarrow{\begin{array}{c}\text{optionally}\\\text{protect and}\\\text{deprotect}\end{array}}$

59

-continued

[Structure 60]

$\xrightarrow{\text{oxidation}}$

60

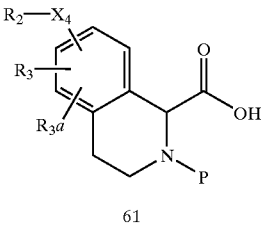

61

General Scheme 10: Alternate Routes to Core

[Structure 62 with Br, Me]

$\xrightarrow[\text{Tet., 50, 6193 (1994)}]{\text{3 steps}}$

62

[Structure 63 with Br, NH$_2$]

$\xrightarrow{\text{protect}}$

63

[Structure 64 with Br, NHP$_2$]

$\xrightarrow[\text{2) oxidation}]{\begin{array}{c}\text{1) base} \quad \text{[aldehyde with dioxolane, Me, Me]}\\\\\text{51: D, L, or DL}\end{array}}$

64

[Structure 66]

$\xrightarrow{\begin{array}{c}\text{1) optionally deprotect}\\\text{2) reductive amination}\\\text{3) protection}\end{array}}$

66

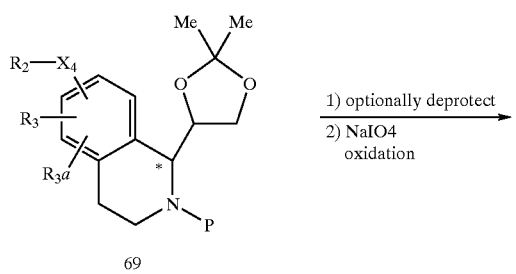
69
1) optionally deprotect
2) NaIO4 oxidation
→
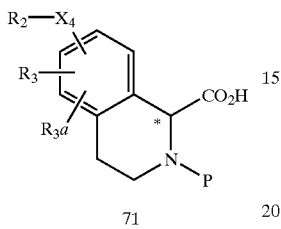
71
Alternatively:
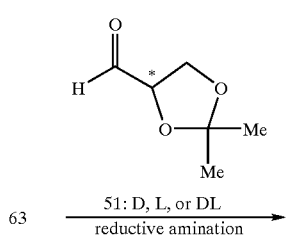
63
51: D, L, or DL
reductive amination
→
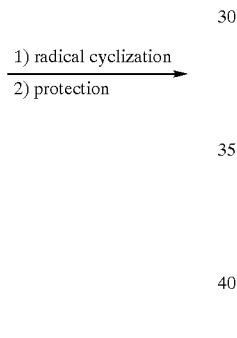
72
1) radical cyclization
2) protection
→
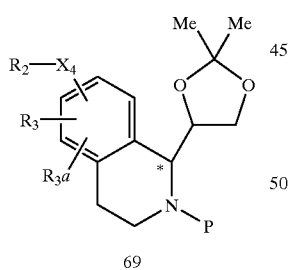
69
Scheme 11: Alternate Core
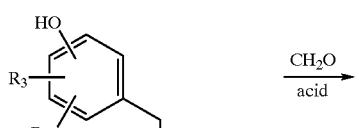
73
CH₂O
acid
→
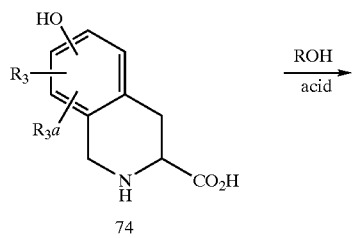
74
ROH
acid
→
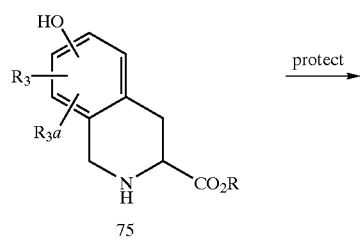
75
protect
→
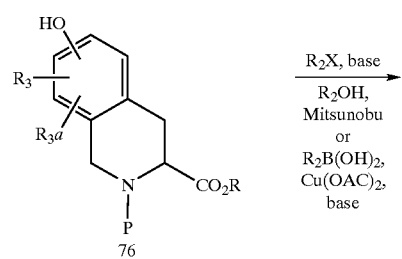
76
R₂X, base
R₂OH, Mitsunobu
or
R₂B(OH)₂,
Cu(OAC)₂,
base
→
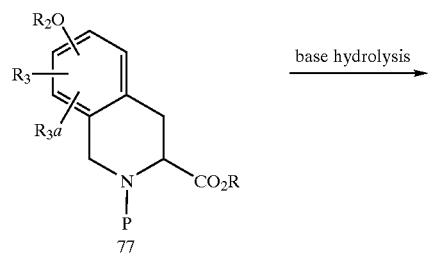
77
base hydrolysis
→
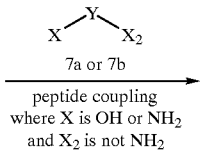
78
X—Y—X₂
7a or 7b
peptide coupling
where X is OH or NH₂
and X₂ is not NH₂
→
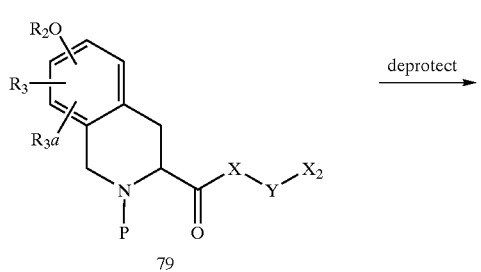
79
deprotect
→

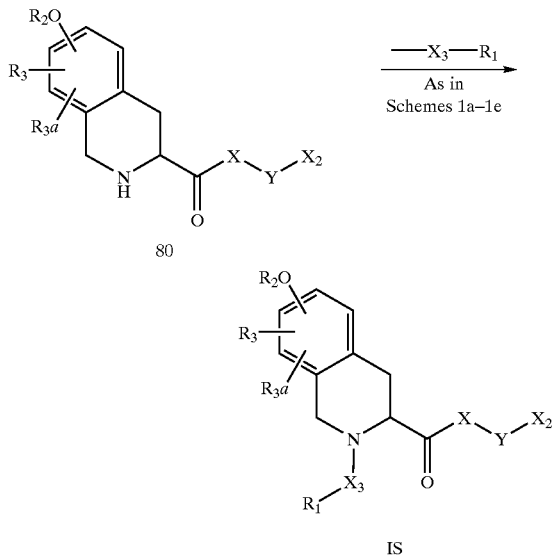

The chemokine receptor modulator compounds of formula I can be administered to animals, including man, to modulate chemokine receptor activity in vivo.

The present invention includes within its scope pharmaceutical compositions comprising, as an active ingredient, at least one of the compounds of formula I in association with a pharmaceutical carrier or diluent. Optionally, the active ingredient of the pharmaceutical compositions can comprise a growth promoting agent in addition to at least one of the compounds of formula I or another composition which exhibits a different activity, e.g., an antibiotic or other pharmaceutically active material.

The compounds of the present invention are agents that are chemokine receptor modulators and can be administered to various mammalian species, such as monkeys, dogs, cats, rats, humans, etc., in need of treatment. These agents can be administered systemically, such as orally or parenterally.

The compounds of the invention can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), anti-oxidants (ascorbic acid or sodium bisulfite) or the like. Oral dosage forms are preferred, although parenteral, intranasal or aerosol forms are quite satisfactory as well.

The dose administered must be carefully adjusted according to the age, weight, and condition of the patient, as well as the route of administration, dosage form and regimen, and the desired result. In general, the dosage forms described above may be administered in amounts from about 0.0001 to about 100 mg/kg or body weight or in an amount within the range from about 1 to about 1000 mg per day, preferably, from about 5 to about 500 mg per day in single or divided doses of one to four times daily.

The compounds of the present invention may be employed alone or in combination with each other and/or other chemokine receptor modulators or other suitable therapeutic agents useful in the treatment of the aforementioned disorders including: Anti-diabetic agents; anti-osteoporosous agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor antagonists); anabolic agents; HIV or AIDS therapies; therapies useful in the treatment of Alzheimer's disease and other cognitive disorders; therapies useful in the treatment of sleeping disorders; anti-proliferative agents; anti-tumor agents; and/or anti-ulcer and gastroesopheageal reflux disease agents.

Examples of suitable anti-diabetic agents for use in combination with the compounds of the present invention include biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DP4) inhibitors.

Examples of suitable anti-osteoporosous agents for use in combination with the compounds of the present invention include alendronate, risedronate, raloxifene, calcitonin, non-steroidal progestin receptor agonists, RANK ligand agonists, calcium sensing receptor antagonists, TRAP inhibitors, selective estrogen receptor modulators (SERM), estrogen and AP-1 inhibitors;

Examples of suitable anti-obesity agents for use in combination with the compounds of the present invention include aP2 inhibitors such as those disclosed in U.S. Ser. No. 09/519,079 filed Mar. 6, 2000, PPAR gamma antagonists, PPAR delta agonists, and orlistat.

Examples of suitable antinflammatory agents for use in combination with the compounds of the present invention include prednisone, dexamethasone, Enbrel, cyclooxygenase inhibitors (i.e., COX-1 and/or COX-2 inhibitors such as NSAIDs, aspirin, indomethacin, ibuprofen, piroxicam, Naproxen, Celebrex, Vioxx), CTLA4-Ig agonists/antagonists, CD40 ligand antagonists, integrin antagonists, alpha4 beta7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., zelmac and Maxi-K openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, choesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase inhibitiors for use in combination with the compounds of the present invention include PDEIII inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone and SARMs.

Examples of suitable HIV or AIDS therapies for use in combination with the compounds of the present invention include indinavir sulfate, saquinavir, saquinavir mesylate, amprenavir, ritonavir, lopinavir, ritonavir/lopinavir combinations, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, taxol, FK 506, and adriamycin.

Examples of suitable anti-tumor agents for use in combination with the compounds of the present invention include taxol, adriamycin, epothilones, cisplatin and carboplatin.

The above other therapeutic agents, when employed in combination with the compounds of the present invention, may be used, for example, in those amounts indicated in the Physicians' Desk Reference (PDR) or as otherwise determined by one of ordinary skill in the art.

The utility of the compounds of the present invention as chemokine receptor modulators may be demonstrated by methodology known to those skilled in the art, such as the assays for CCR2 and CCR3 ligand binding, as disclosed by Ponath, et al., *J. Exp. Med.* 1996, 183, 2437–2448, Uguccioni, et al., *J. Clin. Invest.* 1997, 100, 1137–1143, and White, et al., 2000, *J. Biol. Chem.* 2000, 275, 36626–36631. Cell lines that express the receptor of interest include those naturally expressing the receptor, or a cell engineered to express a recombinant chemokine receptor, such as CHO, HEK-293, or RBL. The preferred compounds of the present invention have activity in binding to the CCR3 receptor in the aforementioned assays.

The following Examples represent preferred embodiments of the invention, and are not intended to limit the scope of the claimed invention.

All temperatures are in ° C. unless indicated otherwise.

GENERAL EXPERIMENTAL

HPLCa: Shimadzu, 0–100% B [MeOH:H$_2$O:0.2% H$_3$PO$_4$], 4 min. gradient, 1 min. hold, 220 nM, YMC S5 ODS 4.6×50 mm. HPLCa1: Shimadzu, 0–100% B [MeOH:H$_2$O:0.2% H$_3$PO$_4$], 2 min. gradient, 1 min. hold, 220 nM, YMC S5 ODS4.6×33 mm. HPLCb: Shimadzu, 0–100% B [MeOH:H$_2$O:0.1% TFA], 4 min. gradient, 1 min. hold, 220 nM, YMC S5 ODS 4.6×50 mm.

EXAMPLE 1

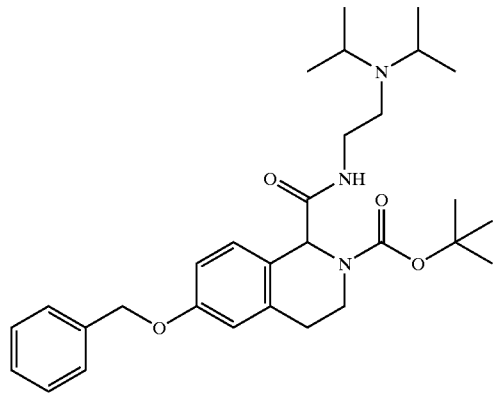

1-[[[2-[bis(1-Methylethyl)amino]ethyl]amino]carbonyl]-3,4-dihydro-6-(phenylmethoxy)-2(1H)-isoquinoline-carboxylic Acid 1,1-dimethylethyl Ester

A.

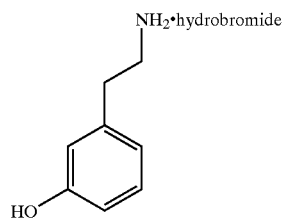

Hydrobromic acid (48%, 500 mL) was added to 3-methoxyphenethylamine (150 g, 0.992 mmol). The formed white solid dissolved upon warming. The reaction mixture was heated at reflux for 3 days. Water was removed by coevaporation with toluene to give the title compound (298 g, >100%) as a white solid %): LC/MS (electrospray, +ions) m/z 138(M+H).

B.

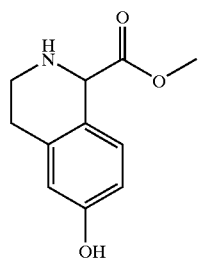

A mixture of Part A compound (266 g, 1.22 mol), glyoxylic acid monohydrate (130 g, 1.41 mol) and 5% hydrochloric acid solution (2 L) was warmed at 80° C. under nitrogen for 8 h. Water was removed by azeotroping with toluene. The residue was dissolved in methanol (1500 mL), and then chlorotrimethylsilane (200 mL, 1.58 mol) was added. The suspension became clear after warming to 49° C. Stirring was continued at 49° C. for 12 h. The reaction mixture was concentrated, and the residue was treated with saturated aqueous sodium bicarbonate solution to make it basic. The aqueous solution (saturated with sodium chloride) was extracted with ethyl acetate (6×300 mL) until no product was visible in the aqueous layer by TLC. Solvent was removed in vacuo. Ethanol was added to the residue, and the yellow solid that formed was collected by filtration to give the title compound (87 g, 35%): LC/MS (electrospray, +ions) m/z 208(M+H).

C.

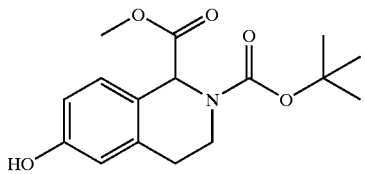

A solution of di-tert-butyl dicarbonate (89 g, 0.40 mol) in tetrahydrofuran (500 mL) was slowly added to a suspension of Part B compound (76 g, 0.37 mol) in tetrahydrofuran (800 mL) and triethylamine (5 mL, 0.036 mol). The reaction was stirred at ambient temperature for 2 h until bubbling stopped. The reaction solution was passed through a pad of silica gel, rinsing with tetrahydrofuran. The solvent was removed, and the residue was dissolved in ethyl acetate (400 mL). The ethyl acetate solution was washed with water (500 mL), 10% aqueous citric acid solution (200 mL) and brine. The organic layer was dried over sodium sulfate, and the mixture was filtered. The filtrate was concentrated to give the title compound (128 g, 100%) as a light brown oil: LC/MS (electrospray, +ions) m/z 308(M+H).

D.

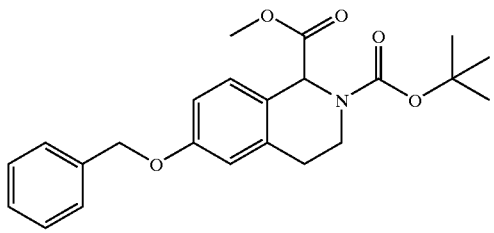

A mixture of Part C compound (48.0 g, 0.156 mol), benzyl bromide (25 mL, 0.209 mol) and potassium carbonate (74 g, 0.536 mol) in dimethylformamide (500 mL) was stirred overnight. The reaction mixture was filtered, rinsing with ethyl acetate, and the solvent was removed in vacuo. The residue was dissolved in ethyl acetate, and the organic solution was washed with water followed by 10% aqueous citric acid solution (2×) and brine and then dried over sodium sulfate. The mixture was filtered and the filtrate concentrated. Purification by silica gel column chromatography, eluting with 10% ethyl acetate in heptane (6 L) followed by 20% ethyl acetate in heptane (4 L), gave the title compound (58.0 g, 93%) as a white foam.

E.

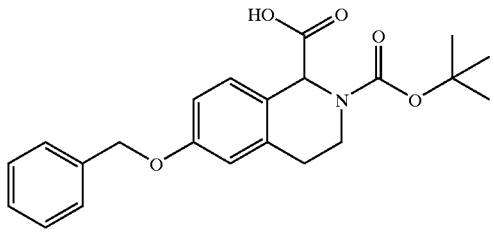

Part D compound (21.51 g, 54.12 mmol) was dissolved in methanol (50 mL) and tetrahydrofuran (50 mL), and then water (50 mL) was added. To the resultant milky mixture was added sodium hydroxide (6.49 g, 162.3 mmol). Within 10 min, the reaction temperature rose from 23° C. to 40° C., and the reaction became clear. After stirring for 2.5 h, the reaction mixture was transferred to a separatory funnel and water (50 mL) was added. The product was extracted with ethyl acetate (2×250 mL). The rich organic layer was washed with 1 N hydrochloric acid solution (250 mL) followed by brine (100 mL) and dried over sodium sulfate. The mixture was filtered, and the filtrate was concentrated and dried in vacuo to give the title compound (17.3 g, 83%) as a white foam: LC/MS (electrospray, +ions) m/z 382(M+H).

F.

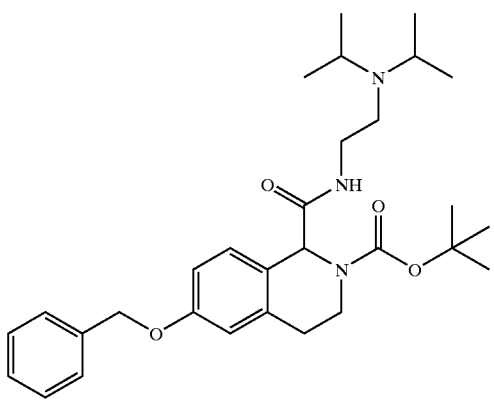

A solution of Part E compound (500 mg, 1.3 mmol) in dimethylformamide (3 mL) was treated with diisopropyl-ethylenediamine (248 μL, 1.37 mmol) followed by 1-hydroxy-7-azabenzotriazole (213 mg, 1.56 mmol) and 1-(3-dimethylaminopropyl)-3-ethylcarbodiimide hydrochloride (300 mg, 1.56 mmol). The mixture was stirred overnight at ambient temperature. Evaporation of the solvent gave a residue, which was dissolved in dichloromethane. The dichloromethane solution was washed with water (3×30 mL) and dried over magnesium sulfate. The mixture was filtered, and the filtrate was concentrated. Silica gel flash column chromatography purification gave the title product (523 mg, 79%) as a white solid: LC/MS (electrospray, +ions) m/z 510(M+H).

EXAMPLE 1A

An alternative procedure for the preparation of Example 1 Part B compound follows:

A.

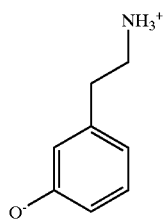

A solution of 48% hydrobromic acid (100 mL) was added slowly and cautiously to a flask at 4° C. containing m-methoxyphenethylamine (50 g, 0.331 mol). The amine salt formed as a white solid. The reaction mixture was heated at 140° C. under gentle reflux for 18 h. After cooling, the solvent was evaporated to give a white residue, which was further dried under high vacuum. The solid was then dissolved in water, and dichloromethane was added to extract the non-polar impurities. The aqueous layer was made alkaline by the addition of powdered sodium carbonate. Water was evaporated to give a white solid, which was dried in vacuo. The extraction of the product was done by the addition of ethyl acetate, with heating at reflux. Molecular sieves (4 Å) were added to absorb the residual water. The mixture was decanted. The ethyl acetate extraction was repeated until only trace amounts of product were present in the extract. The ethyl acetate extracts were combined. Ethyl acetate was evaporated to give the title product (29 g, 64%) as a white solid.

B.

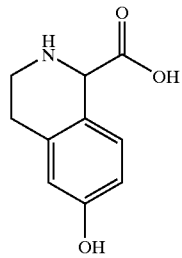

To a 4° C. solution of Part A compound (3.08 g, 22.5 mmol) in denatured ethanol (70 mL) was added a solution of glyoxylic acid monohydrate (2.0 g, 22 mmol) in ethanol (10 mL) dropwise. Shortly after the addition of glyoxylic acid, a white precipitate formed. The cooling bath was removed, and the reaction mixture was stirred for 2 h at ambient temperature. Filtration gave the title product (3.1 g, 73%) as a white solid: LC/MS (electrospray, +ions) m/z 194(M+H).

C.

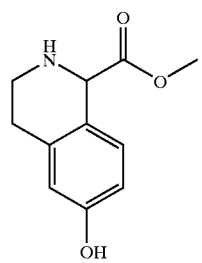

A solution of hydrogen chloride in methanol (150 mL), prepared by the addition of acetyl chloride (13 mL) to methanol (500 mL), was added to Part B compound (6.0 g, 31.1 mmol). The mixture was heated at reflux for 48 h. The solvent was evaporated to give a white residue, to which ethyl acetate and saturated aqueous sodium carbonate were added. The two layers were separated, and extraction of the aqueous layer with ethyl acetate was repeated several times. The ethyl acetate layers were combined and dried over magnesium sulfate. The mixture was filtered, and the filtrate was concentrated to give the title product (3.93 g, 61%) as a yellow solid: LC/MS (electrospray, +ions) m/z 208(M+H).

EXAMPLE 1B

An alternative procedure for the preparation of Example 1 Part C compound follows:

A.

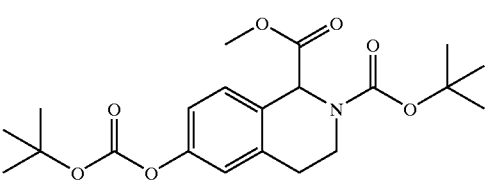

To a mixture of Example 1 Part B compound (3.0 g, 14.5 mmol) and di-tert-butyl dicarbonate (8.21 g, 37.6 mmol) was added tetrahydrofuran (75 mL). This mixture was stirred to give a slurry. Triethylamine (5.3 mL, 38.0 mmol) was added, and the reaction mixture was stirred at ambient temperature for 18 h. The title compound was used in the next step without work-up.

B.

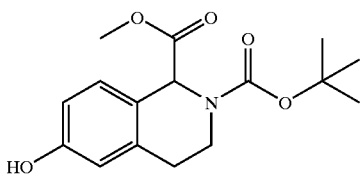

To the reaction mixture containing Part A compound was added methanol (30 mL) and then 25 wt % sodium methoxide in methanol (15 mL). The resultant viscous reaction mixture was stirred at ambient temperature for 2 h. A solution of 10% acetic acid in water (50 mL) was added. The reaction temperature rose from 22° C. to 34° C., and gas evolution was observed. Tetrahydrofuran and methanol were removed by rotovaporation. The product was extracted with dichloromethane (2×50 mL). The organic layer was washed with water (50 mL) and brine (25 mL) and dried over sodium sulfate. The mixture was filtered, and the filtrate was concentrated to give the title product (4.6 g) as a white foam: LC/MS (electrospray, +ions) m/z 308(M+H).

EXAMPLE 2

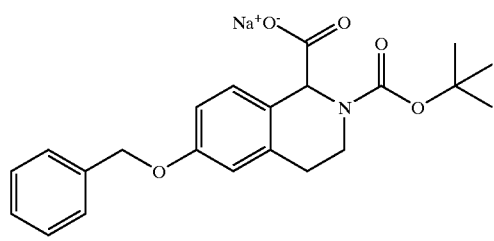

To a solution of Part D compound from Example 1 (0.60 g, 1.51 mmol) in tetrahydrofuran (6 mL) was added 1 N sodium hydroxide solution (6 mL, 6 mmol). After stirring for 45 h, the reaction mixture was transferred to a separatory funnel, and the product was extracted with ethyl acetate (2×10 mL). The organic layers were combined and washed with 1 N sodium hydroxide solution (5 mL) and brine (5 mL) and then dried over anhydrous sodium sulfate. The mixture was filtered, and the filtrate was concentrated and dried in vacuo to give the title compound (0.41 g, 67%) as a white solid.

EXAMPLE 3

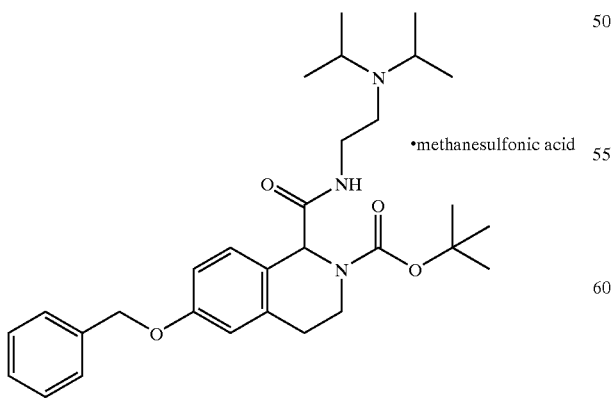

·methanesulfonic acid

To a solution of Part F compound from Example 1 (107 mg, 0.210 mmol) in dichloromethane (10 mL) was added methanesulfonic acid (16 μL, 0.247 mmol). The solvent was evaporated, and the residue was dissolved in acetone. Hexanes was then added. Concentration gave the title product (110 mg, 86%) as a white solid: LC/MS (electrospray, +ions) m/z 510 (M+H).

EXAMPLE 4

Isomer A and Isomer B

A.

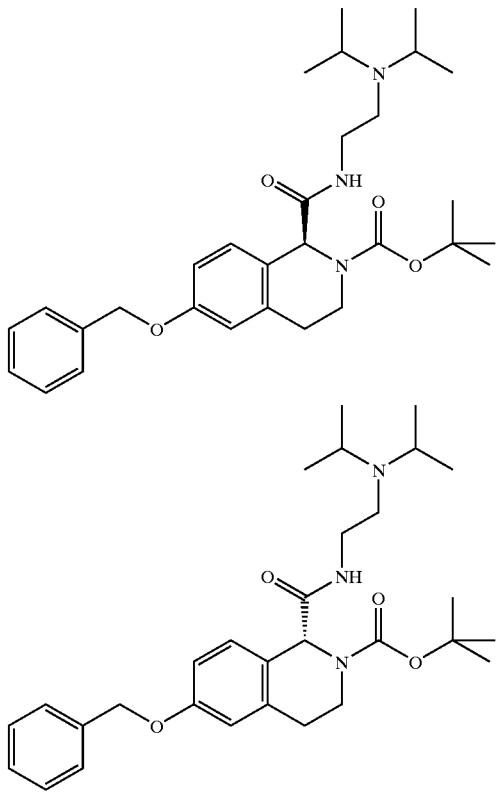

Example 1, title compound (2 batches of 500 mg) was resolved on Chiralpak OD column (50×500 mm), eluting with 20% isopropanol in hexanes to give the title compounds, Isomer A (0.350 g, 35%) and Isomer B (0.356 g, 36%).

Isomer A

[α]D=−22.7° (c=0.1; methanol)

Isomer B

[α]D=+28.40° (c=0.1; methanol)

EXAMPLE 5

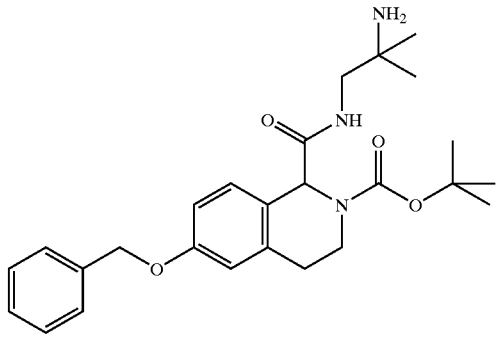

A solution of Part E compound from Example 1 (100 mg, 0.26 mmol) in dimethylformamide was treated with 1,2-diamino-2-methylpropane (27 μL, 0.26 mmol) followed by 1-hydroxy-7-azabenzotriazole (42 mg, 0.31 mmol) and 1,3-diisopropylcarbodiimide (50 μL, 0.32 mmol), and the reaction mixture was stirred overnight at ambient temperature. The crude reaction mixture was loaded onto a SCX column that had been washed with methanol. The column was washed with methanol (3×10 mL) and then the product was eluted from the column with 2.0 M ammonia in methanol (6 mL). Evaporation of the solvent gave the title product (109 mg, 92%) as a white solid: LC/MS (electrospray, +ions) m/z 454 (M+H).

EXAMPLES 6 TO 26

In a manner analogous to that of Example 5, Examples 6–26 listed in the table below were prepared from Part E compound of Example 1 and the respective amines. Examples 6 to 26 compounds were purified by preparative HPLC, eluting with a gradient system of methnol and water with 0.2% trifluoroacetic acid and neutralized with sodium bicarbonate. Example 19–26 compounds were prepared as methanesulfonic acids in a manner analogous to that of Example 3, except that exactly one equivalent of methanesulfonic acid was used. In the tables of compounds which follow, the $X_1$ designation refers to the point of attachment of the particular $R_1$ moiety shown to the remainder of the molecule.

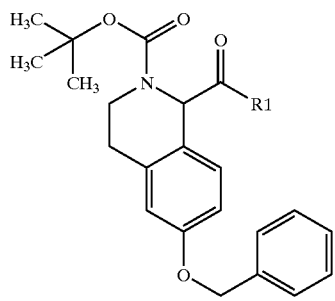

| Example No. | $X_1$—R1 | LC/MS $(M + H)^+$ |
|---|---|---|
| 6 | | 482 |
| 7 | | 477 |
| 8 | | 491 |
| 9 | | 468 |
| 10 | | 468 |
| 11 | | 494 |
| 12 | | 522 |

-continued

= X₁—R1

| Example No. | X₁—R1 | LC/MS (M + H)⁺ |
|---|---|---|
| 13 | (X₁-NH-CH₂-CH(OH)-CH₂-NH₂) | 456 |
| 14 | (X₁-NH-CH₂-(4-piperidinyl)) | 480 |
| 15 | (X₁-NH-CH₂CH₂-NH-CH₂-CH(OH)-CH₃) | 484 |
| 16 | (X₁-NH-CH₂CH₂-NH-CH₂CH₂-OH) | 470 |
| 17 | (X₁-NH-CH₂-(2-pyrrolidinyl)) | 466 |

-continued

= X₁—R1

| Example No. | X₁—R1 | LC/MS (M + H)⁺ |
|---|---|---|
| 18 | (quinuclidinyl-X₁) | 492 |
| 19 | (X₁-N(CH₃)-CH₂CH₂-N(C₂H₅)₂) | 496 |
| 20 | (X₁-NH-CH₂CH₂-N(C₂H₅)₂) | 482 |
| 21 | (X₁-NH-CH₂CH₂-N(iPr)(CH₂Ph)) | 558 |
| 22 | (X₁-NH-CH₂CH₂-N(iPr)(CH₃)) | 482 |
| 23 | (X₁-N(CH₃)-CH₂CH₂-N(iPr)₂) | 524 |
| 24 | (X₁-NH-CH₂CH₂-N(CH₃)₂) | 454 |

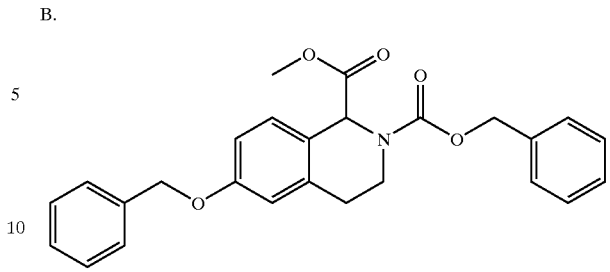

| Example No. | $X_1$—R1 | LC/MS $(M + H)^+$ |
|---|---|---|
| 25 | 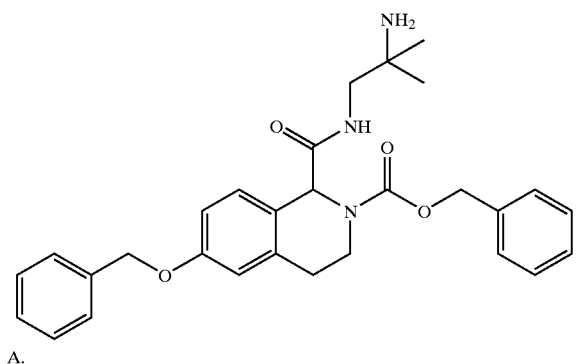 | 468 |
| 26 | 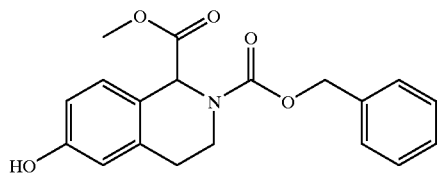 | 468 |

EXAMPLE 27

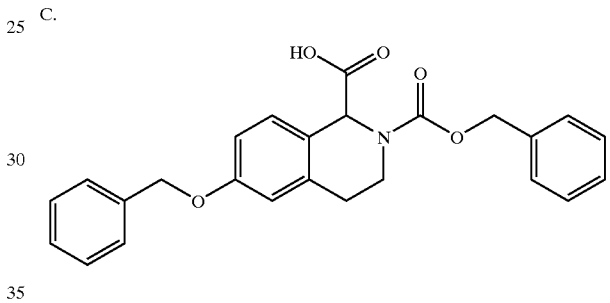

A.

To a suspension of Part B compound from Example 1 (5.0 g, 24 mmol) in dichloromethane (100 mL) was added triethylamine (4.0 mL, 29 mmol). The mixture was cooled to 4° C. and benzyl chloroformate (4.1 mL, 29 mmol) was added dropwise. The reaction mixture became clear and was stirred for 15 min. Additional dichloromethane was added and was washed with water followed by ~5% citric acid solution. The organic layer was dried over magnesium sulfate, and the mixture was filtered. The filtrate was concentrated to give the title compound (8.0 g, 97%) as a yellow solid.

B.

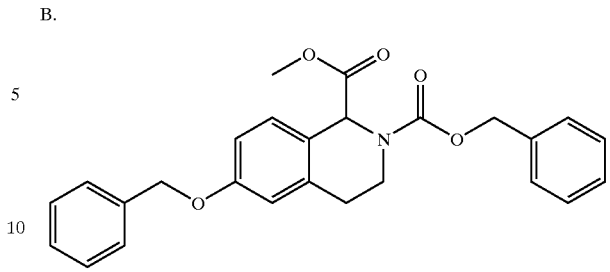

A heterogeneous mixture of Part A compound (8.0 g, 23.5 mmol), benzyl bromide (4.33 g, 23.5 mmol) and potassium carbonate (13 g, 94.1 mmol) in dimethylformamide (20 mL) was stirred at ambient temperature overnight. The reaction mixture was concentrated, and the residue was dissolved in ethyl acetate (300 mL). The organic layer was washed with water (3×200 mL) and dried over magnesium sulfate. The mixture was filtered, and the filtrate was concentrated. Flash column chromatography (1:1 ethyl acetate/hexanes) gave the title product (9.2 g, 91%) as a yellow syrup.

C.

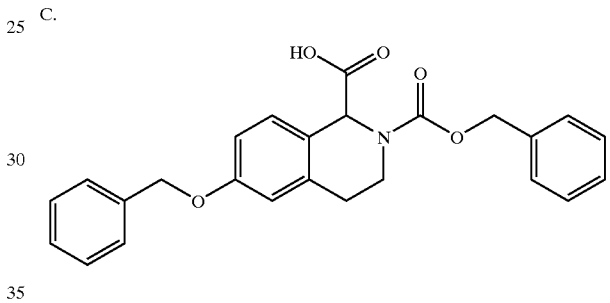

A solution of the methyl ester from Part B compound (3.6 g, 8.38 mmol) in methanol (3 mL) and tetrahydrofuran (3 mL) was treated with 10 M aqueous sodium hydroxide (2 mL, 20 mmol) and stirred at ambient temperature for 2 h. The reaction solution was acidified with 2 N hydrochloric acid solution to pH ~1–2. The product was extracted with ethyl acetate. The organic layer was washed with brine (2×) and dried over magnesium sulfate. The mixture was filtered, and the filtrate was concentrated to give the title product (3.0 g, 86%) as a yellow solid: LC/MS (electrospray, +ions) m/z 418(M+H).

D.

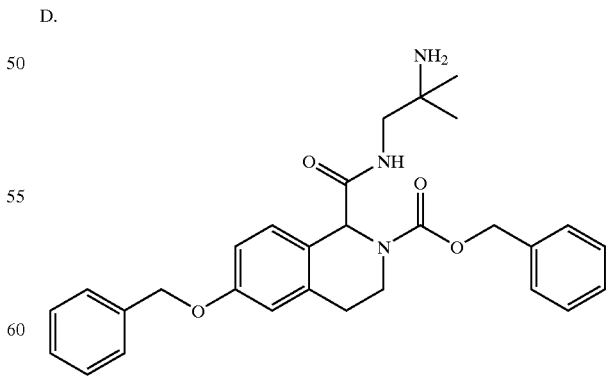

A solution of Part C compound (100 mg, 0.24 mmol) in dimethylformamide (3 mL) was treated with 1,2-diamino-2-methylpropane (30 μL, 0.29 mmol) followed by 1-hydroxy-7-azabenzotriazole (40 mg, 0.29 mmol) and 1,3- diisopropylcarbodiimide (45 μL, 0.29 mmol). The reaction mixture was stirred at ambient temperature overnight. The solvent was removed, and the residue was dissolved in methanol. This solution was applied to a CUBC×12M6 column, which was prewashed with methanol (10 mL). The column was washed with methanol (3×10 mL), and then the product was eluted with 2 M ammonium in methanol (10 mL). Evaporation of the solvent gave the title compound (110 mg, 94%) as a white solid: LC/MS (electrospray, +ions) m/z 488 (M+H).

EXAMPLES 28 TO 45

In a manner analogous to that of Example 27, Examples 28–45 listed in the table below were prepared from Part C compound of Example 27 and the respective amines. Examples 38 and 45 compounds were purified by preparative HPLC, eluting with a gradient system of methanol and water with 0.2% trifluoroacetic acid. These compounds were isolated as trifluoroacetic acid salts.

| Example No. | $X_1$—R1 | LC/MS $(M + H)^+$ |
|---|---|---|
| 28 | | 516 |
| 29 | | 511 |
| 30 | | 522 |
| 31 | | 525 |
| 32 | | 502 |
| 33 | | 502 |
| 34 | | 528 |
| 35 | | 490 |
| 36 | | 514 |
| 37 | | 518 |
| 38 | | 522 |
| 39 | | 504 |

-continued

= X₁—R1

| Example No. | X₁—R1 | LC/MS (M + H)⁺ |
|---|---|---|
| 40 | | 500 |
| 41 | | 556 |
| 42 | | 526 |
| 43 | | 544 |
| 44 | | 530 |
| 45 | | 514 |

EXAMPLE 46

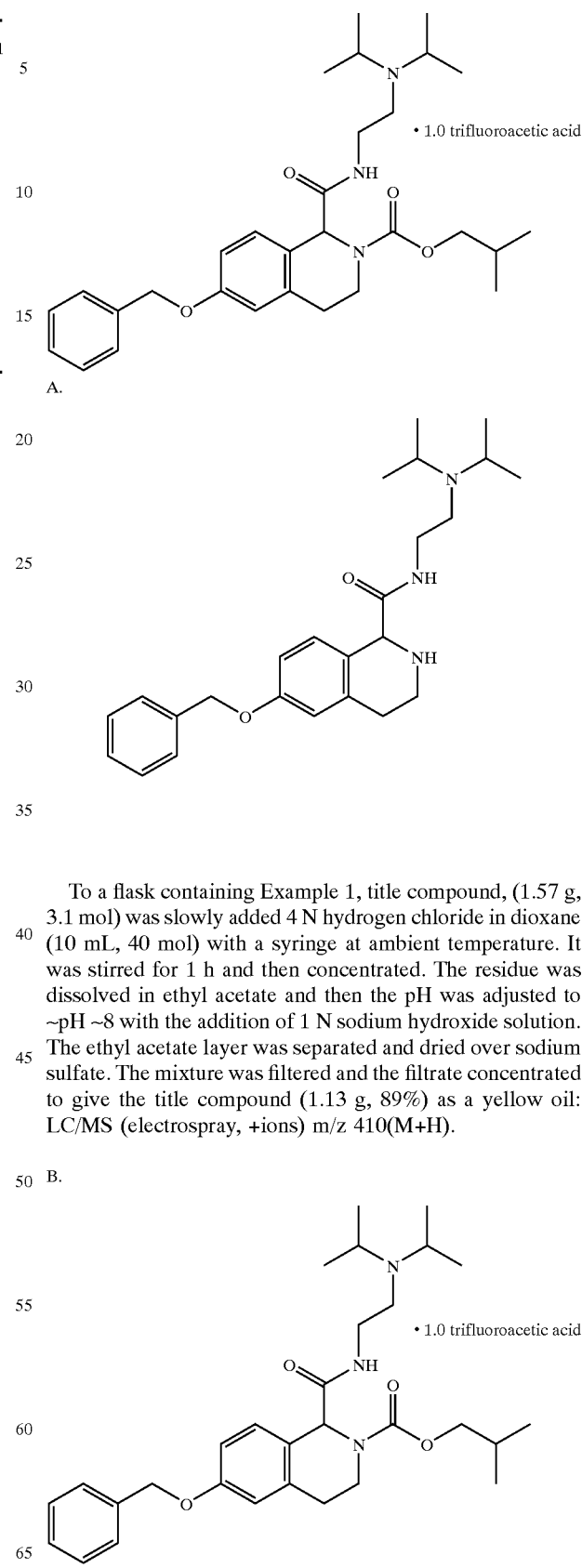

A.

To a flask containing Example 1, title compound, (1.57 g, 3.1 mol) was slowly added 4 N hydrogen chloride in dioxane (10 mL, 40 mol) with a syringe at ambient temperature. It was stirred for 1 h and then concentrated. The residue was dissolved in ethyl acetate and then the pH was adjusted to ~pH ~8 with the addition of 1 N sodium hydroxide solution. The ethyl acetate layer was separated and dried over sodium sulfate. The mixture was filtered and the filtrate concentrated to give the title compound (1.13 g, 89%) as a yellow oil: LC/MS (electrospray, +ions) m/z 410(M+H).

B.

To a 4° C. solution of Part A compound (60.0 mg, 0.147 mmol) and triethylamine (30 μL, 0.215 mmol) in tetrahydrofuran (10 mL) was added isobutyl chloroformate (28.5 μL, 0.220 mmol). The mixture was stirred at 0° C. to 10° C. for 1 h. The mixture was concentrated, and the concentrate was purified by preparative HPLC, eluting with a gradient system of 30–100% B (where A=90% water, 10% methanol, 0.2% trifluoroacetic acid and B=90% methanol, 10% water, 0.2% trifluoroacetic acid), to give the title compound (81 mg, 89%) as a yellow oil:HPLCa rt=3.99 min; LC/MS (electrospray, +ions) m/z 510(M+H).

EXAMPLE 47 TO 54

In a manner analogous to that of Example 46, Examples 47–54 compounds listed in the table below were prepared from Part A compound from Example 46 and the respective chloroformate.

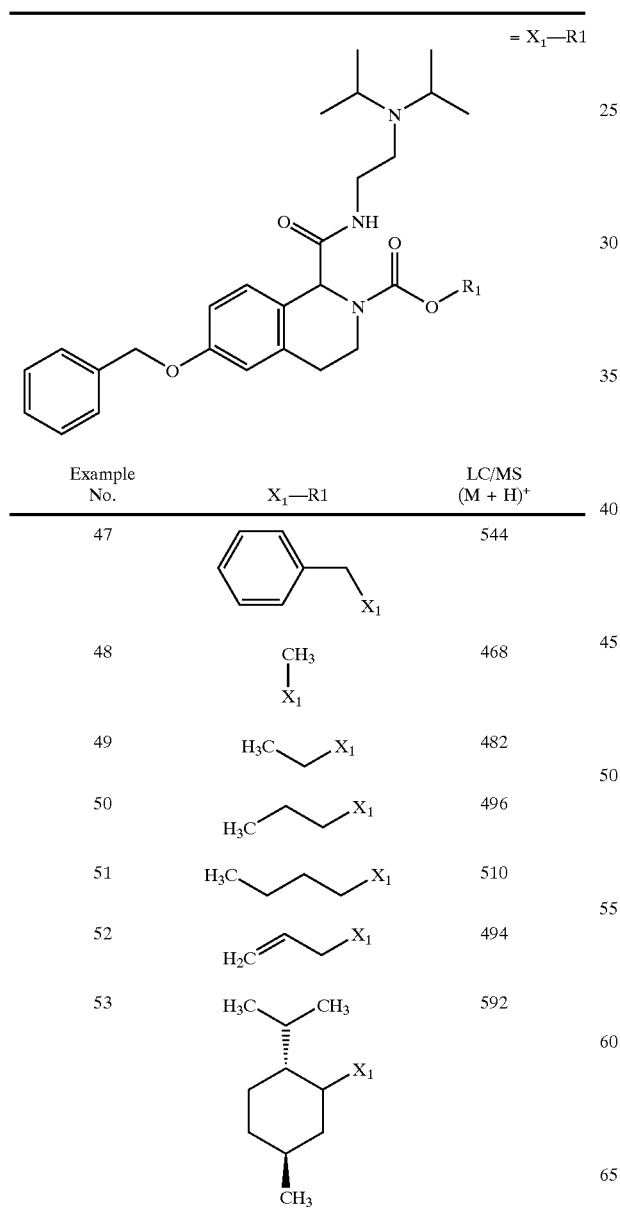

| Example No. | $X_1$—R1 | LC/MS $(M + H)^+$ |
|---|---|---|
| 47 | | 544 |
| 48 | | 468 |
| 49 | | 482 |
| 50 | | 496 |
| 51 | | 510 |
| 52 | | 494 |
| 53 | | 592 |

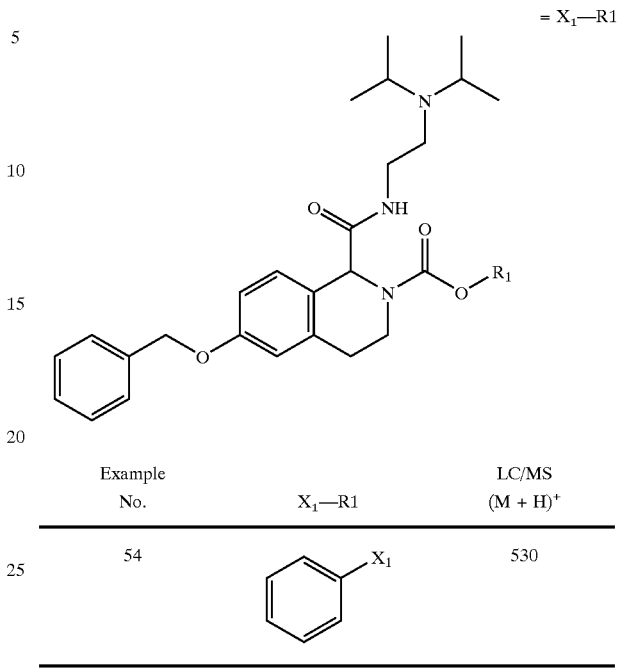

| Example No. | $X_1$—R1 | LC/MS $(M + H)^+$ |
|---|---|---|
| 54 | | 530 |

EXAMPLE 55

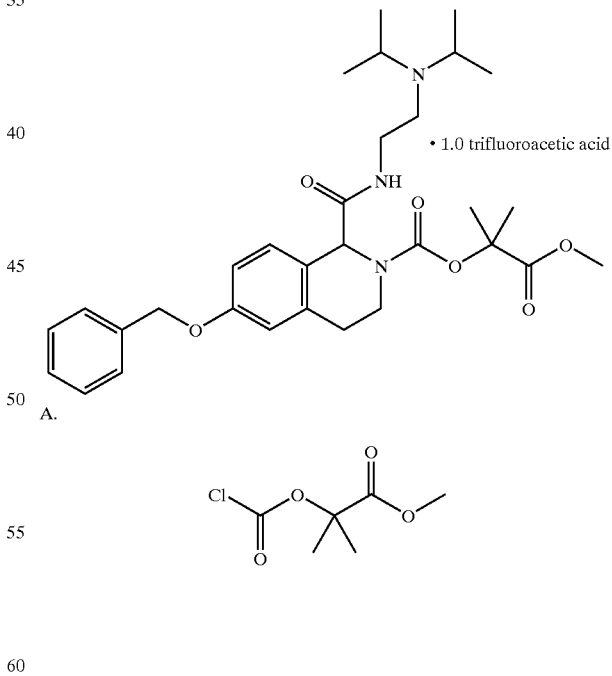

A.

To a −5° C. solution of methyl 2-hydroxyisobutyrate (118 mg, 1.0 mmol) and triethylamine (139 μL, 1.0 mmol) in dichloromethane (4 mL) was added 1.9 M phosgene in toluene (0.8 mL, 1.5 mmol). After stirring for 1 h between −5 to 0° C., the reaction mixture was concentrated and used in the next procedure without purification.

B.

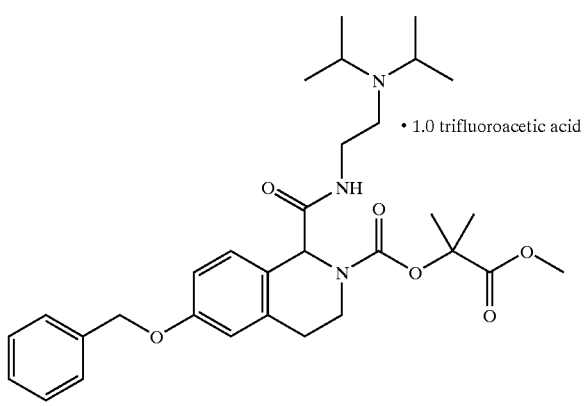

At 0° C., a solution of Part A compound (1.0 mmol) in dichloromethane (5 mL) was treated with Part A compound from Example 46 (45 mg, 0.11 mmol) followed by triethylamine (111 μL, 0.80 mmol). The reaction mixture was stirred at 0° C. to 5° C. for 2 h and then concentrated. Purification by preparative HPLC, eluting with a gradient system of 30–100% B (where A=90% water, 10% methanol, 0.2% trifluoroacetic acid and B=90% methanol, 10% water, 0.2% trifluoroacetic acid), gave the title compound (52.2 mg, 71%) as a yellow oil: HPLCa rt=3.81 min; LC/MS (electrospray, +ions) m/z 554(M+H).

EXAMPLES 56 TO 62

In a manner analogous to that of Example 55, Examples 56–62 compounds listed in the table below were prepared from Part A compound from Example 46 and the respective chloroformate prepared as in Example 55 Part A.

| Example No. | Structure | LC/MS (M + H)+ |
|---|---|---|
| 56 | 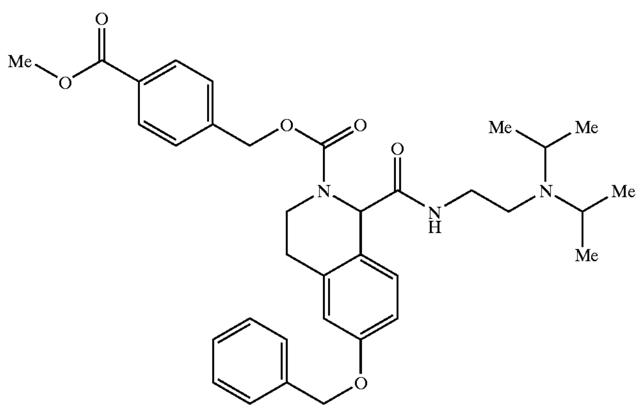 | 602 |
| 57 | 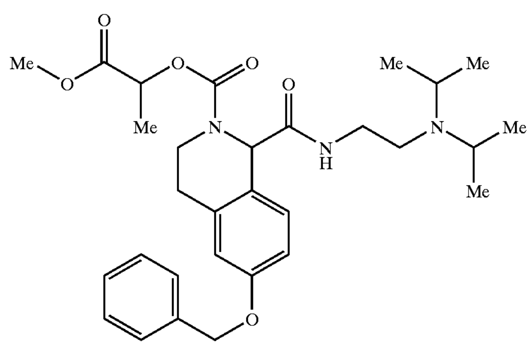 | 540 |
| 58 | 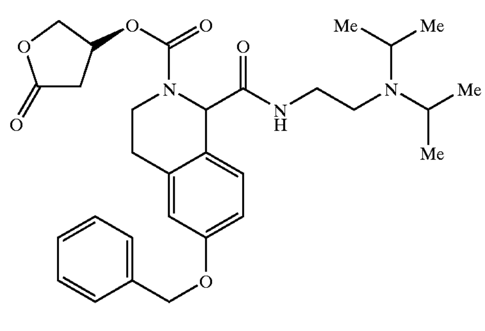 | 538 |

-continued
| Example No. | Structure | LC/MS (M + H)+ |
|---|---|---|
| 59 | 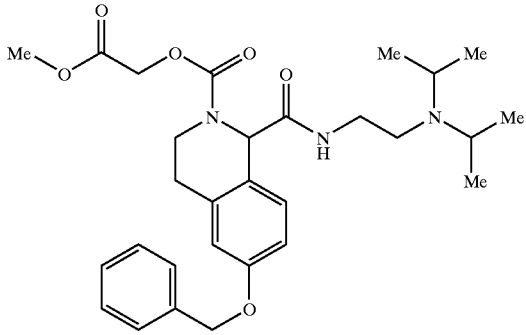 | 526 |
| 60 | 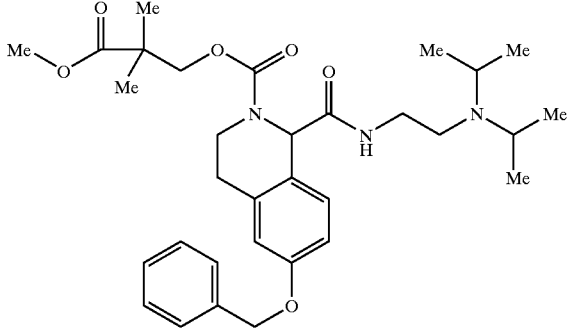 | 568 |
| 61 | 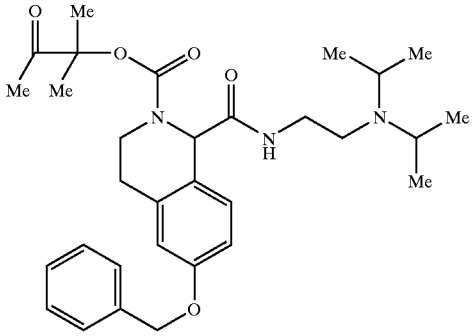 | 538 |
| 62 | 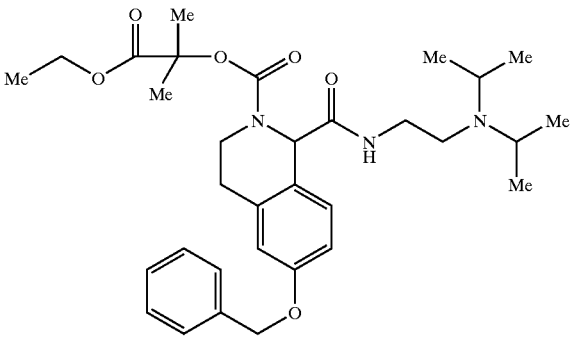 | 568 |

EXAMPLE 63

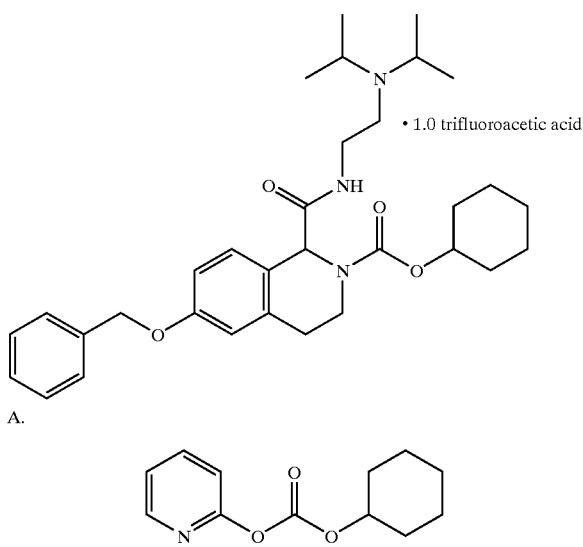

A.

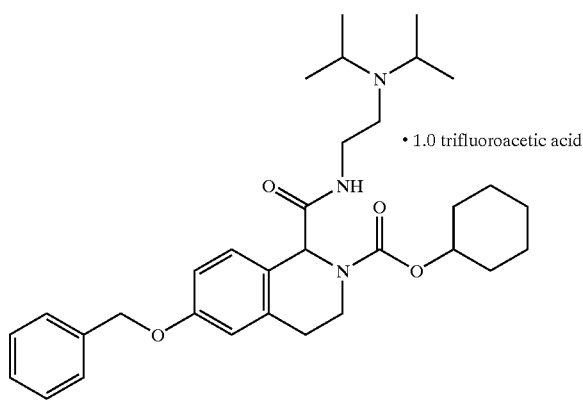

A mixture of cyclohexanol (12.5 μL, 0.12 mmol), carbonic acid di-2-pyridyl ester (25.9 mg, 0.12 mmol) and triethylamine (16.7 μL, 0.12 mmol) in dichloromethane (5 mL) was stirred at ambient temperature overnight. The reaction mixture was concentrated, and the residue was partitioned between ethyl acetate (20 mL) and concentrated sodium carbonate solution. The two layers were separated, and the organic layer was washed with brine and dried over magnesium sulfate. The mixture was filtered, and the filtrate was concentrated. The title product was purified by silica gel preparative TLC, eluting with 1:1 dichloromethane/ethyl acetate, and isolated in a yield of 26 mg (98%).

B.

To a solution of Part A compound from Example 46 (81.8 mg, 0.20 mmol) and triethylamine (27.8 μL, 0.20 mmol) in dichloromethane (7 mL) was added Part A compound (26 mg, 0.12 mmol). The reaction mixture was stirred at ambient temperature under nitrogen for 12 h. The mixture was purified by a SCX column as follows. The column was conditioned by rinsing with methanol (10 mL). The reaction mixture was loaded onto the column, followed by methanol (2×20 mL) and finally, the product was eluted with 2 N ammonia in methanol (6 mL). Further purification by preparative HPLC, eluting with 30–100% B (where A=90% water, 10% methanol, 0.2% trifluoroacetic acid and B=90% methanol, 10% water, 0.2% trifluoroacetic acid), gave the title compound (49.7 mg, 65%) as a yellow oil: LC/MS (electrospray, +ions) m/z 536(M+H).

EXAMPLE 64

Isomer A and Isomer B

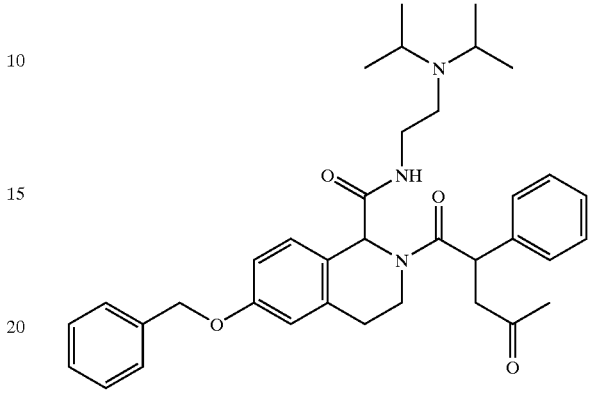

A solution of Part A compound from Example 46 (41.0 mg, 0.1 mmol) in dichloromethane (0.5 mL) was added to 2-phenyllevulinic acid (57.7 mg, 0.3 mmol) in a test tube. To the resultant mixture was added a solution of 1-hydroxybenzotriazole hydrate (33.8 mg, 0.25 mmol) in tetrahydrofuran (0.75 mL) followed by 1,3-diisopropylcarbodiimide (31.6 mg, 0.25 mmol). The reaction was stirred overnight. Methanol (3 mL) was added to ensure the reaction mixture was homogeneous. The mixture was purified by a SCX column as follows. The column was conditioned by rinsing with methanol (10 mL) and then pushing through air (10 mL). The reaction mixture was loaded onto the column. Air (10 mL) was pushed through the column followed by methanol (2×20 mL) and air (10 mL). Finally, the product was eluted with 2 N ammonia in methanol (6 mL) followed by air (10 mL). The solvent was removed from the sample by the use of a speed vacuum to give the two isomers of the title compound (56.5 mg, 97%) as an oil: HPLCb rt=3.73 and 3.92 LC/MS (electrospray, +ions) m/z 584(M+H).

EXAMPLE 65

Isomer A and Isomer B

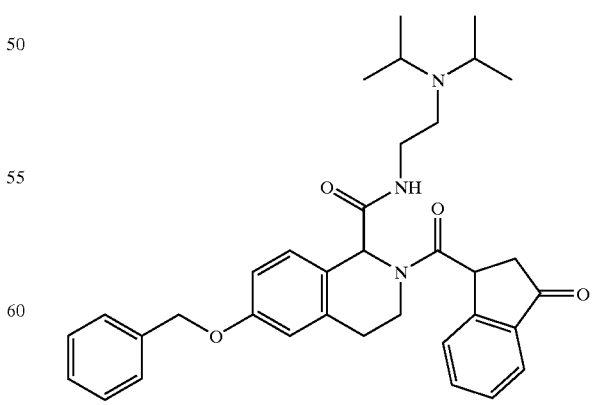

In a manner analogous to that of Example 64, the two isomers of the title compound were prepared from Part A compound from Example 46 (41.0 mg, 0.1 mmol) and 3-oxo-1-indancarboxylic acid (52.9 mg, 0.3 mmol) in yield of 55.2 mg (97%) as an oil: HPLCb rt=3.45 and 3.51 min; LC/MS (electrospray, +ions) m/z 568 (M+H).

EXAMPLES 66 TO 200

In a manner analogous to that of Examples 64 and 65, Examples 66–200 listed in the table below were prepared from Part A compound from Example 46 (0.1 mmol) and the respective carboxylic acid (0.3 mmol). A few compounds were purified by preparative HPLC, eluting with a gradient system of methanol and water with 0.2% trifluoroacetic acid. These compounds were isolated as trifluoroacetic acid salts.

| Example No. | $X_1$-R1 | LC/MS (M + H)+ |
|---|---|---|
| 66 | 2-F-benzyl | 546 |
| 67 | 3-F-benzyl | 546 |
| 68 | 4-F-benzyl | 546 |
| 69 | 3-Cl-benzyl | 562 |
| 70 | 2,4-diCl-benzyl | 597 |
| 71 | 2-CF$_3$-benzyl | 596 |
| 72 | 3-CF$_3$-benzyl | 596 |
| 73 | 2-OCH$_3$-benzyl | 558 |
| 74 | 3-OCH$_3$-benzyl | 558 |
| 75 | 4-OCH$_3$-benzyl | 558 |

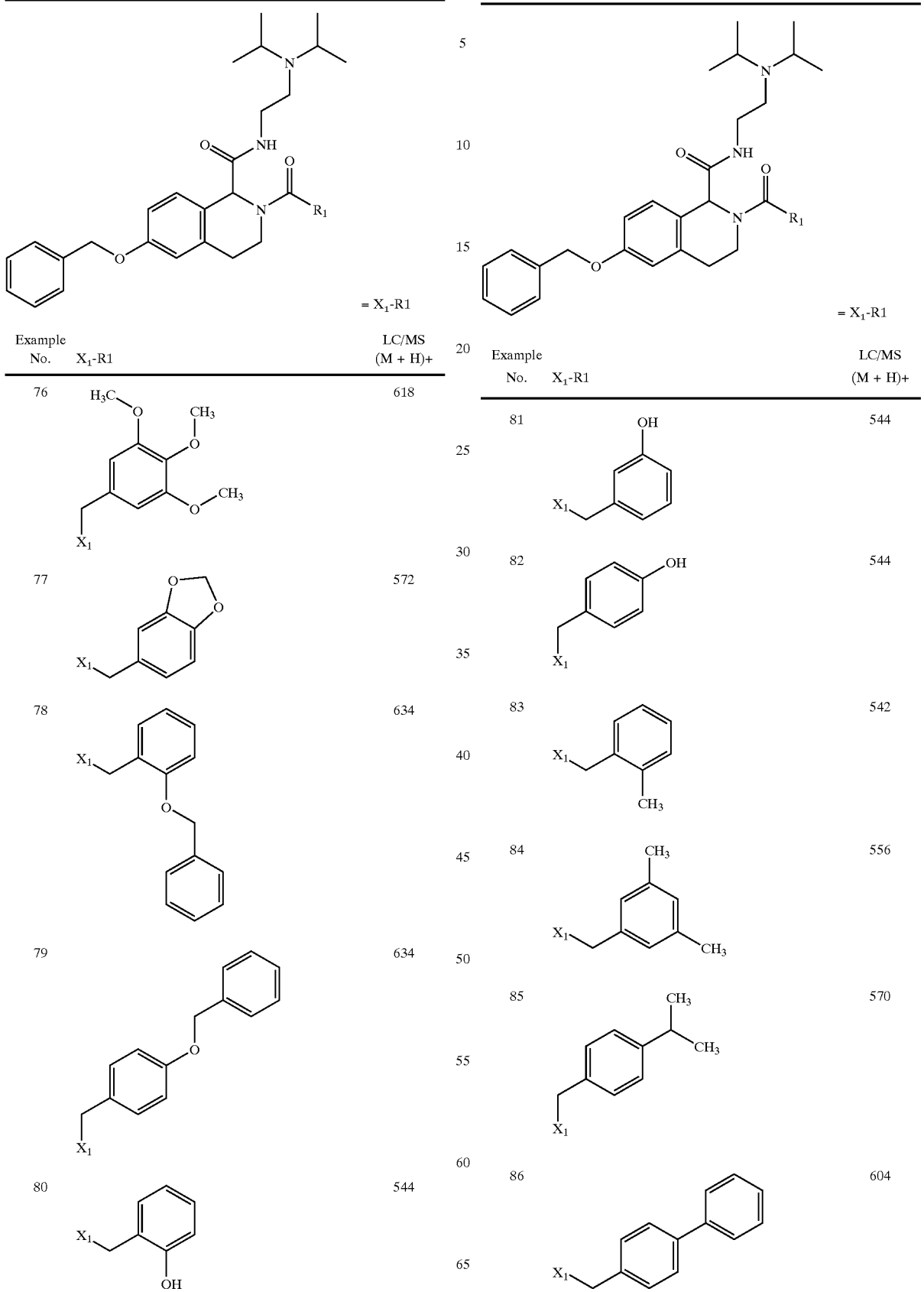

-continued
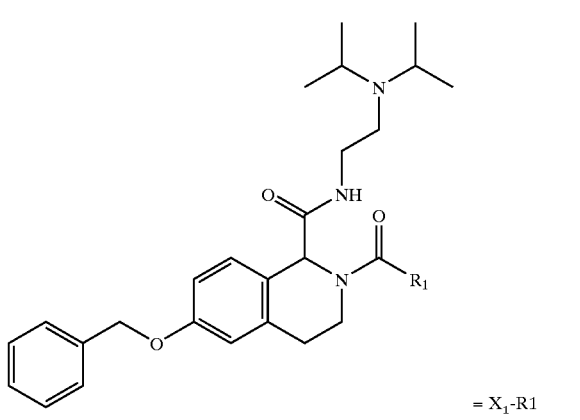
= X₁-R1
| Example No. | X₁-R1 | LC/MS (M + H)+ |
|---|---|---|
| 87 | 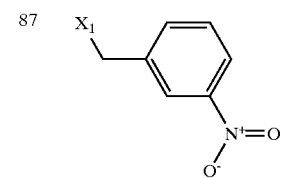 | 573 |
| 88 | 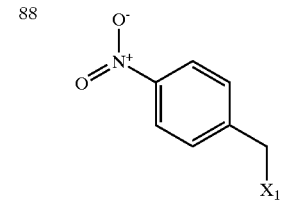 | 573 |
| 89 | 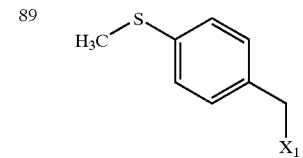 | 574 |
| 90 | 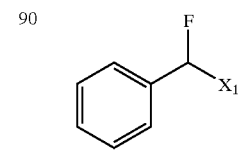 | 546 |
| 91 | 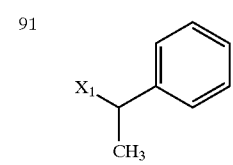 | 542 |
-continued
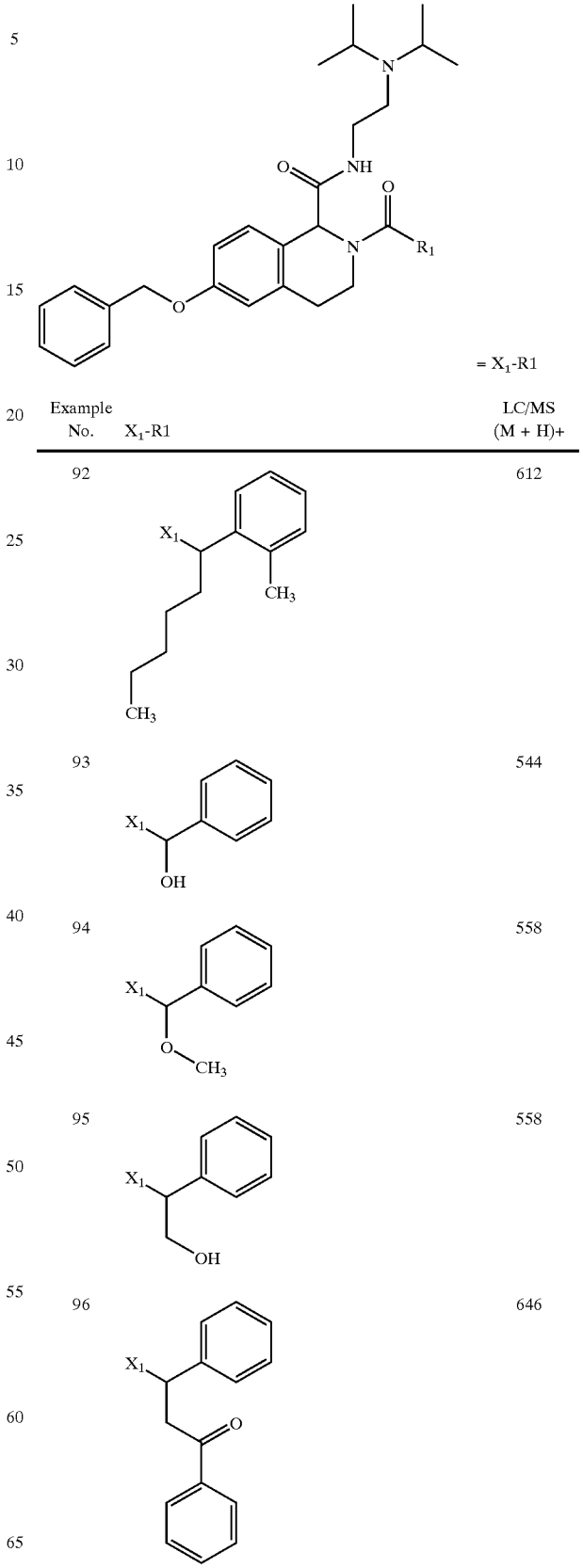

-continued
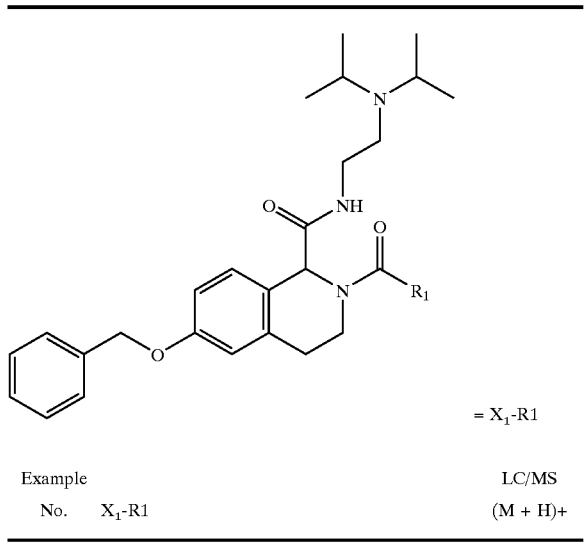
= X₁-R1
| Example No. | X₁-R1 | LC/MS (M + H)+ |
|---|---|---|
| 97 | 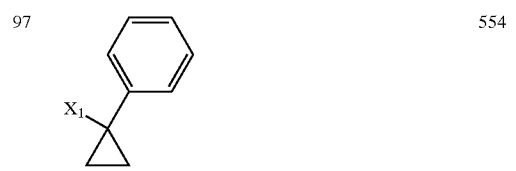 | 554 |
| 98 | 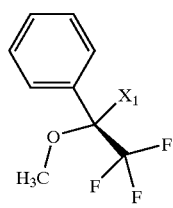 | 626 |
| 99 | 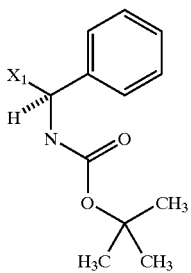 | 643 |
| 100 | 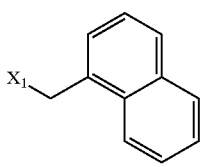 | 578 |
| 101 | 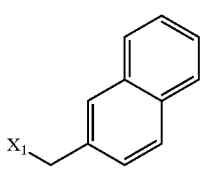 | 578 |
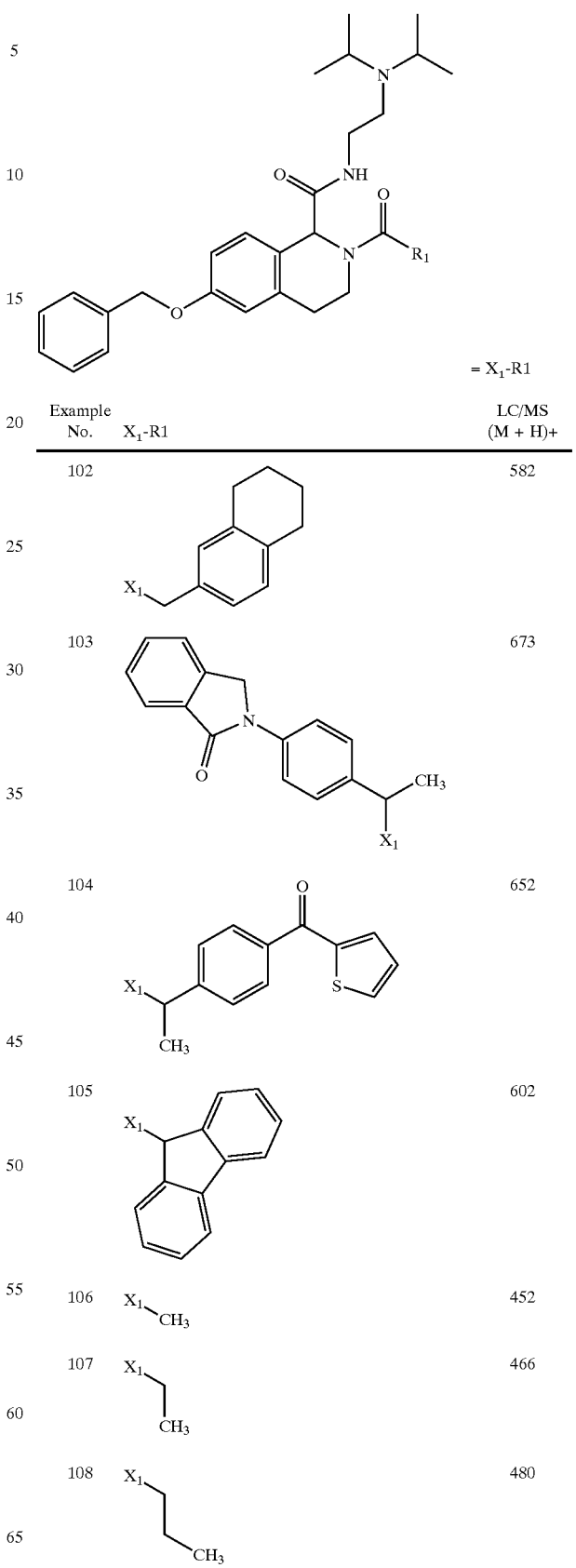

-continued
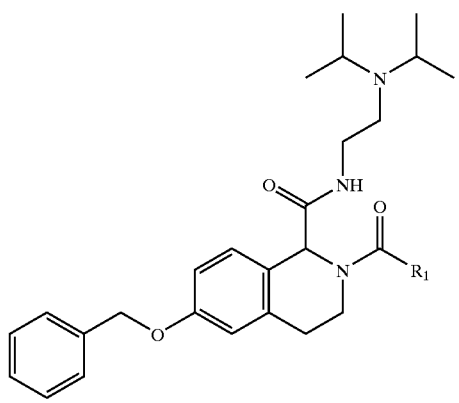
= X₁-R1
| Example No. | X₁-R1 | LC/MS (M + H)+ |
|---|---|---|
| 109 | 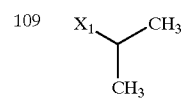 | 480 |
| 110 | 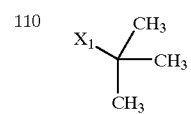 | 494 |
| 111 | 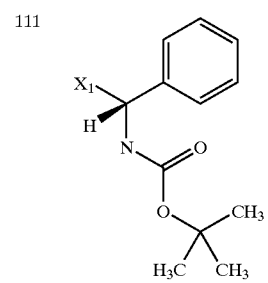 | 643 |
| 112 | 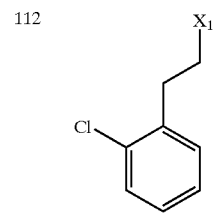 | 576 |
| 113 | 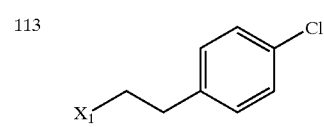 | 576 |
| 114 | 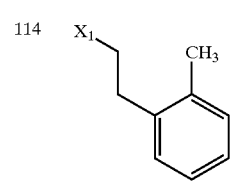 | 556 |
-continued
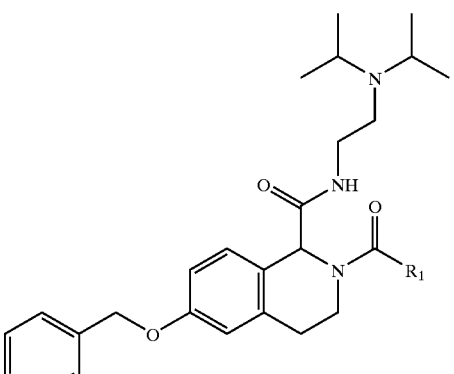
= X₁-R1
| Example No. | X₁-R1 | LC/MS (M + H)+ |
|---|---|---|
| 115 | 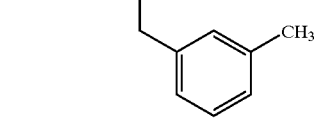 | 556 |
| 116 | 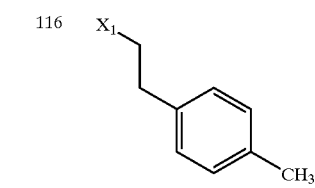 | 556 |
| 117 | 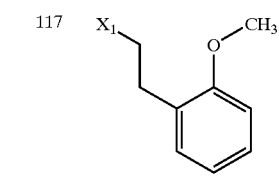 | 572 |
| 118 | 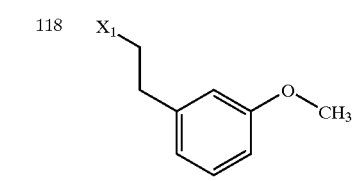 | 572 |
| 119 | 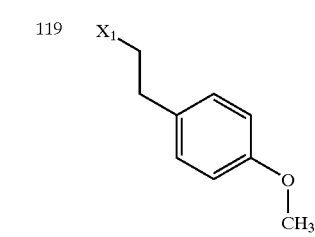 | 572 |

-continued
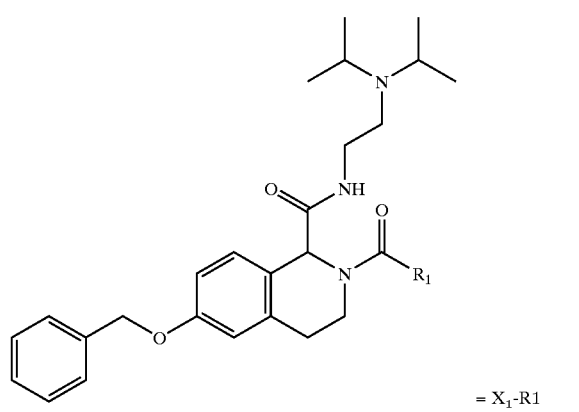
= X₁-R1
| Example No. | X₁-R1 | LC/MS (M + H)+ |
|---|---|---|
| 120 | 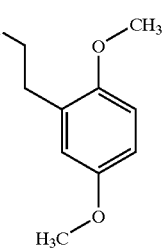 | 602 |
| 121 | 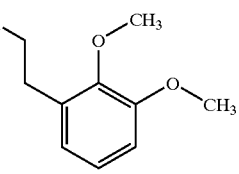 | 602 |
| 122 | 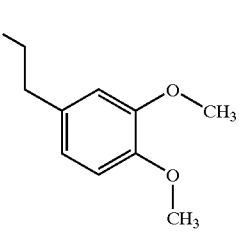 | 602 |
| 123 | 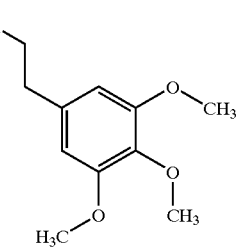 | 632 |
| 124 | 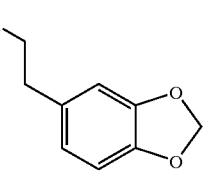 | 586 |
-continued
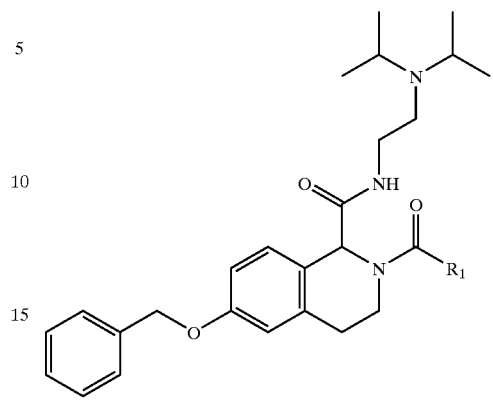
= X₁-R1
| Example No. | X₁-R1 | LC/MS (M + H)+ |
|---|---|---|
| 125 | 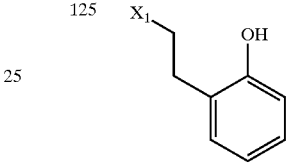 | 558 |
| 126 | 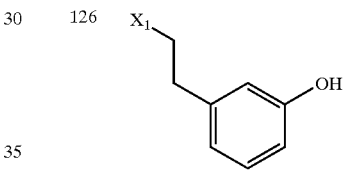 | 558 |
| 127 | 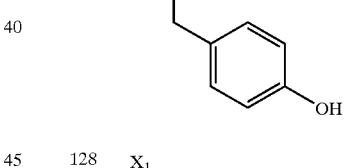 | 558 |
| 128 | 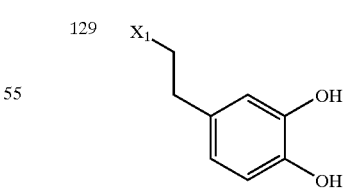 | 574 |
| 129 | 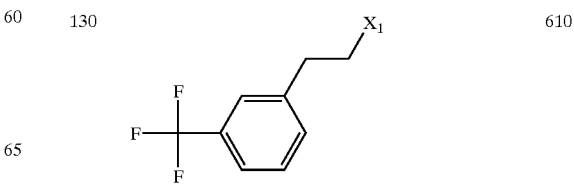 | 574 |
| 130 | 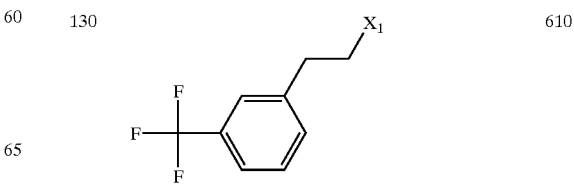 | 610 |

-continued
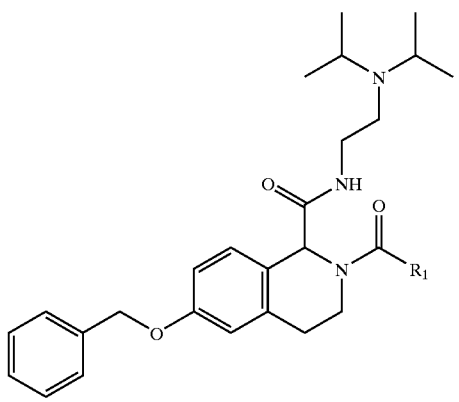
= X₁-R1
| Example No. | X₁-R1 | LC/MS (M + H)+ |
|---|---|---|
| 131 | 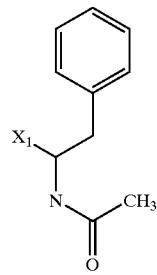 | 599 |
| 132 | 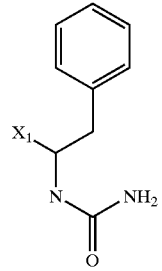 | 600 |
| 133 | 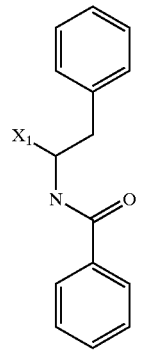 | 661 |
| 134 | 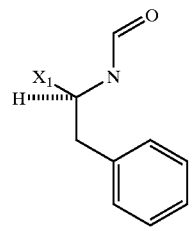 | 585 |
-continued
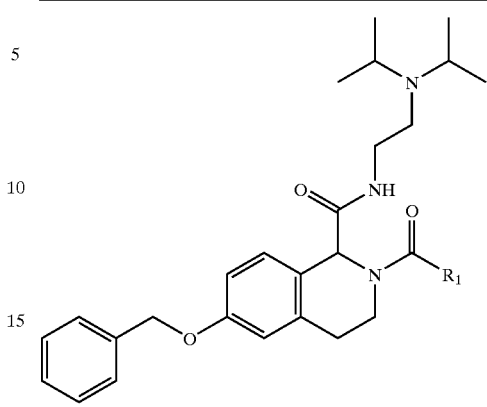
= X₁-R1
| Example No. | X₁-R1 | LC/MS (M + H)+ |
|---|---|---|
| 135 | 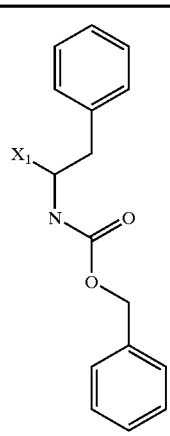 | 691 |
| 136 | 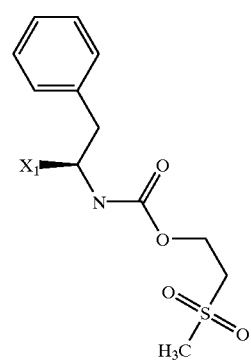 | 707 |
| 137 | 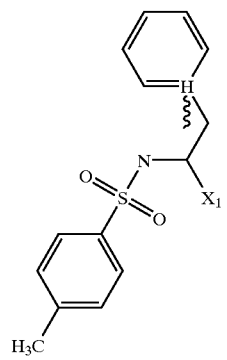 | 711 |

-continued
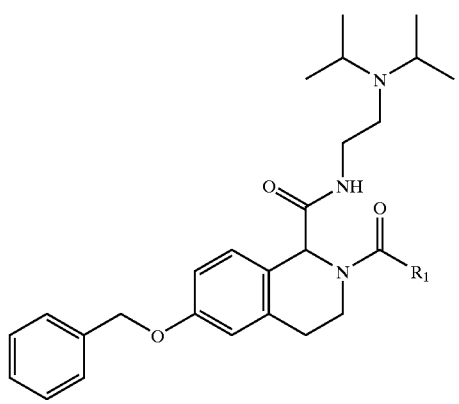
= X₁-R1
| Example No. | X₁-R1 | LC/MS (M + H)+ |
|---|---|---|
| 138 | 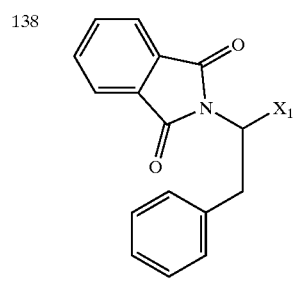 | 687 |
| 139 | 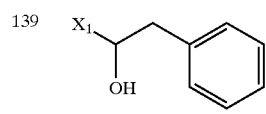 | 558 |
| 140 | 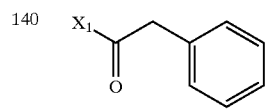 | 556 |
| 141 | 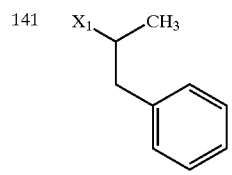 | 556 |
| 142 | 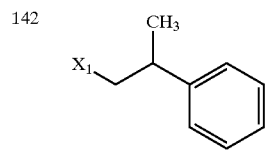 | 556 |
| 143 | 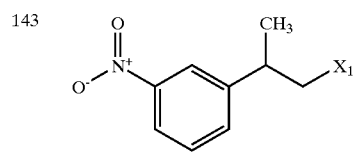 | 601 |
-continued
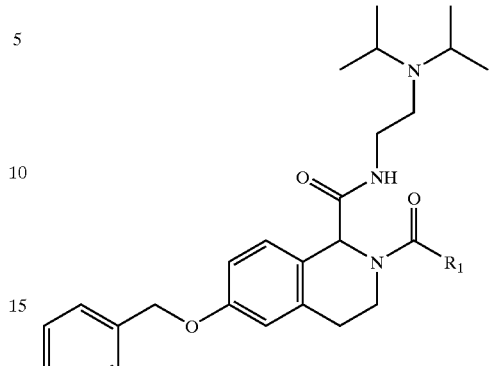
= X₁-R1
| Example No. | X₁-R1 | LC/MS (M + H)+ |
|---|---|---|
| 144 | 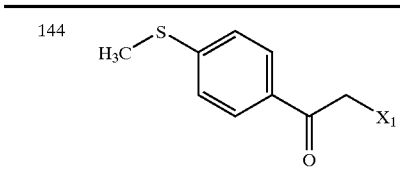 | 602 |
| 145 | 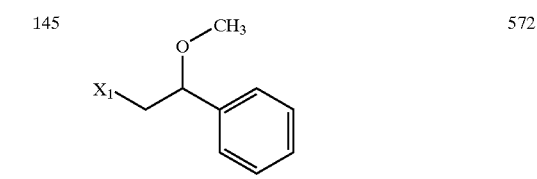 | 572 |
| 146 | 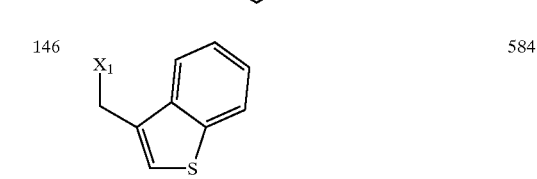 | 584 |
| 147 | 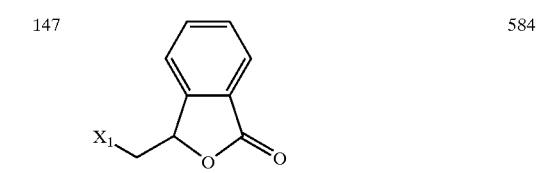 | 584 |
| 148 | 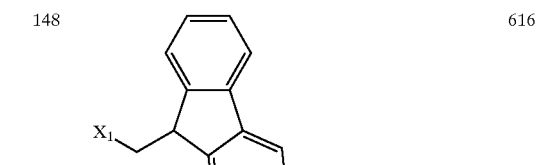 | 616 |
| 149 | 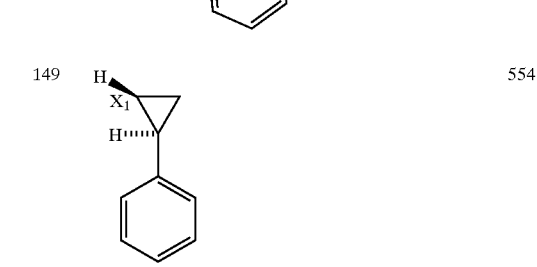 | 554 |

-continued

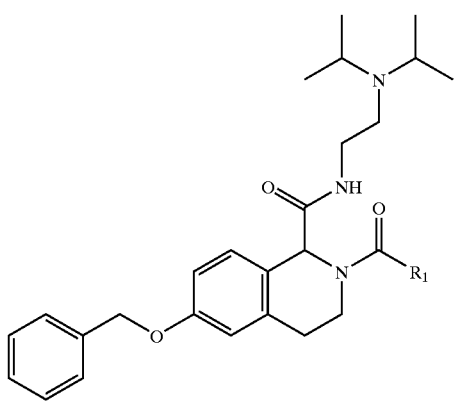

= X₁-R1

| Example No. | X₁-R1 | LC/MS (M + H)+ |
|---|---|---|
| 150 | (4-chlorobenzoyl-2-methyl-5-methoxyindol-3-yl)methyl-X₁ | 749 |
| 151 | (5-fluoro-2-methyl-1-(4-methylsulfinylbenzylidene)inden-3-yl)methyl-X₁ | 748 |
| 152 | 2-(tert-butoxycarbonyl)-1,2,3,4-tetrahydroisoquinolin-3-yl-X₁ | 669 |
| 153 | cinnamoylamino-phenethyl-X₁ | 687 |

-continued

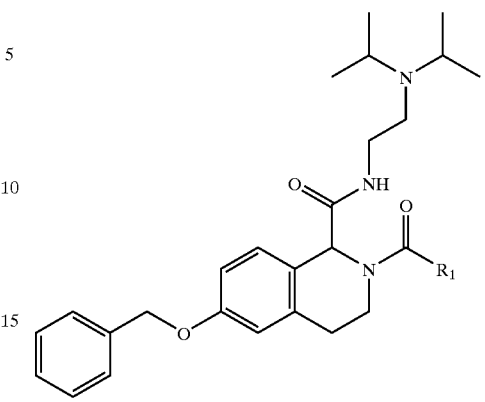

= X₁-R1

| Example No. | X₁-R1 | LC/MS (M + H)+ |
|---|---|---|
| 154 | 2-(4-hydroxy-3,5-dinitrophenyl)ethyl-X₁ | 648 |
| 155 | 3,5-dimethylphenyl-X₁ | 542 |
| 156 | 4-hydroxyphenyl-X₁ | 530 |
| 157 | 2-biphenylyl-X₁ | 590 |
| 158 | 2-benzylphenyl-X₁ | 604 |
| 159 | 2-naphthyl-X₁ | 564 |

-continued
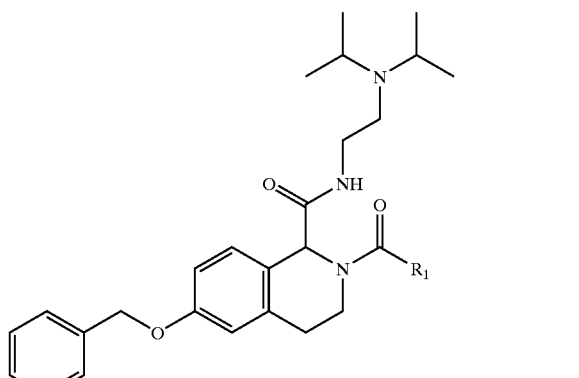
= X₁-R1
| Example No. | X₁-R1 | LC/MS (M + H)+ |
|---|---|---|
| 160 | 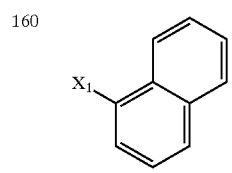 | 564 |
| 161 | 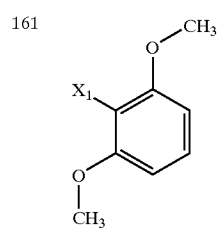 | 574 |
| 162 | 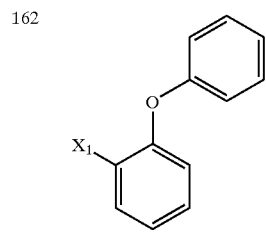 | 606 |
| 163 | 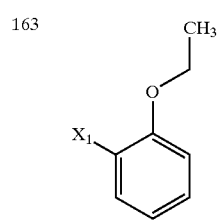 | 558 |
| 164 | 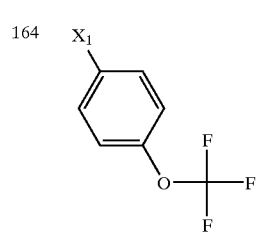 | 598 |
-continued
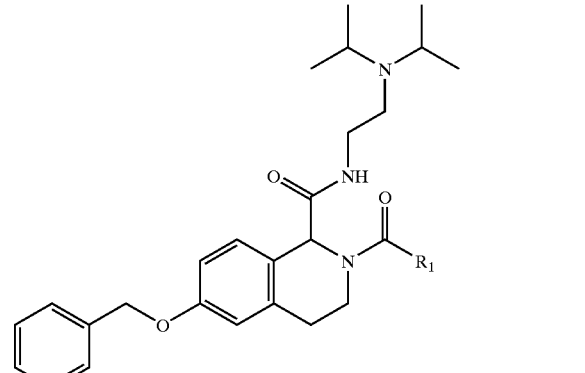
= X₁-R1
| Example No. | X₁-R1 | LC/MS (M + H)+ |
|---|---|---|
| 165 | 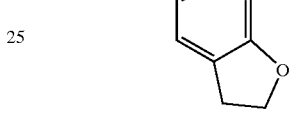 | 556 |
| 166 | 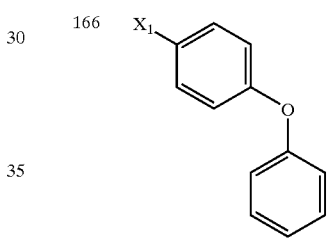 | 606 |
| 167 | 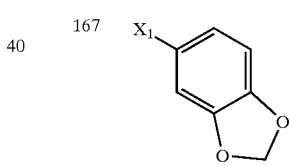 | 558 |
| 168 | 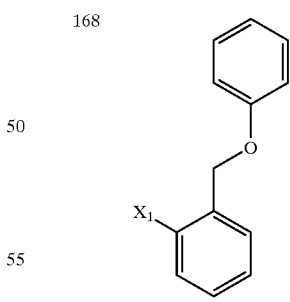 | 620 |
| 169 | 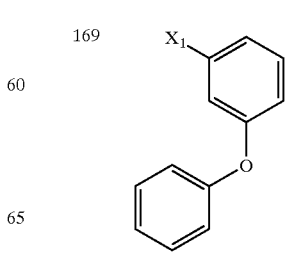 | 606 |

-continued
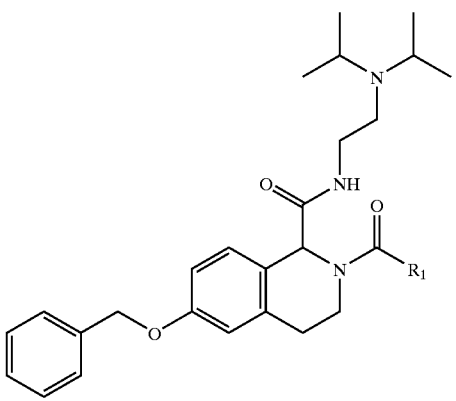
= X₁-R1
| Example No. | X₁-R1 | LC/MS (M + H)+ |
|---|---|---|
| 170 | 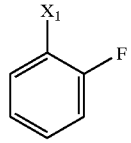 | 532 |
| 171 | 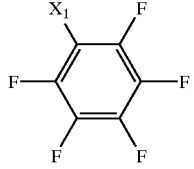 | 604 |
| 172 | 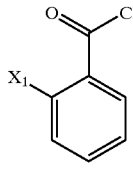 | 556 |
| 173 | 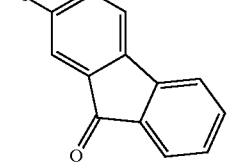 | 616 |
| 174 | 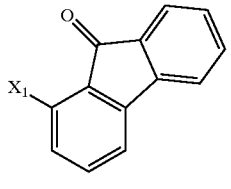 | 616 |
| 175 | 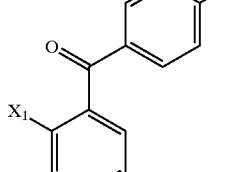 | 636 |
-continued
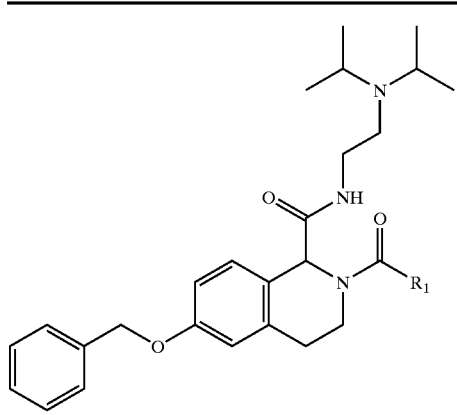
= X₁-R1
| Example No. | X₁-R1 | LC/MS (M + H)+ |
|---|---|---|
| 176 | 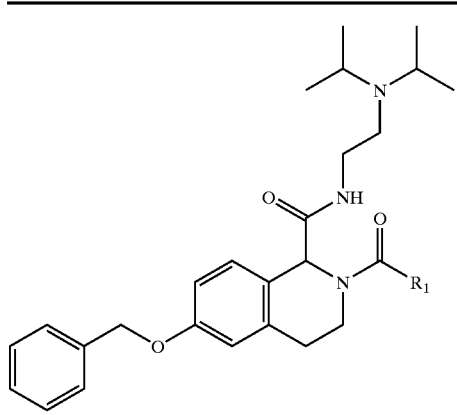 | 652 |
| 177 | 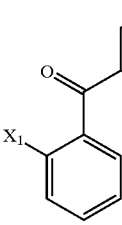 | 571 |
| 178 | 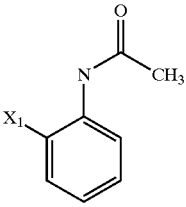 | 571 |
| 179 | 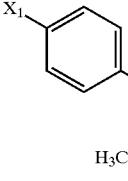 | 610 |
| 180 | 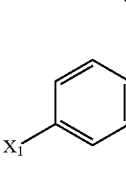 | 628 |

-continued
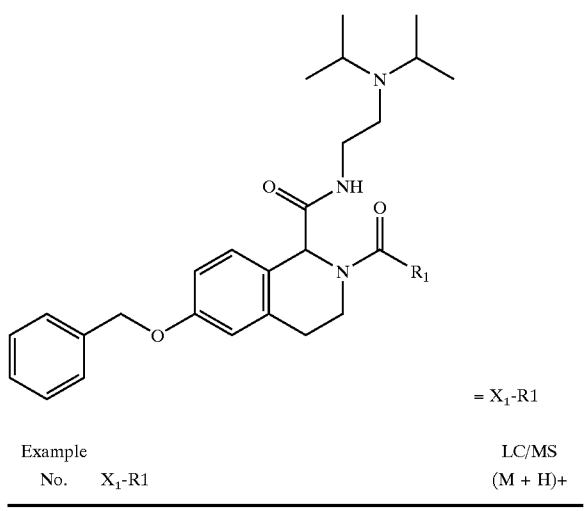
= X₁-R1
| Example No. | X₁-R1 | LC/MS (M + H)+ |
|---|---|---|
| 181 | 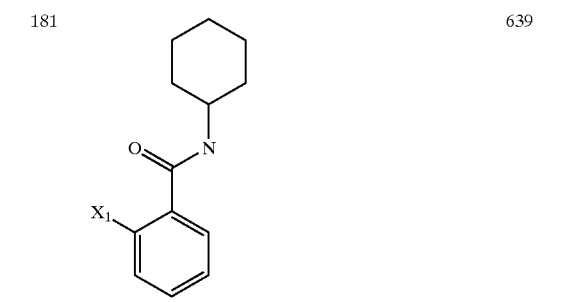 | 639 |
| 182 | 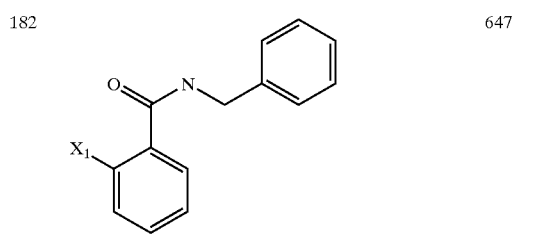 | 647 |
| 183 | 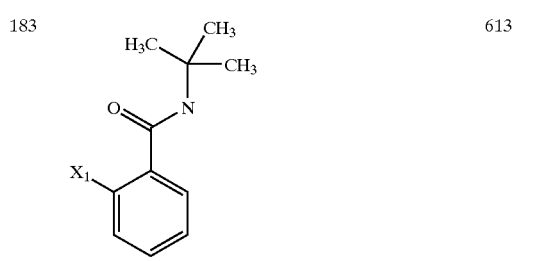 | 613 |
| 184 | 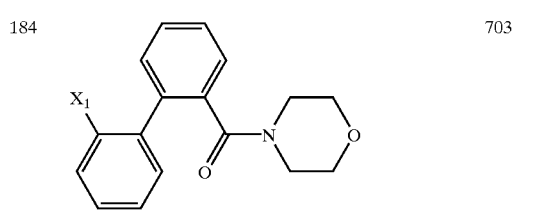 | 703 |
-continued
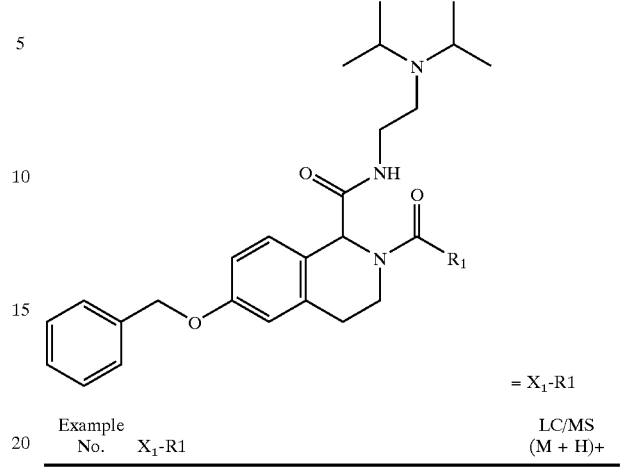
= X₁-R1
| Example No. | X₁-R1 | LC/MS (M + H)+ |
|---|---|---|
| 185 | 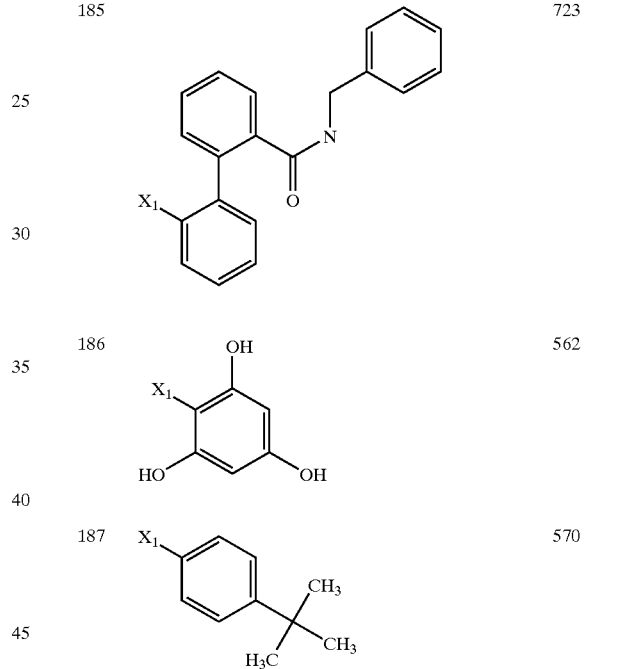 | 723 |
| 186 | | 562 |
| 187 | | 570 |
| 188 | | 539 |
| 189 | | 539 |
| 190 | 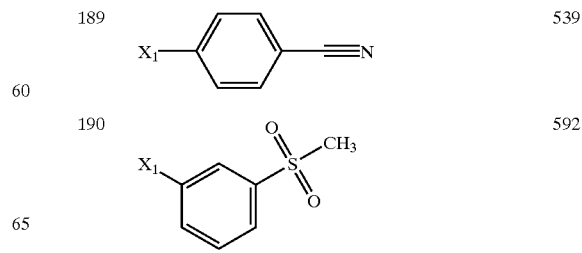 | 592 |

-continued
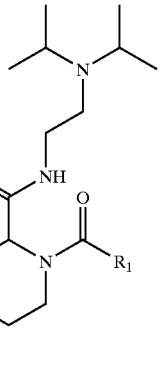
= X₁-R1
| Example No. | X₁-R1 | LC/MS (M + H)+ |
|---|---|---|
| 191 | 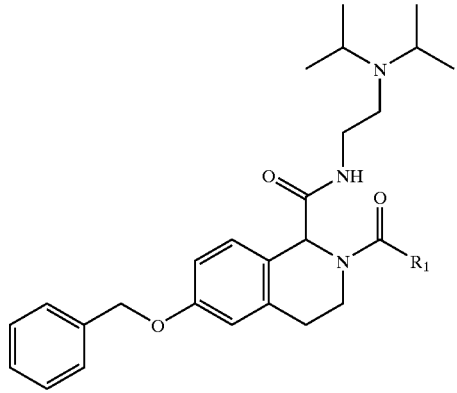 | 592 |
| 192 |  | 593 |
| 193 | 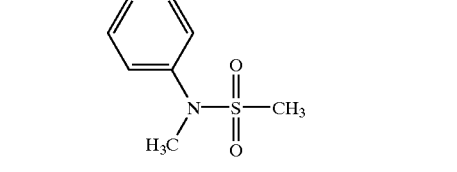 | 627 |
| 194 |  | 683 |
-continued
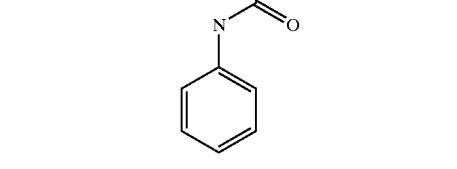
= X₁-R1
| Example No. | X₁-R1 | LC/MS (M + H)+ |
|---|---|---|
| 195 | 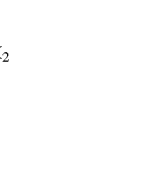 | 621 |
| 196 | 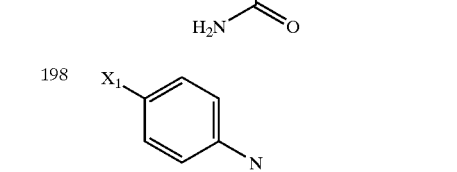 | 648 |
| 197 | | 572 |
| 198 | | 586 |
| 199 | 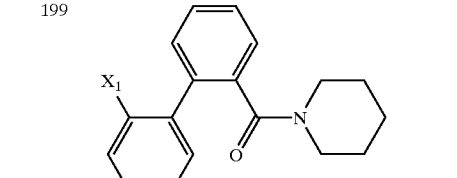 | 701 |

-continued

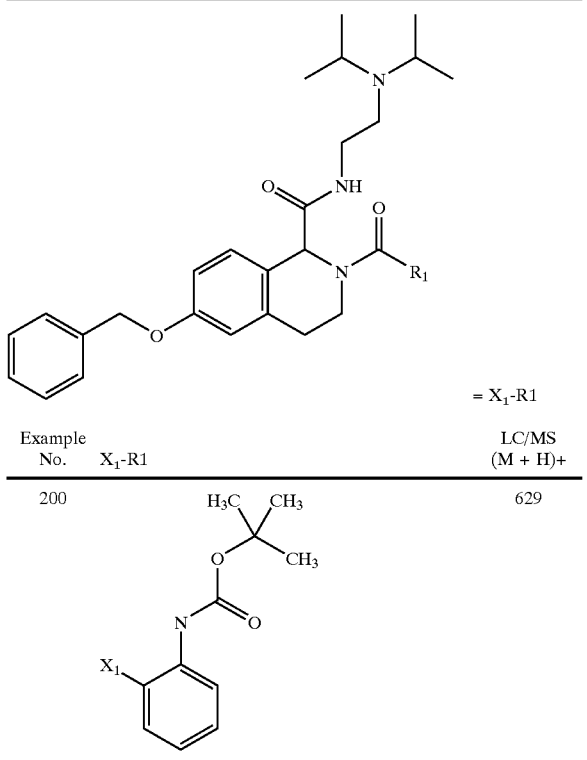

= X₁-R1

| Example No. | X₁-R1 | LC/MS (M + H)+ |
|---|---|---|
| 200 | (structure: H₃C-C(CH₃)(CH₃)-O-C(=O)-N(X₁)-phenyl) | 629 |

EXAMPLE 201

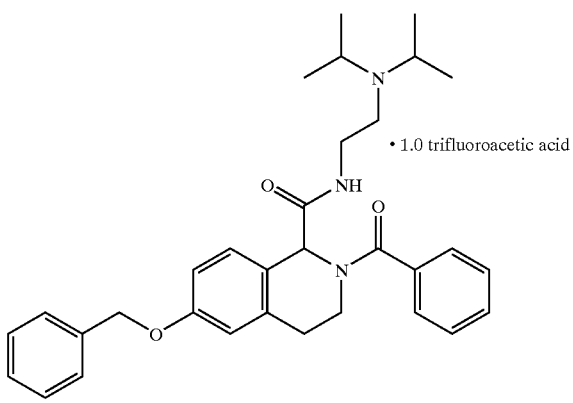

· 1.0 trifluoroacetic acid

To a 0° C. solution of benzoyl chloride (28.1 mg, 0.2 mmol) in dichloromethane (0.5 mL) was added Part A compound from Example 46 (61 mg, 0.15 mmol) followed by triethylamine (27 µL, 0.19 mmol). The reaction mixture was stirred at ambient temperature under nitrogen overnight and then was concentrated. The residue was partitioned between ethyl acetate and water. The two layers were separated, and the ethyl acetate layer was concentrated. Purification by preparative HPLC, eluting with 30–100% B (where A=90% water, 10% methanol, 0.2% trifluoroacetic acid and B=90% methanol, 10% water, 0.2% trifluoroacetic acid), gave the title compound (61.5 mg, 66%) as a pale yellow semi-solid/oil: LC/MS (electrospray, +ions) m/z 514 (M+H).

EXAMPLES 202 TO 214

In a manner analogous to that of Example 201, Examples 202–214 in the table below were prepared from Part A compound from Example 46 and the respective acid chloride, sulfonyl chloride, sulfamoyl chloride.

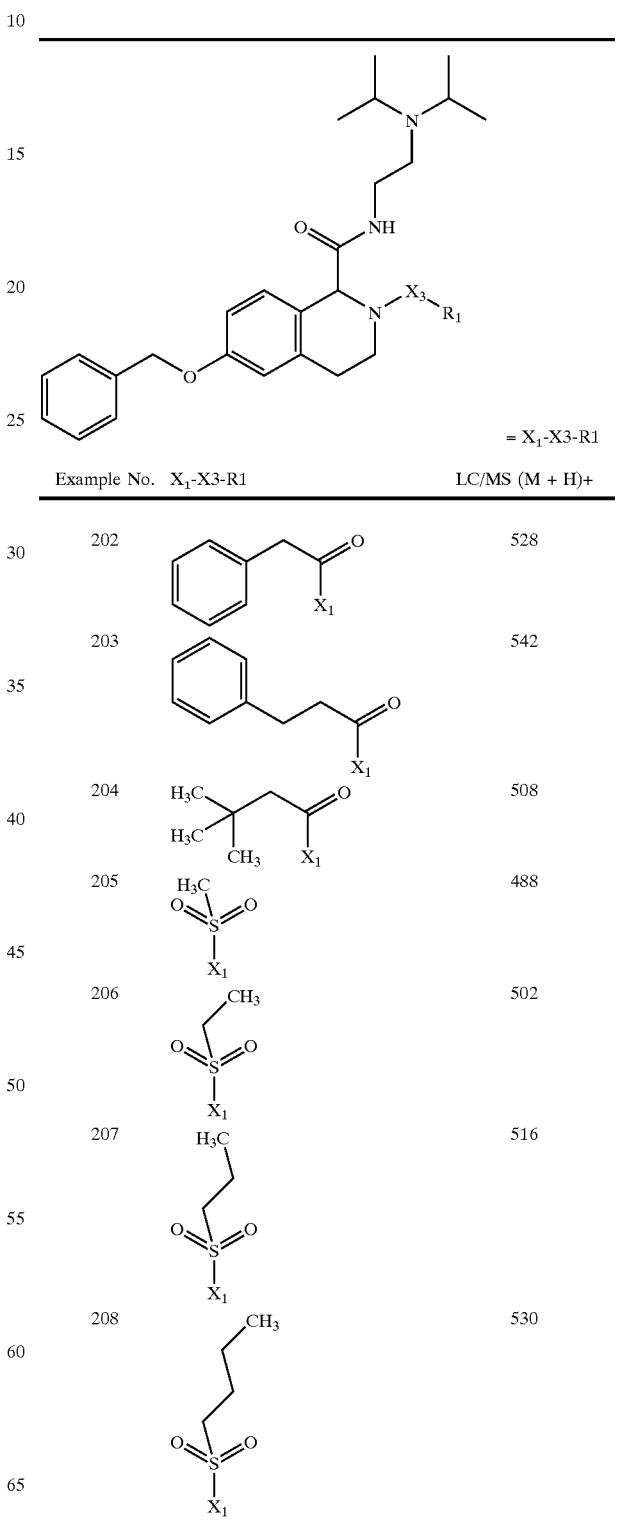

= X₁-X3-R1

| Example No. | X₁-X3-R1 | LC/MS (M + H)+ |
|---|---|---|
| 202 | (PhCH₂-C(=O)-X₁) | 528 |
| 203 | (Ph-CH₂CH₂-C(=O)-X₁) | 542 |
| 204 | (H₃C)₃C-CH₂-C(=O)-X₁ | 508 |
| 205 | H₃C-S(=O)₂-X₁ | 488 |
| 206 | CH₃-CH₂-S(=O)₂-X₁ | 502 |
| 207 | H₃C-CH₂CH₂-S(=O)₂-X₁ | 516 |
| 208 | CH₃-(CH₂)₃-S(=O)₂-X₁ | 530 |

-continued

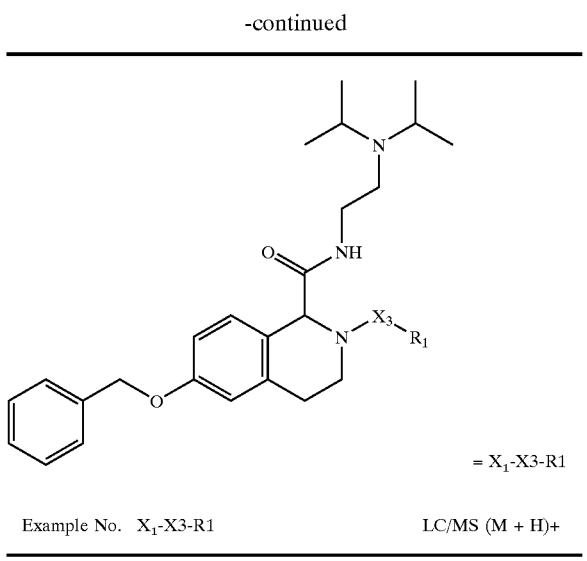

= X₁-X3-R1

| Example No. | X₁-X3-R1 | LC/MS (M + H)+ |
|---|---|---|
| 209 | (phenylsulfonyl-X₁) | 550 |
| 210 | (benzylsulfonyl-X₁) | 564 |
| 211 | (styrylsulfonyl-X₁) | 576 |
| 212 | (thiophene-2-sulfonyl-X₁) | 556 |
| 213 | (H₃C-N(CH₃)-SO₂-X₁) | 517 |

-continued

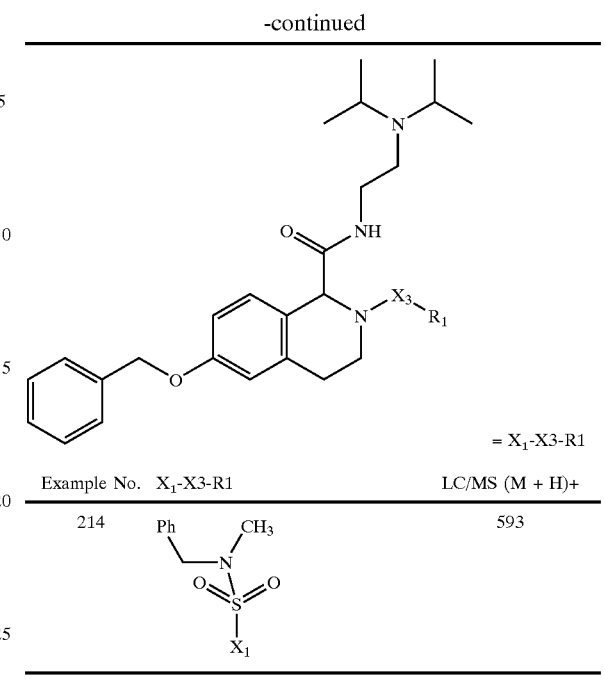

= X₁-X3-R1

| Example No. | X₁-X3-R1 | LC/MS (M + H)+ |
|---|---|---|
| 214 | (Ph-CH₂-N(CH₃)-SO₂-X₁) | 593 |

EXAMPLES 215 TO 229

Examples 215–229 were prepared by methods described in earlier examples and by methods known in the art starting from Part A compound from Example 46 and the corresponding carboxylic acid.

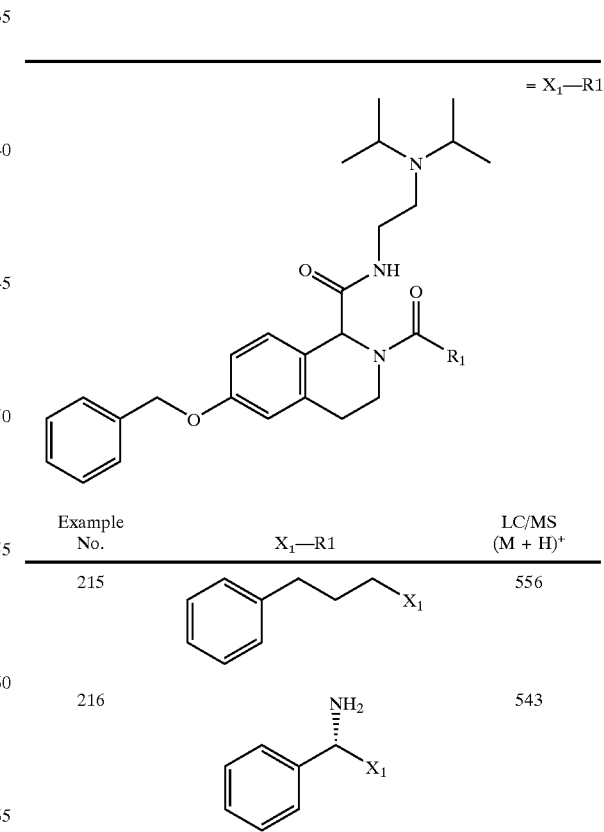

= X₁—R1

| Example No. | X₁—R1 | LC/MS (M + H)⁺ |
|---|---|---|
| 215 | (Ph-CH₂CH₂CH₂-X₁) | 556 |
| 216 | (Ph-CH(NH₂)-X₁) | 543 |

-continued

= X₁—R1

[Structure: 6-benzyloxy-tetrahydroisoquinoline with C1-carboxamide linked to ethyl-N(iPr)₂ and N2-acyl group C(O)-R₁]

| Example No. | X₁—R1 | LC/MS (M + H)⁺ |
|---|---|---|
| 217 | H₃C-C(O)O-CH(Ph)-X₁ | 586 |
| 218 | (CH₃)₃C-O-C(O)-N(CH₃)-CH(Ph)-X₁ | 657 |
| 219 | CH₃-C(O)-NH-CH(Ph)-X₁ | 585 |
| 220 | 3,5-dinitrobenzoyl-NH-CH(Ph)-X₁ | 737 |

-continued

= X₁—R1

[Structure: 6-benzyloxy-tetrahydroisoquinoline with C1-carboxamide linked to ethyl-N(iPr)₂ and N2-acyl group C(O)-R₁]

| Example No. | X₁—R1 | LC/MS (M + H)⁺ |
|---|---|---|
| 221 | PhCH₂-O-C(O)-CH(Ph)-X₁ | 662 |
| 222 | PhCH₂-CH(NH₂)-X₁ | 557 |
| 223 | Ph-CH(NH₂)-X₁ | 543 |
| 224 | Ph-CH(NH₂)-X₁ | 543 |
| 225 | HO-C(O)-CH(Ph)-X₁ | 572 |

EXAMPLE 230

To a solution of Part A compound from Example 46 (61 mg, 0.15 mmol) in dichloromethane (0.5 mL) was added phenyl isocyanate (19.7 mg, 0.165 mmol) via a syringe. Additional dichloromethane (0.5 mL) was added. The reaction mixture was stirred overnight, and then it was concentrated. Purification on preparative HPLC, eluting with a gradient system of 30–100% B (where A=90% water, 10% methanol, 0.2% trifluoroacetic acid and B=90% methanol, 10% water, 0.2% trifluoroacetic acid), gave the title compound (81 mg, 85%) as a white foam: HPLCb rt=3.70 min.; LC/MS (electrospray, +ions) m/z 529 (M+H).

EXAMPLE 231

In a manner analogous to that of Example 230, the title compound was prepared from Part A compound from Example 46 (61 mg, 0.15 mmol) and tert-butyl isocyanate (16.4 mg, 0.165 mmol) in a yield of 69.5 mg (75%) as a white semi-solid/oil: HPLCb rt=3.71 min.; LC/MS (electrospray, +ions) m/z 509 (M+H).

| Example No. | $X_1$—R1 | LC/MS $(M+H)^+$ |
|---|---|---|
| 226 | phenyl-CH(OH)(C=O)-$X_1$ | 572 |
| 227 Isomer A | Ph-CH($X_1$)-CH$_2$-C(=O)-Me | 584 |
| 228 Isomer B | Ph-CH($X_1$)-CH$_2$-C(=O)-Me | 584 |
| 229 | Me$_2$N-SO$_2$-NH-CH(Ph)-$X_1$ | 650 |

EXAMPLE 232

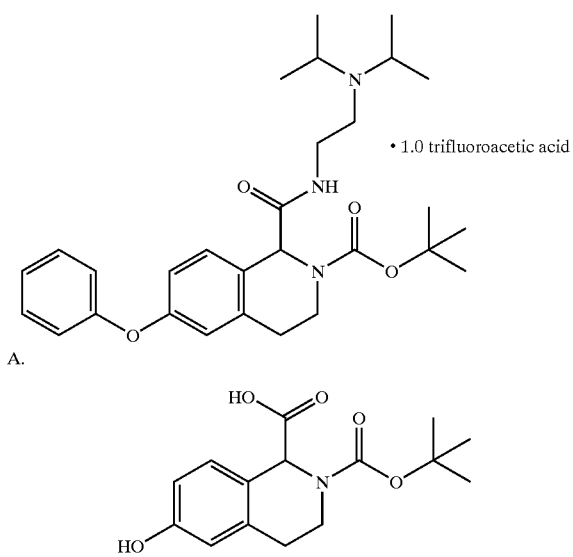

A.

To a solution of Part C compound from Example 1 (1.00 g, 3.25 mmol) in methanol (1 mL) and tetrahydrofuran (1 mL) was added a solution of sodium hydroxide (260 mg, 6.5 mmol) in water (650 μL). The reaction was stirred overnight at ambient temperature, heated at 60° C. for 6 h and then stirred at ambient temperature overnight. The solvent was removed in vacuo, and the residue was partitioned between water and ethyl acetate. The aqueous layer was separated and acidified with 6 N hydrochloric acid solution to pH ~3 and extracted with ethyl acetate (2×) The organic layers were dried over sodium sulfate and the mixture was filtered. The filtrate was concentrated to give the title compound (930 mg, 97.5%) as a clear oil, which became a white foam.

B.

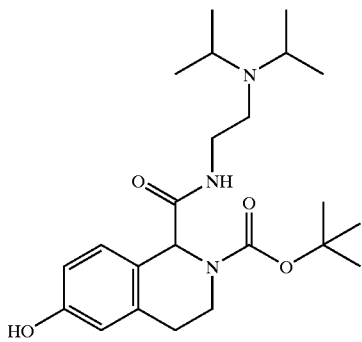

To a solution of Part A compound (500 mg, 1.7 mmol) and diisopropylethylenediamine (326 μL, 1.9 mmol) in dimethylformamide (10 mL) was added diisopropylethylamine (890 μL, 5.1 mmol) followed by 1-hydroxy-7-azabenzotriazole (325 mg, 2.4 mmol) and 1-(3-dimethylaminopropyl)-3-ethylcarbodiimide hydrochloride (327 mg, 1.7 mmol). After stirring the reaction mixture overnight, the mixture was partitioned between ethyl acetate and saturated aqueous sodium bicarbonate solution. The organic layer was washed with water (2×) and brine, and then dried over sodium sulfate. The mixture was filtered and the filtrate concentrated in vacuo to give the title product (587 mg, 82.1%) as a white foam.

C.

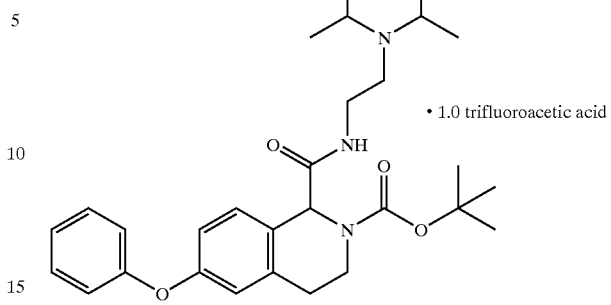

To a slurry of Part B compound (50 mg, 0.12 mmol), phenyl boronic acid (29 mg, 0.24 mmol), copper(II) acetate (22 mg, 0.12 mmol) and 4 Å powdered molecular sieves in dichloromethane (1.2 mL) was added pyridine (48 μL, 0.60 mmol). The reaction was stirred overnight and then was filtered. The filtrate was concentrated to a green oil that was purified by preparative HPLC. The title compound (59 mg, 81%) was obtained as a yellow oil: HPLCa1 rt=2.2 min.; LC/MS (electrospray, +ions) m/z 496 (M+H).

EXAMPLE 233

Isomer A and Isomer B

A.

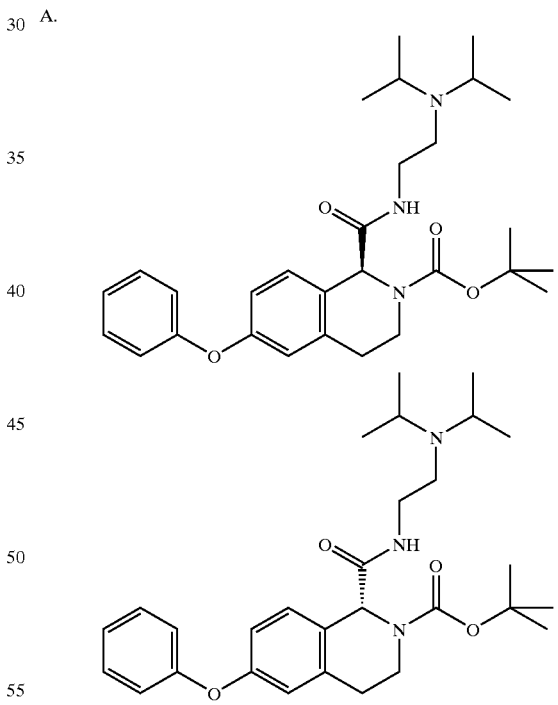

Title compound, Example 232 (70 mg) was resolved on Chiralpak AD column (50×500 mm), eluting with 20% isopropanol/hexanes to give the title compounds, Isomer A (28 mg) and Isomer B (30 mg).

EXAMPLES 234 TO 245

In a manner analogous to that of Example 232, Examples 234–245 compounds listed in the table below were prepared from Part B compound from Example 232 (0.12 mmol) and the respective phenylboronic acid (0.24 mmol). A few compounds were purified by preparative HPLC, eluting with a gradient system of methanol and water with 0.2% trifluoroacetic acid. These compounds were isolated as trifluoroacetic acid salts.

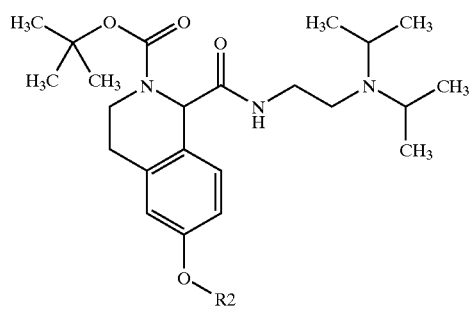

| Example No. | X₁-R2 | LC/MS (M + H)+ |
|---|---|---|
| 234 | X₁—⟨C₆H₄⟩—Cl (4-Cl) | 531 |
| 235 | X₁—⟨C₆H₄⟩—CF₃ (4-CF₃) | 564 |
| 236 | X₁—⟨C₆H₄⟩—NO₂ (3-NO₂) | 541 |
| 237 | X₁—⟨C₆H₄⟩—OCH₃ (4-OCH₃) | 526 |
| 238 | X₁—⟨C₆H₃⟩—(3,5-Cl₂) | 565 |
| 239 | X₁—⟨C₆H₄⟩—SCH₃ (4-SCH₃) | 542 |
| 240 | X₁—⟨C₆H₄⟩—CHO (4-CHO) | 524 |
| 241 | X₁—⟨C₆H₄⟩—CHO (3-CHO) | 524 |
| 242 | X₁—⟨C₆H₄⟩—OCH₃ (3-OCH₃) | 526 |

-continued

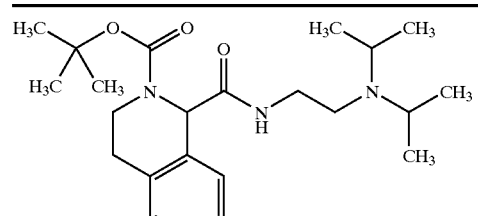

| Example No. | X₁-R2 | LC/MS (M + H)+ |
|---|---|---|
| 243 | 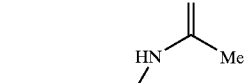 (3-NHC(O)Me) | 553 |
| 244 | 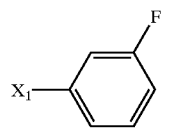 (3-F) | 514 |
| 245 | 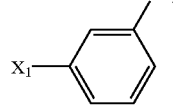 (3-CF₃) | 564 |

EXAMPLE 246

A.

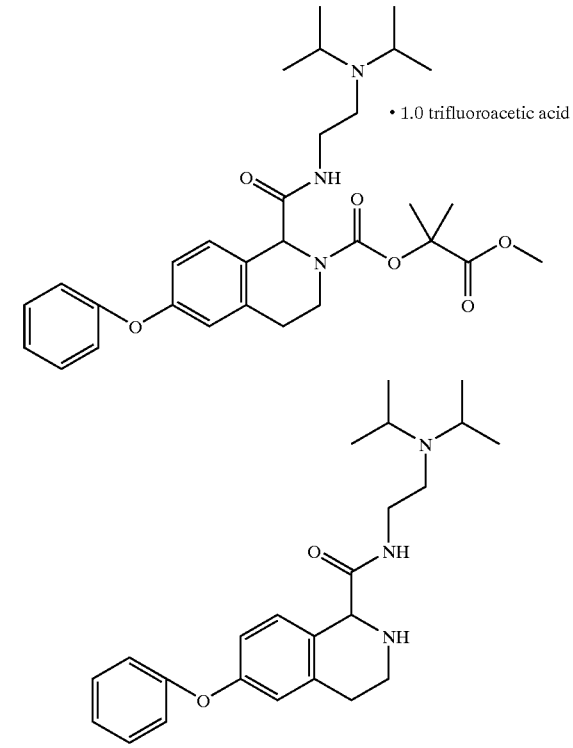

• 1.0 trifluoroacetic acid

To neat title compound from Example 232 (1.56 g, 3.15 mmol) is added 4N hydrogen chloride (7 mL, dioxane solution) at room temperature. After 3 h, the volatiles were removed in vacuo, the residue redissolved in ethyl acetate and the pH adjusted to 8 with 1N sodium hydroxide. The organic layer was dried and concentrated to give the title compound (1.11 g) as a yellow colored oil. LC/MS (electrospray, +ions) m/z 396(M+H).

B.

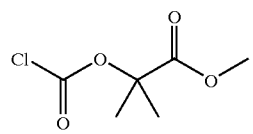

To a 0° C. solution of methyl 2-hydroxyisobutyrate (236 mg, 2.0 mmol) and triethylamine (202 mg, 2.0 mmol) in tetrahydrofuran (5 mL) was added 1.9 M phosgene in toluene (1.68 mL, 3.2 mmol). After stirring for 2 h between −5 to 0° C., the reaction mixture was concentrated and used in the next procedure without purification.

C.

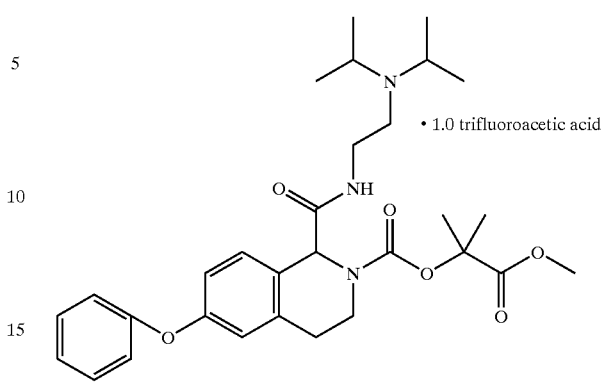

At 0° C., a solution of Part B compound (2.0 mmol) in dichloromethane (5 mL) was treated with Part A compound (118.9 mg, 0.30 mmol) followed by triethylamine (101.2 mg, 1.0 mmol). The reaction mixture was stirred at 0° C. to 5° C. for 2 h and then concentrated. Purification by preparative HPLC, eluting with a gradient system of 40–100% B (where A=90% water, 10% methanol, 0.2% trifluoroacetic acid and B=90% methanol, 10% water, 0.2% trifluoroacetic acid), gave the title compound (115.8 mg) as a yellow oil; LC/MS (electrospray, +ions) m/z 540(M+H).

EXAMPLES 247 TO 250

Examples 247–250 listed below can were prepared as shown in Scheme 11 and employing the procedures described above, the working examples, and methods known in the arts.

| Example No. | Structure | LC/MS (M + H)+ |
|---|---|---|
| 247 | 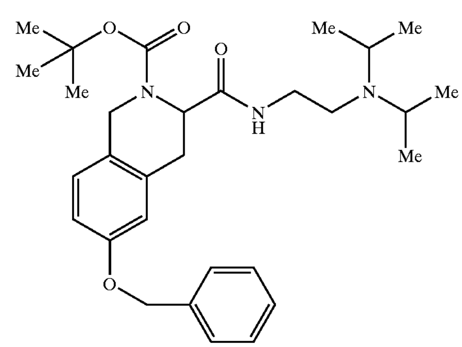 | 510 |
| 248 | 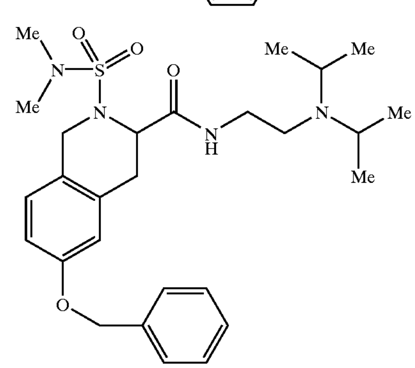 | 517 |

-continued

| Example No. | Structure | LC/MS (M + H)+ |
|---|---|---|
| 249 | [structure] | 503 |

Examples listed below can be prepared from intermediate Part A compound from Example 46 and an alkyl halide:

| Example No. | Structure | LC/MS (M + H)+ |
|---|---|---|
| 250 | [structure] | 524 |

Example listed in the Table below can be prepared employing the procedures described above, the working examples, and methods known in the arts.

| Example No. | Structure | LC/MS (M + H)+ |
|---|---|---|
| 251 | [structure] | 552 |

-continued

| Example No. | Structure | LC/MS (M + H)+ |
|---|---|---|
| 252 | 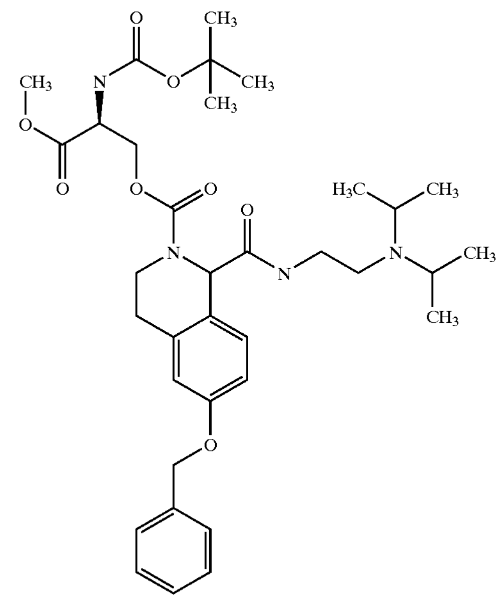 | 655 |
| 253 | 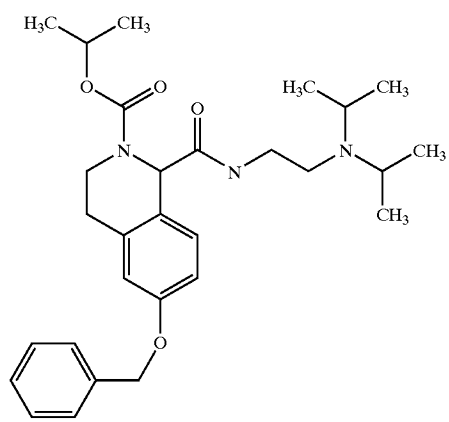 | 496 |
| 254 | 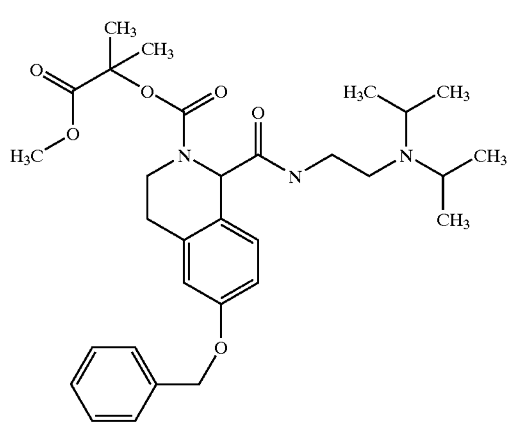 | 554 |

-continued

| Example No. | Structure | LC/MS (M + H)+ |
|---|---|---|
| 255 | 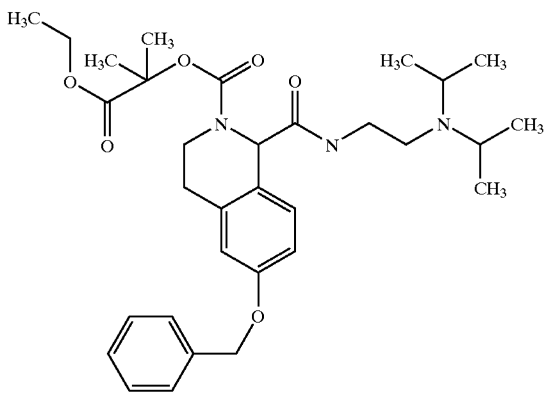 | 568 |
| 256 | 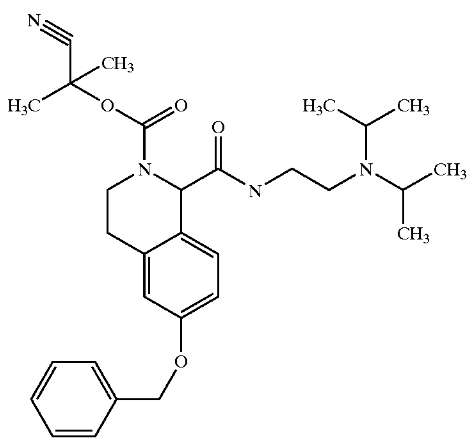 | 521 |
| 257 | 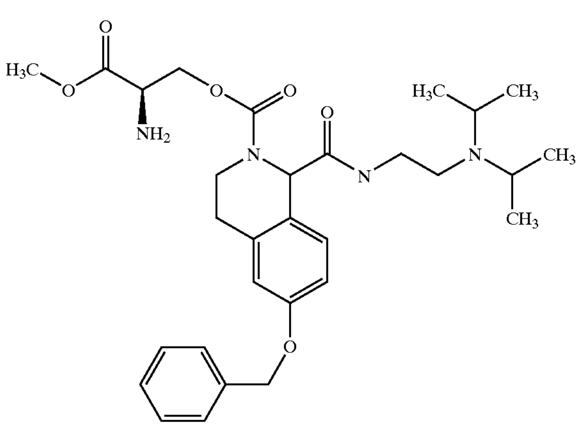 | 555 |

-continued

| Example No. | Structure | LC/MS (M + H)+ |
|---|---|---|
| 258 Isomer A | 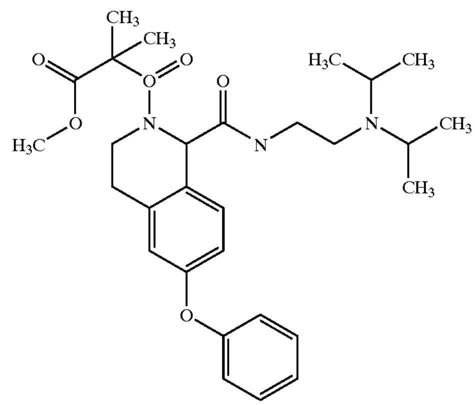 | 540 |
| 259 Isomer B | 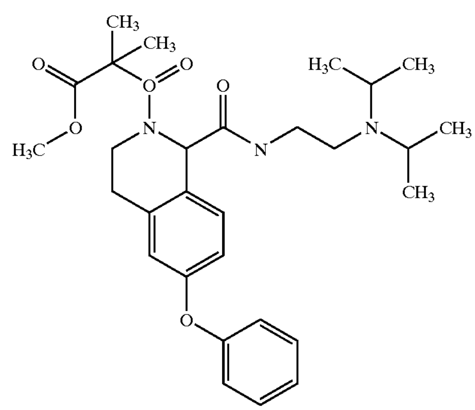 | 540 |
| 260 | 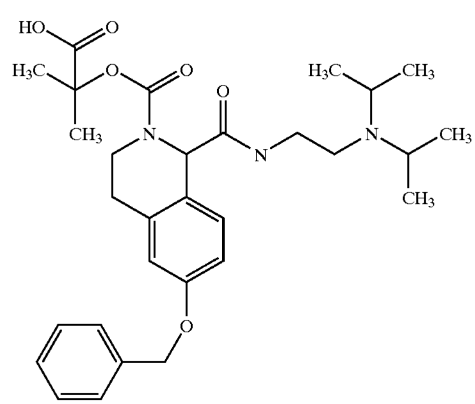 | 540 |

-continued

| Example No. | Structure | LC/MS (M + H)⁺ |
|---|---|---|
| 261 | 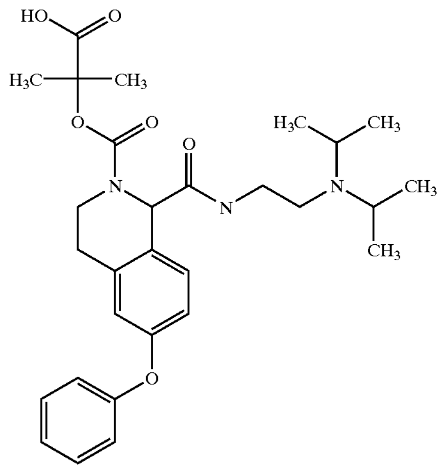 | 526 |
| 262 | 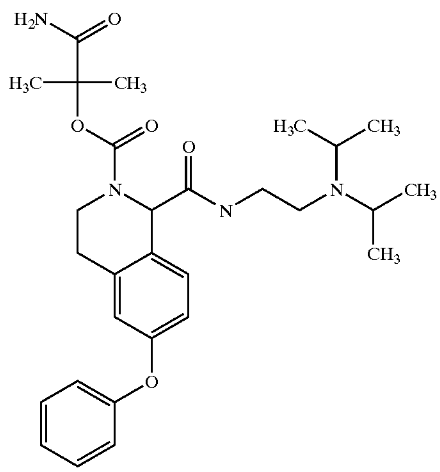 | 525 |
| 263 | 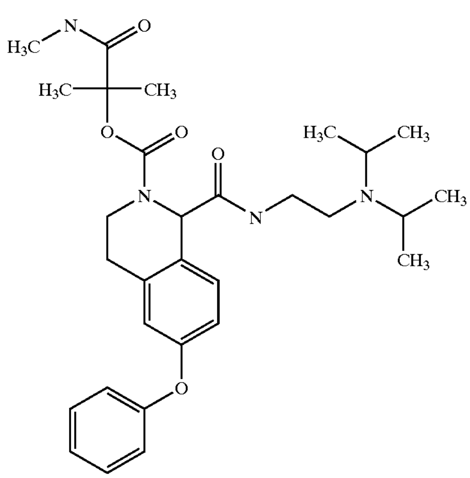 | 539 |

-continued
| Example No. | Structure | LC/MS (M + H)+ |
|---|---|---|
| 264 | 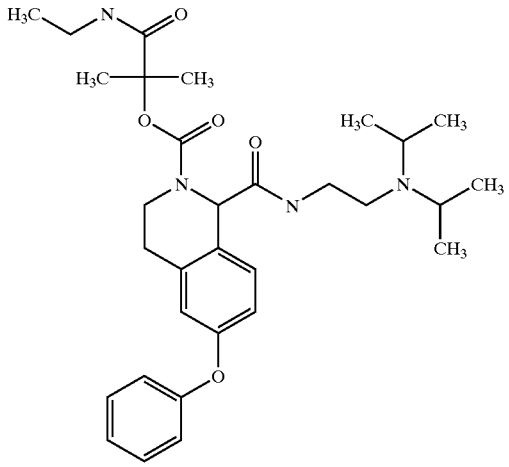 | 553 |
| 265 | 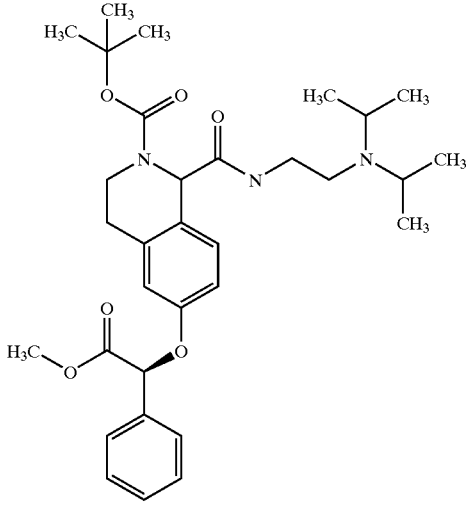 | 568 |
| 266 Diastereomer A | 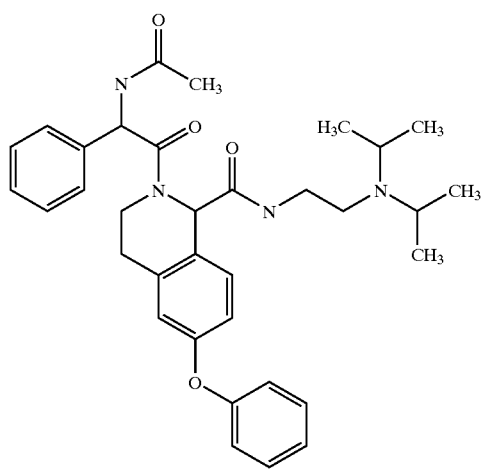 | 571 |

-continued
| Example No. | Structure | LC/MS (M + H)+ |
|---|---|---|
| 267 Diastereomer B | 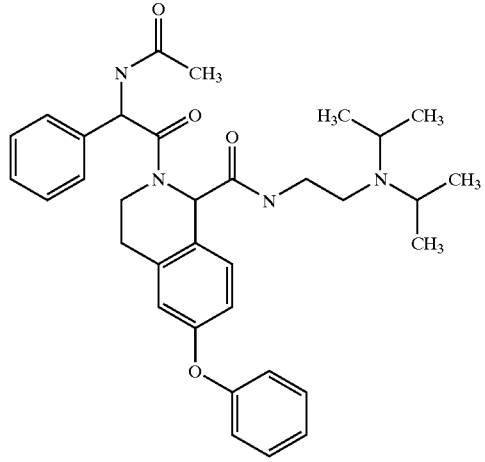 | 571 |
| 268 Diastereomer A | 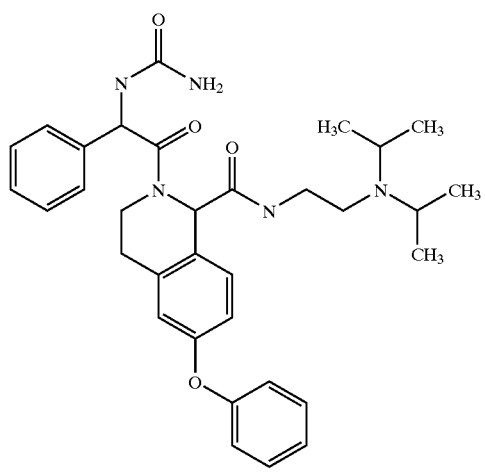 | 572 |
| 269 Diastereomer B | 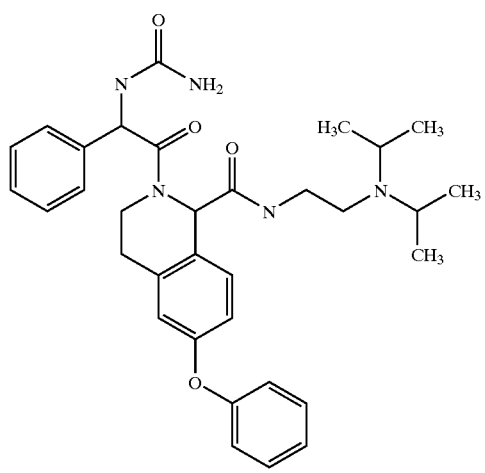 | 572 |

| Example No. | Structure | LC/MS (M + H)+ |
|---|---|---|
| 270 Diastereomer A | 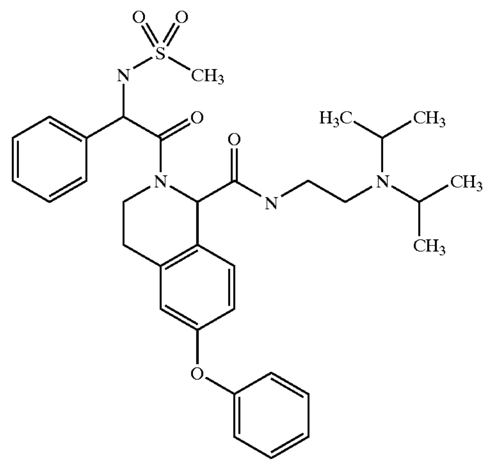 | 607 |
| 271 Diastereomer B | 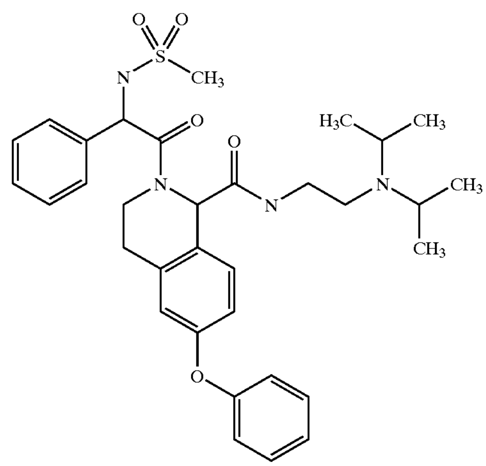 | 607 |
| 272 Diastereomer A | 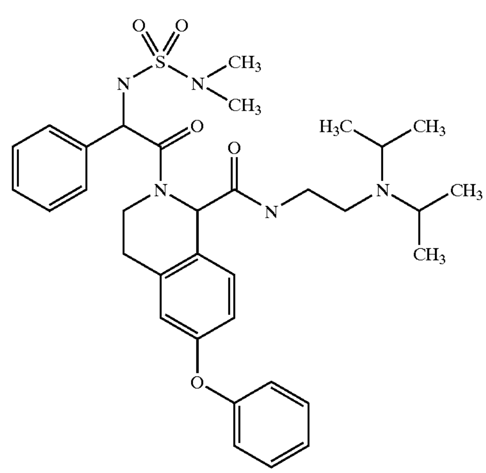 | 636 |

-continued
| Example No. | Structure | LC/MS (M + H)+ |
|---|---|---|
| 273 Diastereomer B | 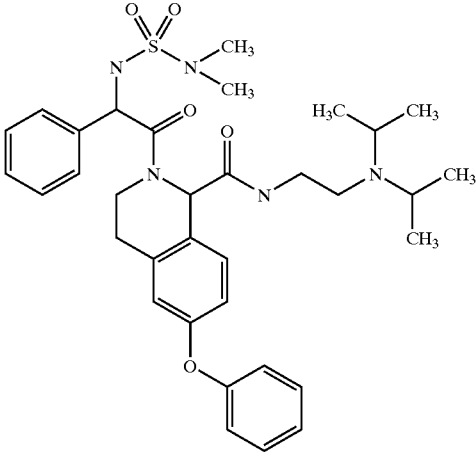 | 636 |
| 274 Diastereomer A | 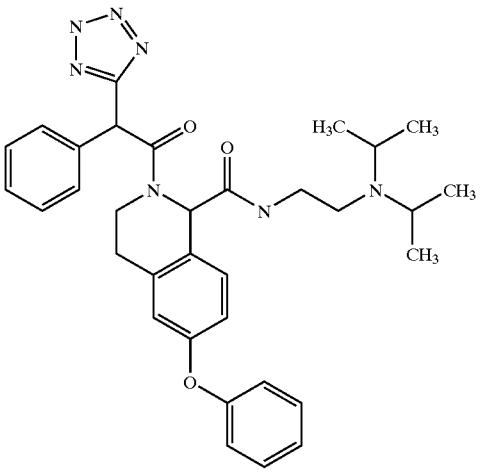 | 582 |
| 275 Diastereomer B | 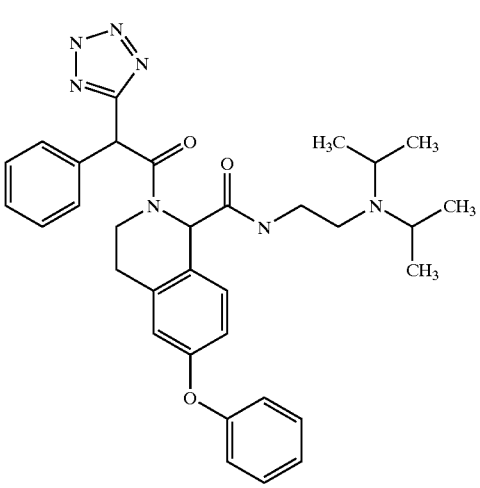 | 582 |

-continued
| Example No. | Structure | LC/MS (M + H)+ |
|---|---|---|
| 276 Diastereomer A | 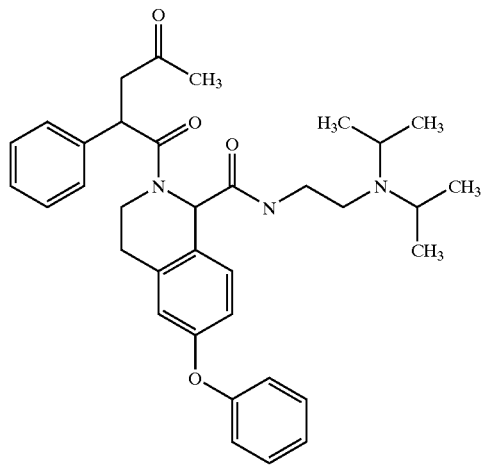 | 570 |
| 277 Diastereomer B | 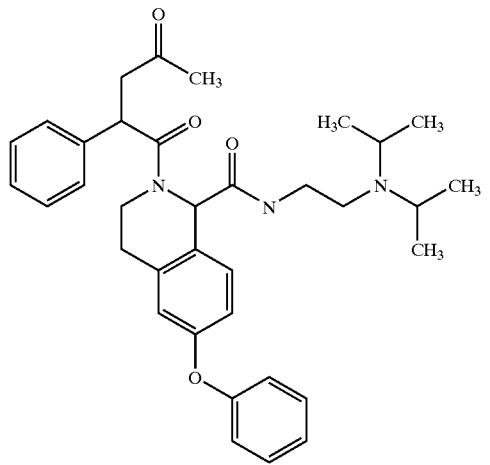 | 570 |
| 278 Diastereomer A | 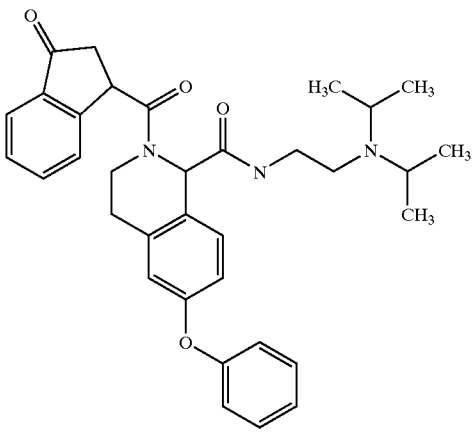 | 554 |

-continued
| Example No. | Structure | LC/MS (M + H)+ |
|---|---|---|
| 279 Diastereomer B | 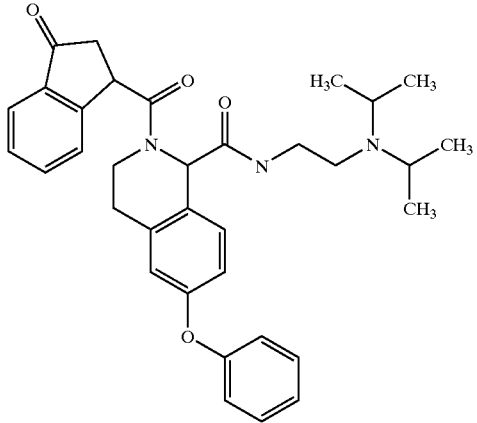 | 554 |
| 280 Isomer A | 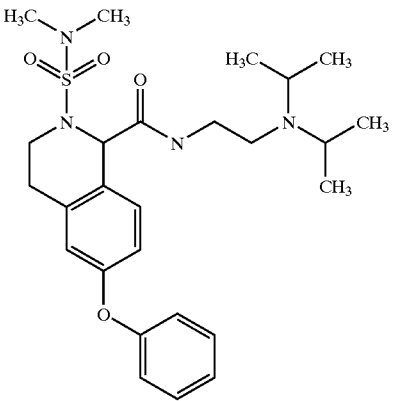 | 503 |
| 281 Isomer B | 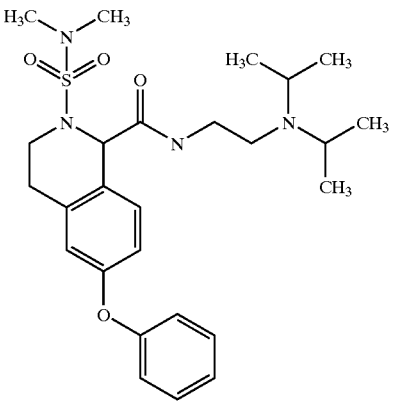 | 503 |

-continued

| Example No. | Structure | LC/MS (M + H)+ |
|---|---|---|
| 282 | 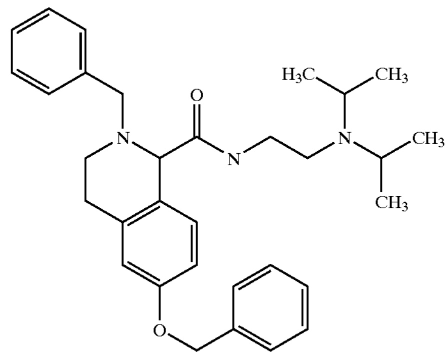 | 500 |
| 283 | 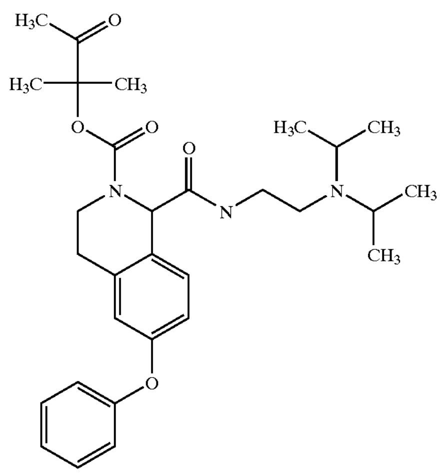 | 524 |
| 284 | 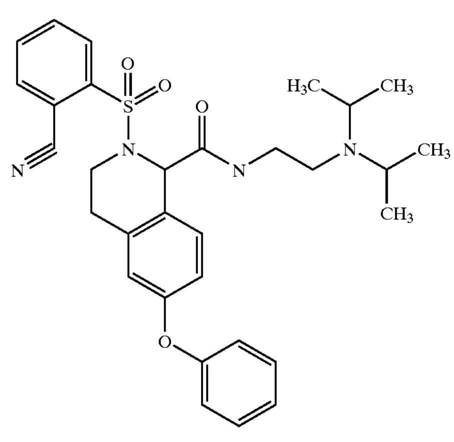 | 561 |

-continued

| Example No. | Structure | LC/MS (M + H)+ |
|---|---|---|
| 285 | 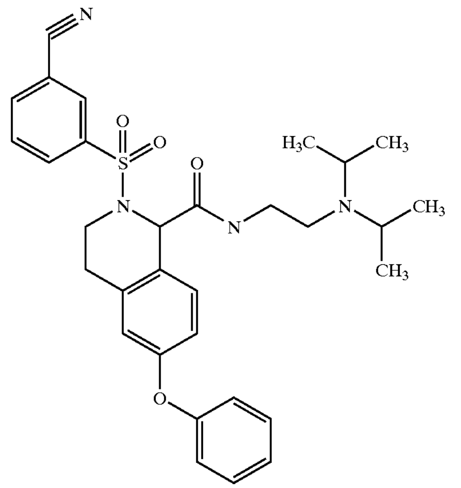 | 561 |
| 286 | 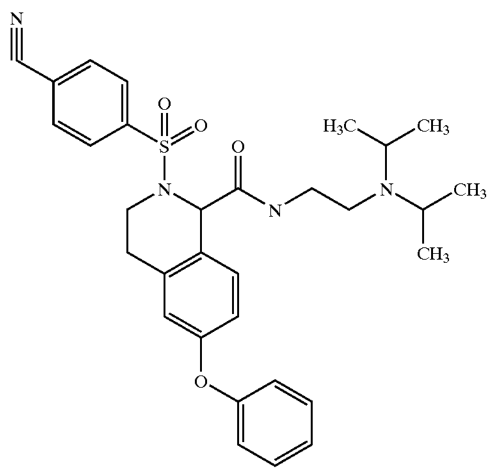 | 561 |
| 287 | 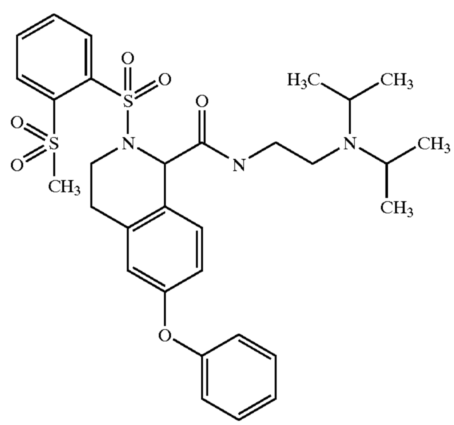 | 614 |

-continued
| Example No. | Structure | LC/MS (M + H)+ |
|---|---|---|
| 288 | 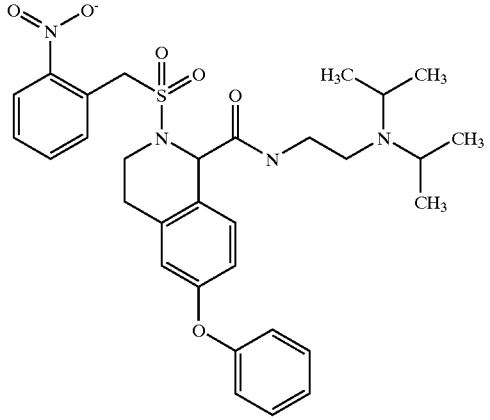 | 595 |
| 289 | 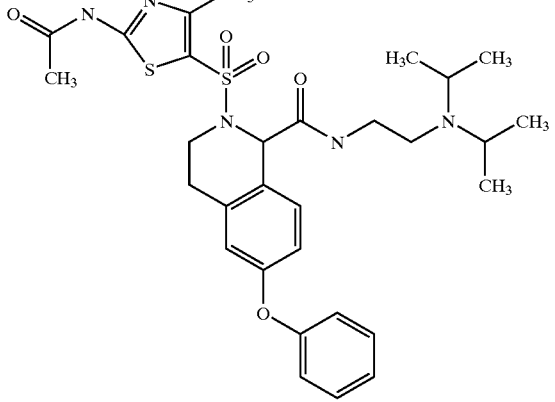 | 614 |
| 290 | 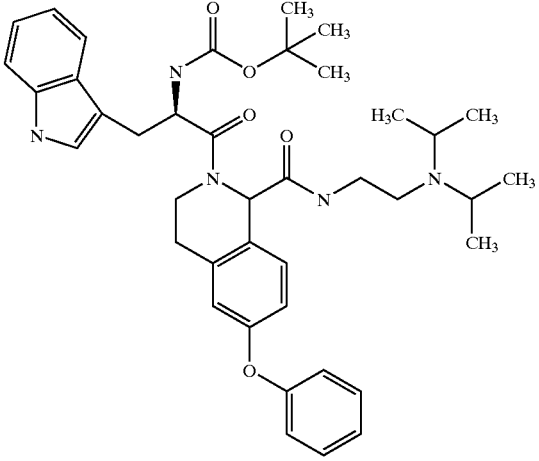<br>Chiral | 682 |

-continued
| Example No. | Structure | LC/MS (M + H)+ |
|---|---|---|
| 291 | 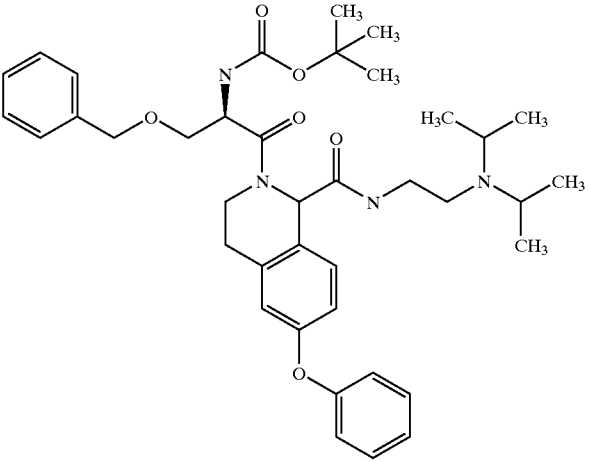<br>Chiral | 673 |
| 292 | 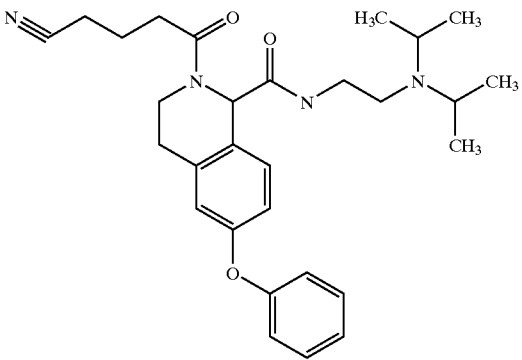<br>Chiral | 491 |
| 293 | 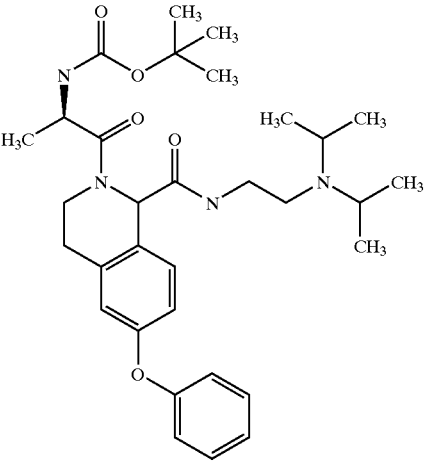<br>Chiral | 567 |

| Example No. | Structure | LC/MS (M + H)+ |
|---|---|---|
| 294 | 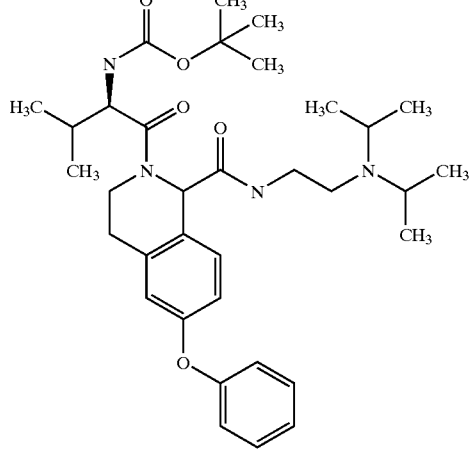 Chiral | 595 |
| 295 | 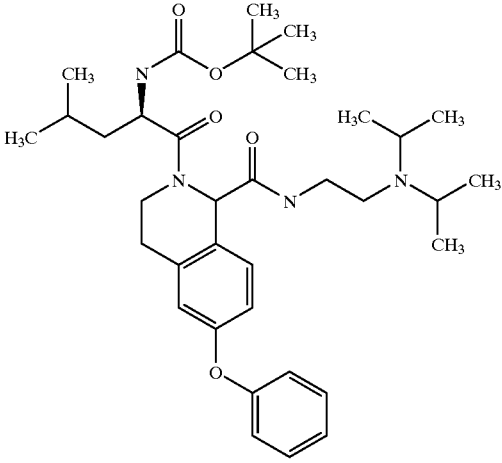 Chiral | 609 |
| 296 | 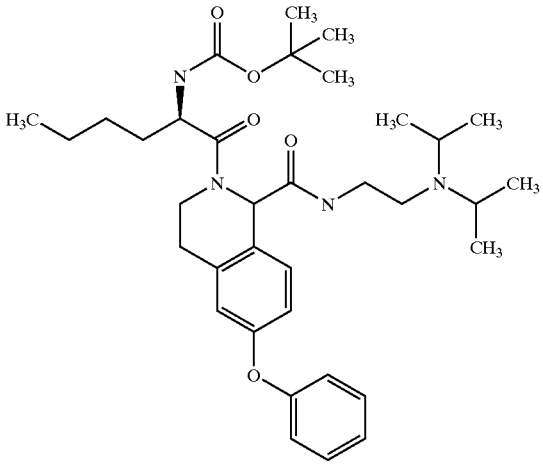 Chiral | 609 |

| Example No. | Structure | LC/MS (M + H)+ |
|---|---|---|
| 297 | 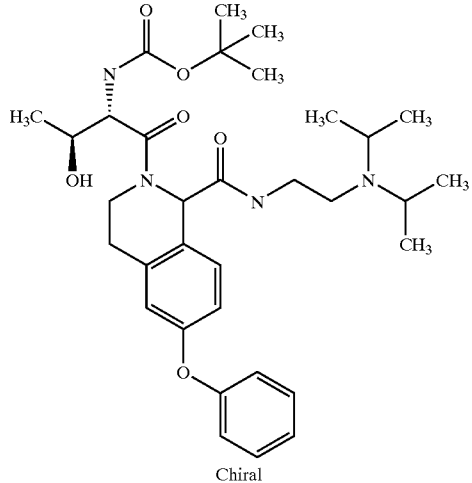 | 597 |
| 298 | 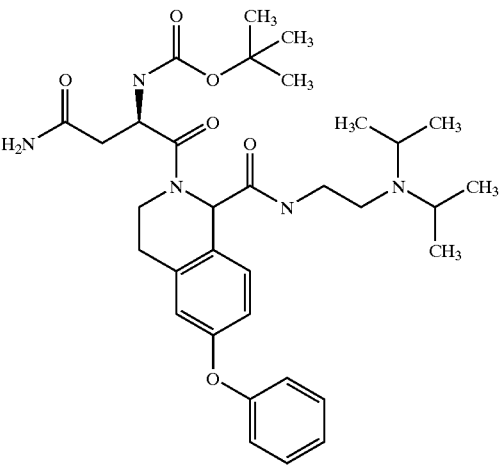 | 610 |
| 299 | 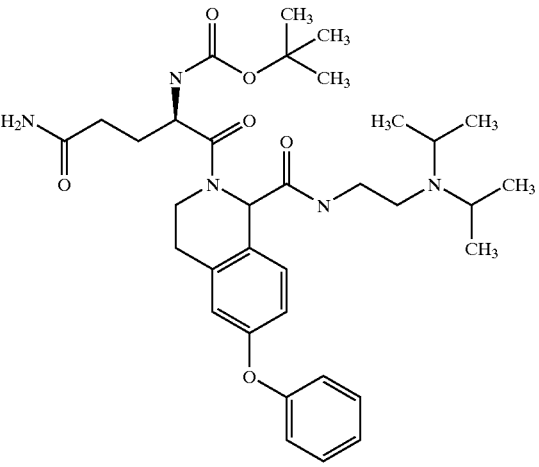 | 624 |

-continued
| Example No. | Structure | LC/MS (M + H)+ |
|---|---|---|
| 300 | 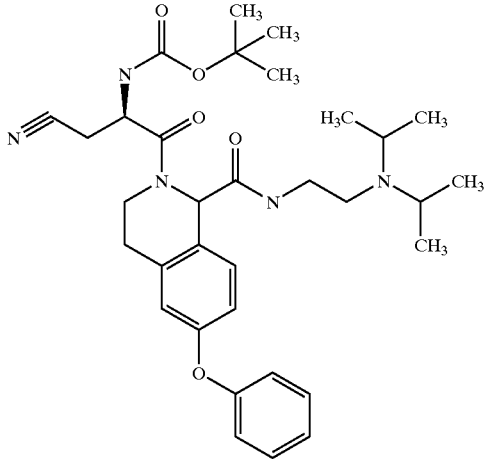<br>Chiral | 592 |
| 301 | 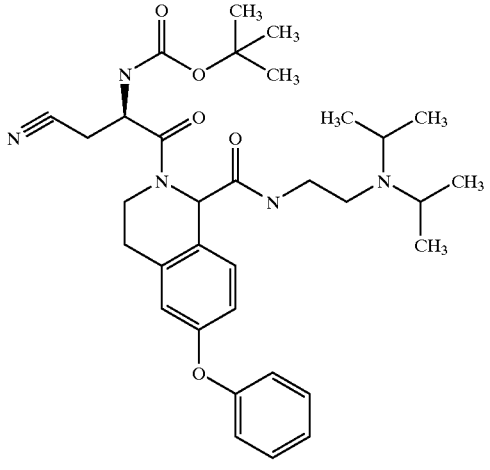<br>Chiral | 592 |
| 302 | 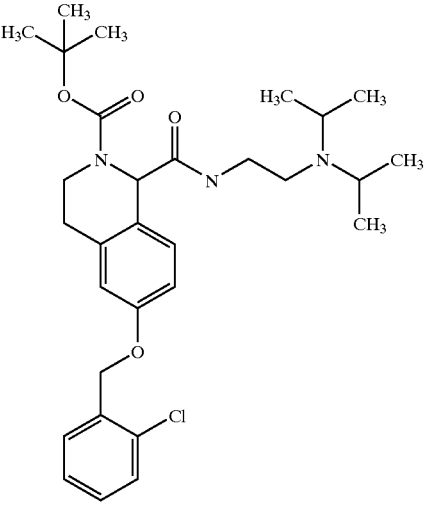 | 545 |

-continued
| Example No. | Structure | LC/MS (M + H)+ |
|---|---|---|
| 303 | 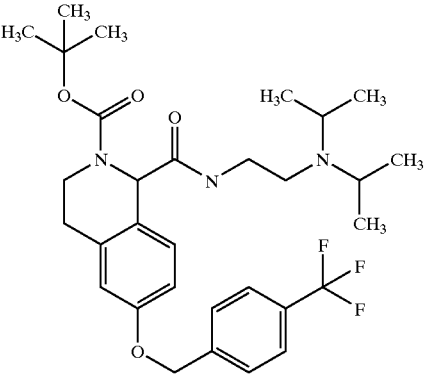 | 578 |
| 304 | 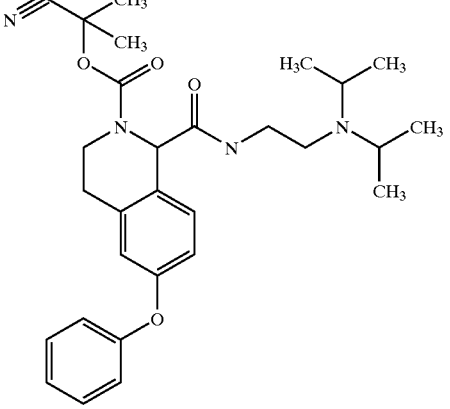 | 507 |
| 305 | 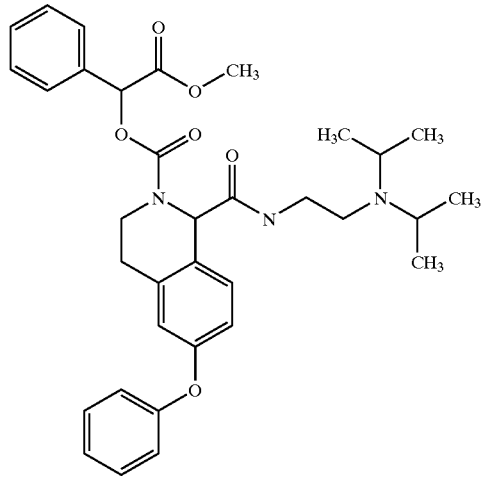 | 588 |

-continued

| Example No. | Structure | LC/MS (M + H)+ |
|---|---|---|
| 306 | 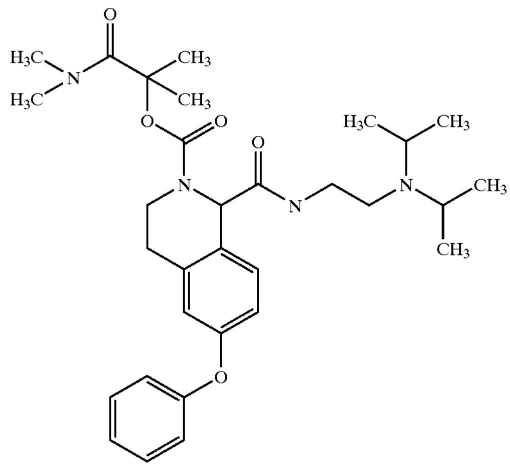 | 553 |
| 307 | 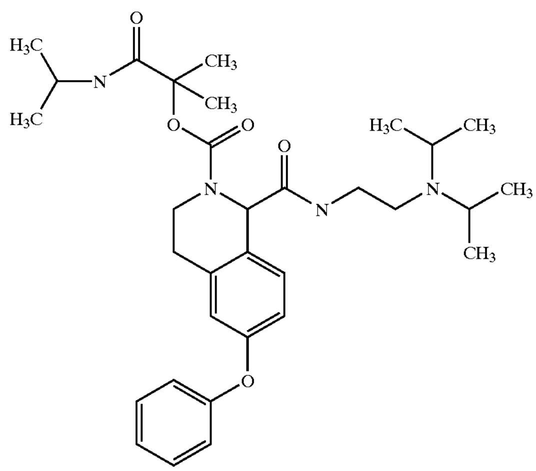 | 567 |
| 308 | 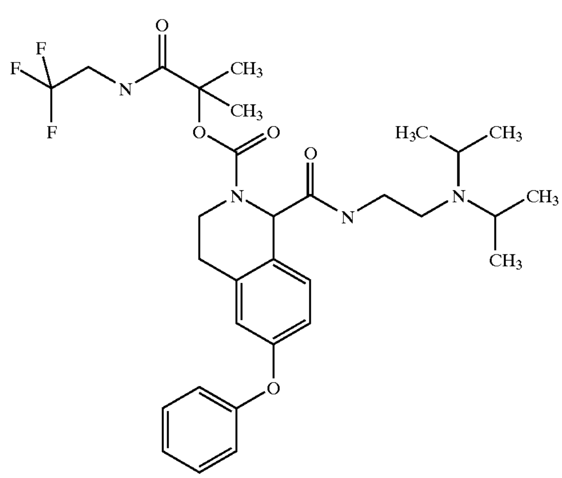 | 607 |

-continued

| Example No. | Structure | LC/MS (M + H)+ |
|---|---|---|
| 309 | 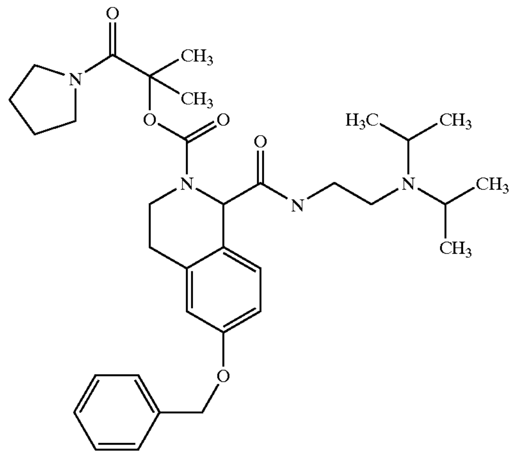 | 593 |
| 310 | 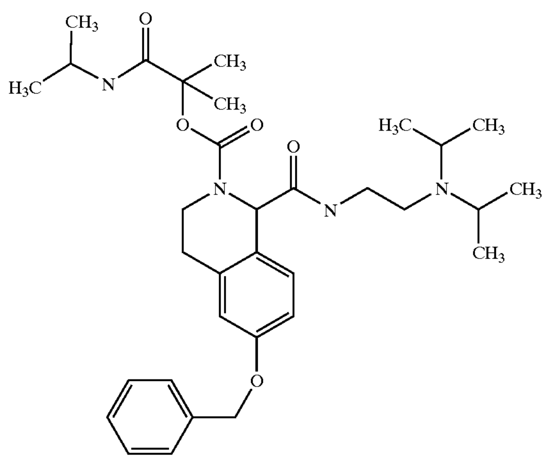 | 581 |
| 311 | 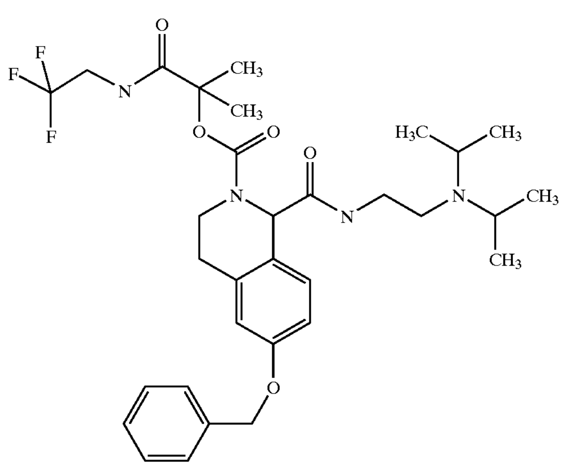 | 621 |

-continued

| Example No. | Structure | LC/MS (M + H)+ |
|---|---|---|
| 312 | 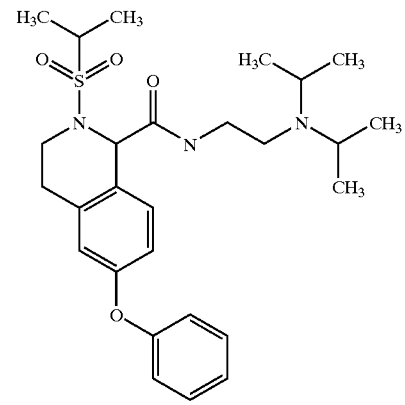 | 502 |
| 313 | 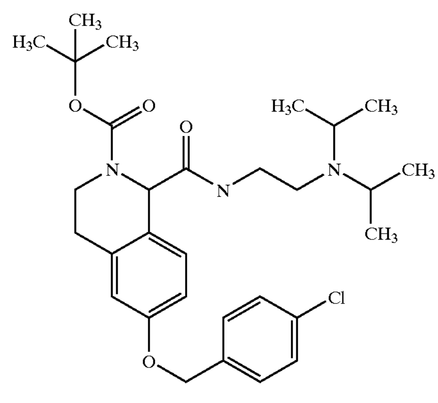 | 545 |
| 314 | 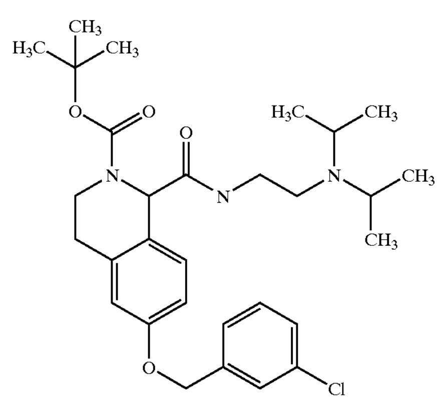 | 545 |

-continued
| Example No. | Structure | LC/MS (M + H)+ |
|---|---|---|
| 315 | 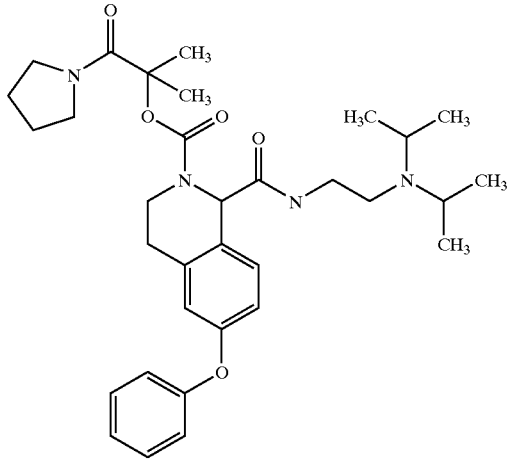 | 579 |
| 316 | 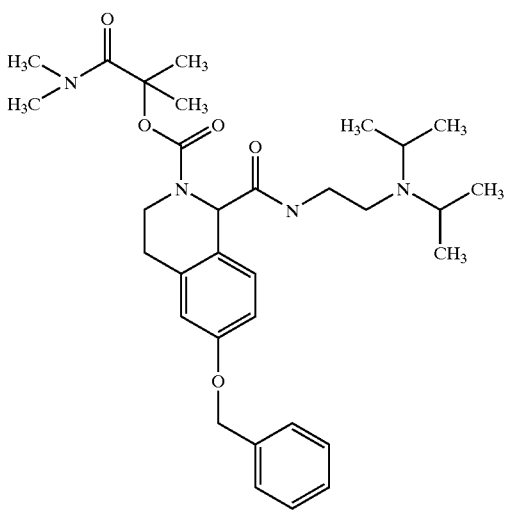 | 567 |
| 317 | 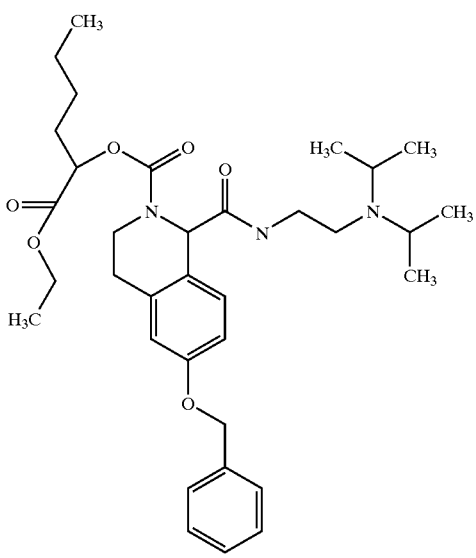 | 596 |

| Example No. | Structure | LC/MS (M + H)+ |
|---|---|---|
| 318 | 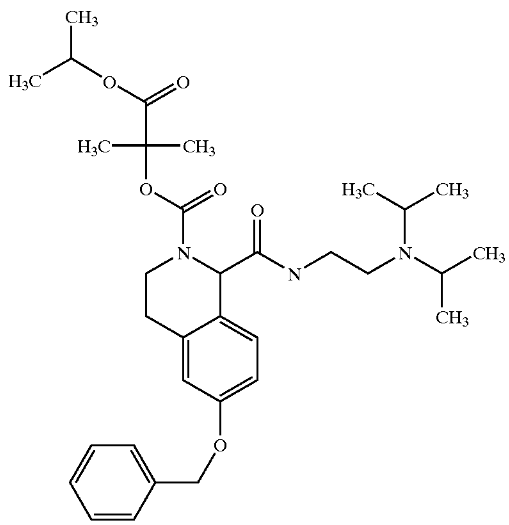 | 582 |
| 319 | 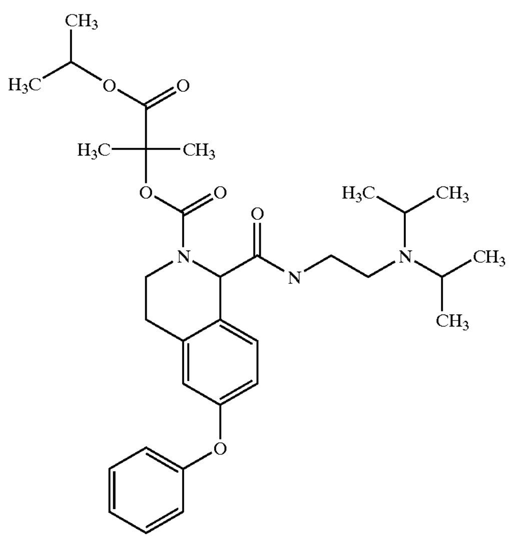 | 568 |
| 320 | 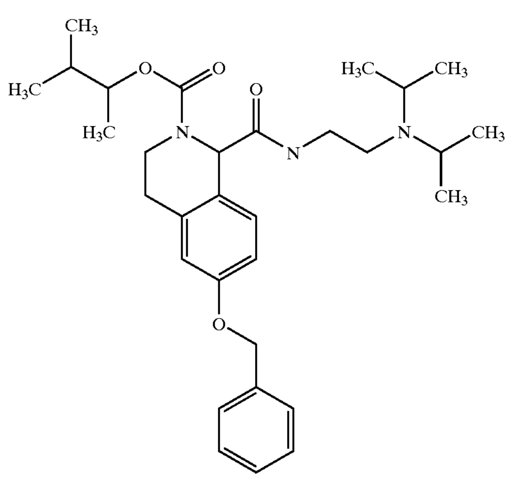 | 524 |

-continued
| Example No. | Structure | LC/MS (M + H)+ |
|---|---|---|
| 321 | 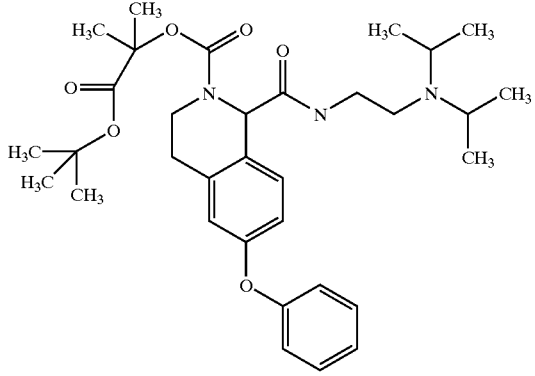 | 582 |
| 322 | 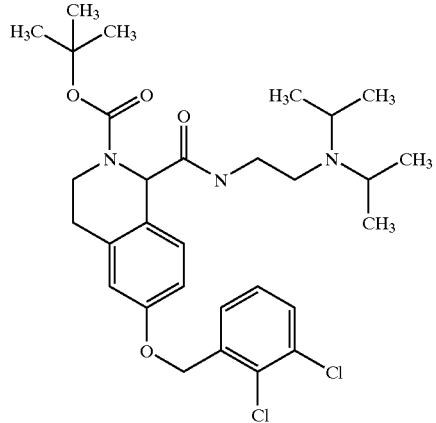 | 579 |
| 323 | 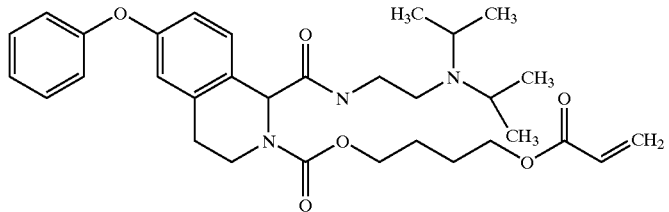 | 566 |
| 324 | 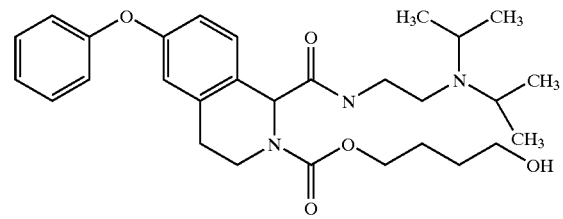 | 512 |

-continued

| Example No. | Structure | LC/MS (M + H)+ |
|---|---|---|
| 325 | 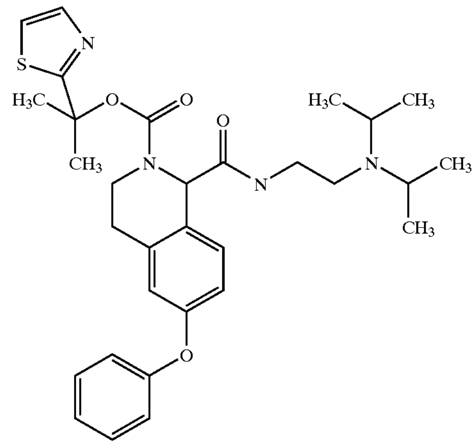 | 565 |
| 326 | 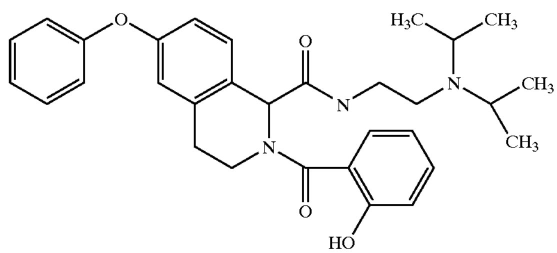 | 516 |
| 327 | 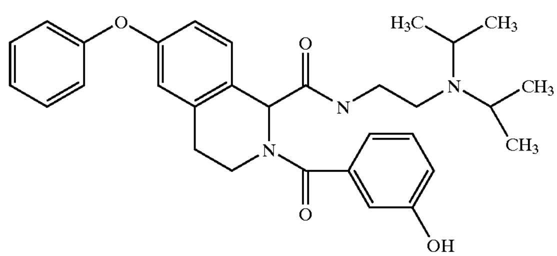 | 516 |
| 328 | 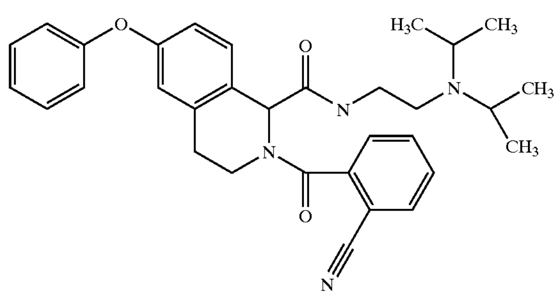 | 525 |
| 329 | 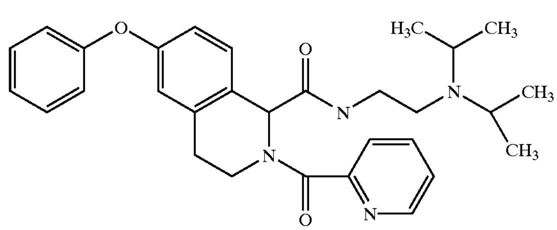 | 501 |

-continued

| Example No. | Structure | LC/MS (M + H)+ |
|---|---|---|
| 330 | (structure) | 501 |
| 331 | (structure) | 501 |
| 332 | (structure) | 424 |
| 333 | (structure) | 484 |
| 334 | (structure) | 496 |

-continued

| Example No. | Structure | LC/MS (M + H)+ |
|---|---|---|
| 335 | 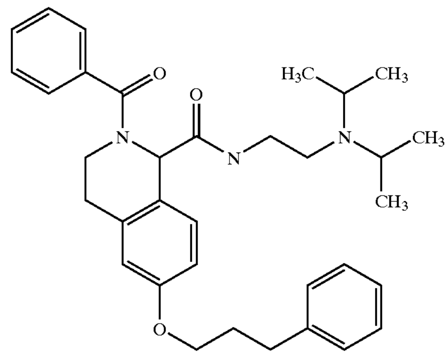 | 542 |
| 336 | 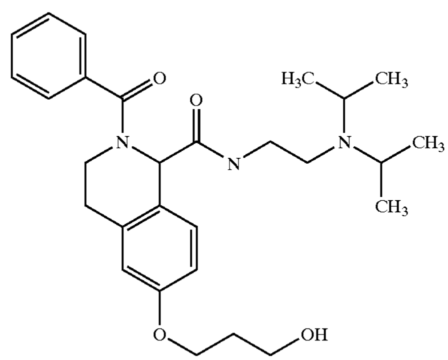 | 482 |
| 337 | 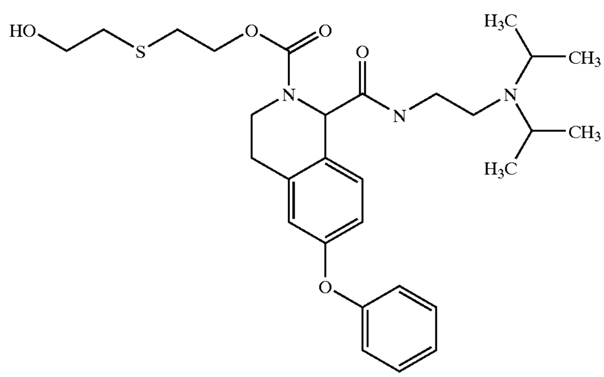 | 544 |
| 338 | 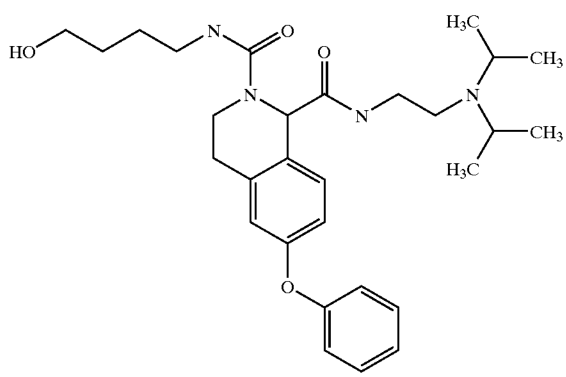 | 511 |

-continued
| Example No. | Structure | LC/MS (M + H)+ |
|---|---|---|
| 339 | 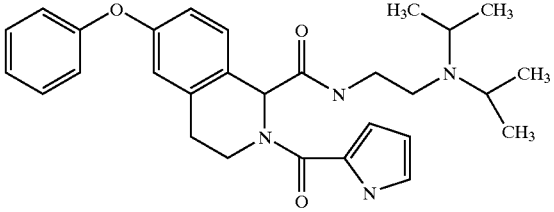 | 489 |
| 340 | 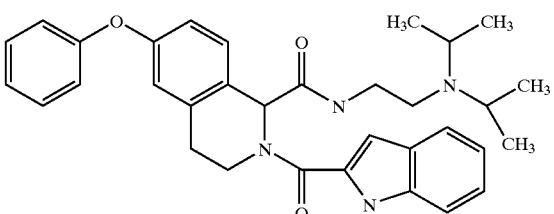 | 539 |
| 341 | 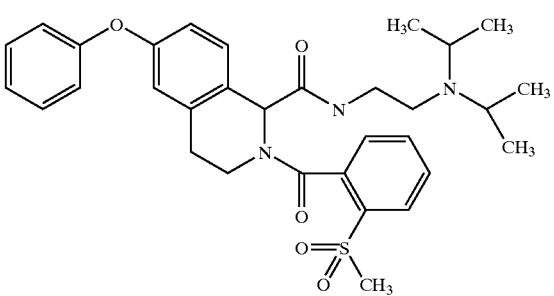 | 587 |
| 342 | 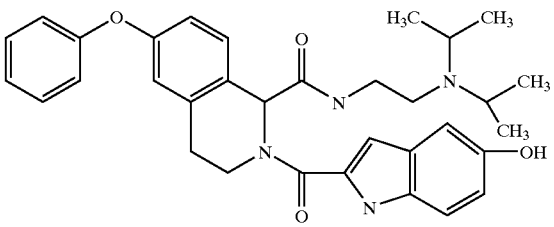 | 555 |
| 343 | 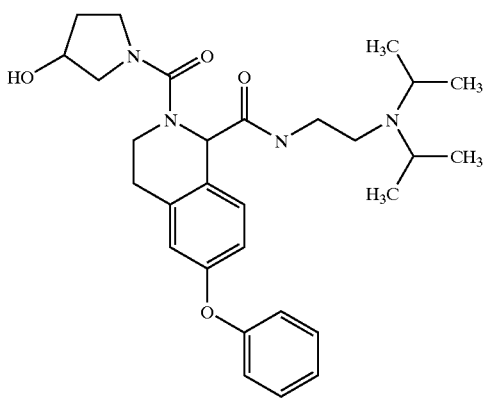 | 509 |

-continued

| Example No. | Structure | LC/MS (M + H)+ |
|---|---|---|
| 344 | 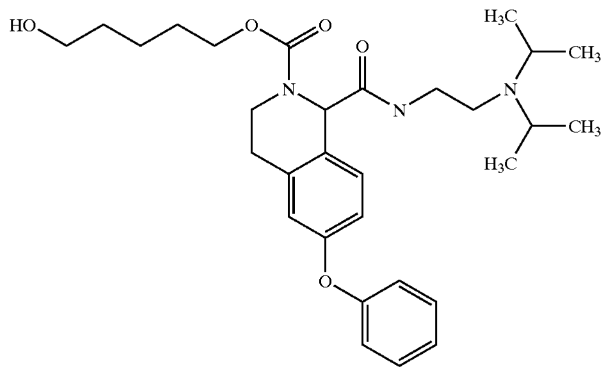 | 526 |
| 345 | 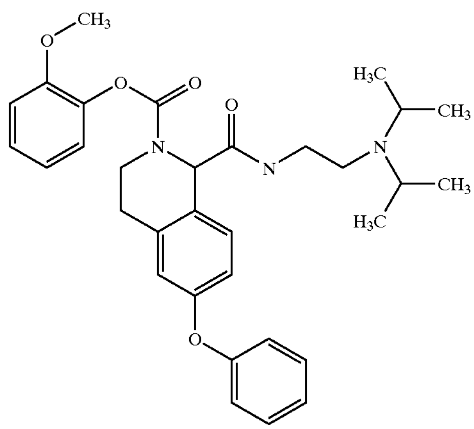 | 546 |
| 346 | 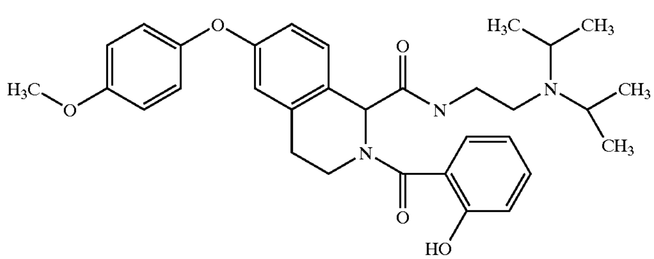 | 546 |
| 347 | 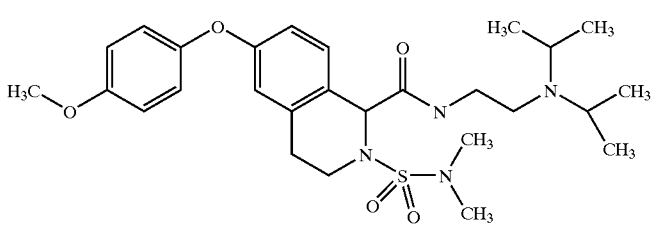 | 533 |

-continued

| Example No. | Structure | LC/MS (M + H)+ |
|---|---|---|
| 348 | 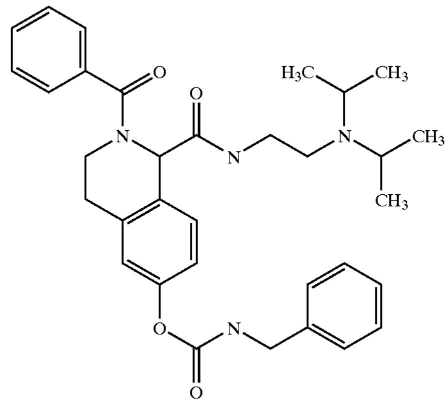 | 557 |
| 349 | 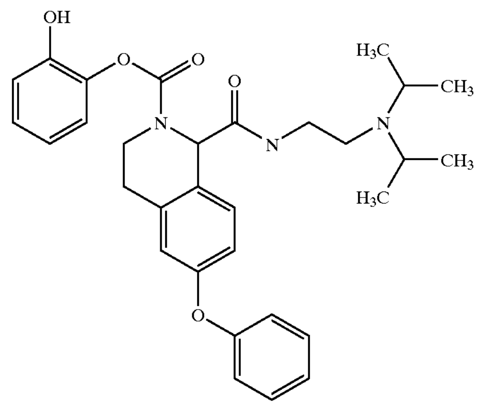 | 532 |

EXAMPLE 350

Isomer A and Isomer B

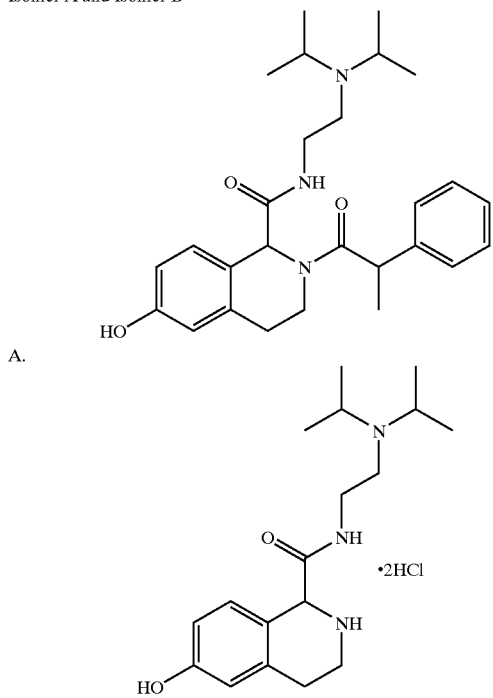

A.

Part B compound from Example 232 (0.1 g, 0.25 mmol) was dissolved in 4 M HCl in dioxane (2 mL) and stirred at room temperature for 1 hour. Concentration in vacuo gave the crude hydrochloride salt that was used in the next step.

B.

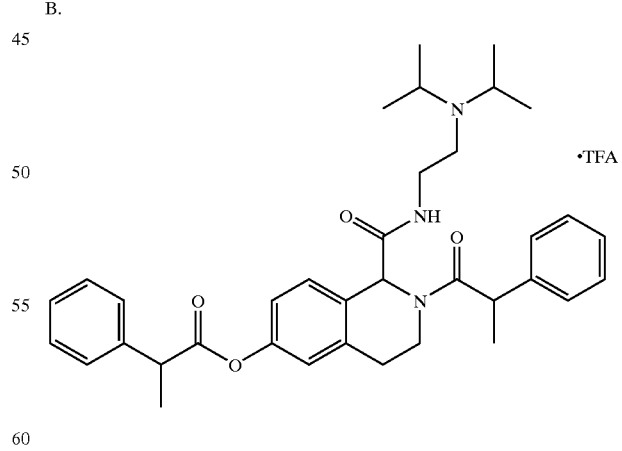

A solution of Part A compound (0.1 g, 0.25 mmol), 2-phenylethanoic acid (0.14 g, 0.94 mmol), diisopropylethylamine (0.08 g, 0.63 mmol) and hydroxybenzotriazole (0.105 g, 0.78 mmol) in DMF (3 mL) was stirred for 10 minutes. To this solution was added 1-(3-dimethylaminopropyl)-3-ethylcarbodiimide hydrochloride (0.149 g, 0.78 mmol) and the mixture was stirred at room temperature for 20 hours. The reaction was diluted with ethyl acetate and washed with water, saturated NaHCO₃, and brine. The organic layer was dried over magnesium sulfate, filtered and concentrated in vacuo to give the crude product. A small amount of this was purified using preparative HPLC to give the trifluoroacetate salt as a colorless oil: HPLCb rt=3.28 and 3.36 min; LC/MS (electrospray, +ions) m/z 584.3 (M+H).

C.

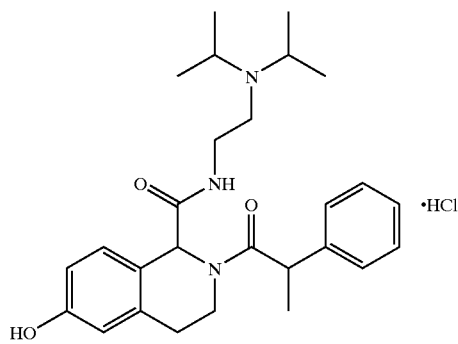

To a solution of Part B compound (0.1 g, 0.14 mmol) in methanol (1 mL) was added 2 N NaOH (1 mL) and the mixture stirred at room temperature for 1 hour. The reaction was concentrated in vacuo and the residue was dissolved in ethyl acetate and acidified with 1 N HCl to ~pH 1. This mixture was extracted with ethyl acetate (3×100 mL). The organic layers were combined, washed with saturated NaHCO₃, brine and dried over sodium sulfate, filtered and concentrated in vacuo to give the product as a white solid (32 mg): HPLCb rt=2.41 min; LC/MS (electrospray, +ions) m/z 452.3 (M+H).

EXAMPLES 351–388

A.

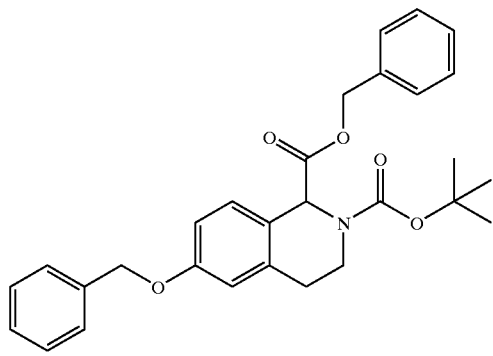

To a solution of Part A compound from Example 232 (1.0 g, 3.4 mmol) and potassium carbonate (2.0 g, 14.4 mmol) in DMF (10 mL) was added benzyl bromide (0.98 mL, 8.2 mmol) and the reaction stirred at room temperature for 4 hours. The mixture was concentrated in vacuo, the residue dissolved in ethyl acetate and washed with water. The organic layer was dried over magnesium sulfate, filtered, and concentrated to give the crude product (1.4 g).

B.

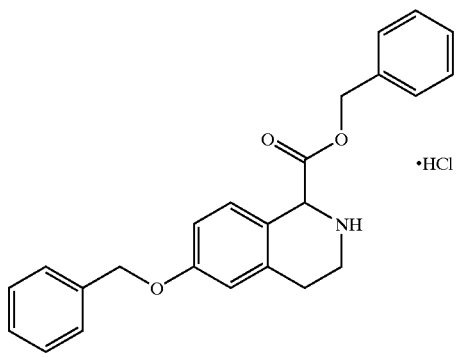

Part A compound (1.4 g, 2.9 mmol) was dissolved in 4 N HCl in dioxane (4 mL) and stirred for 2 hours. The mixture was concentrated in vacuo to give the crude hydrochloride salt (1.2 g).

C.

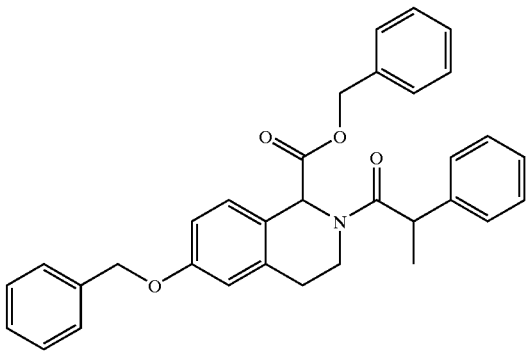

To a solution of Part B compound (1.2 g, 2.9 mmol), 2-phenylpropionic acid (0.59 mL, 4.4 mmol), diisopropylethylenediamine (0.5 mL, 3.0 mmol), and hydroxybenzotriazole (500 mg, 3.8 mmol) in dichloromethane (15 mL) was added 1-(3-dimethylaminopropyl)-3-ethylcarbodiimide hydrochloride (750 mg, 3.9 mmol) and the mixture was stirred at room temperature for 20 hours. The reaction was diluted with ethyl acetate and washed with water, saturated NaHCO₃, and brine. The organic layer was dried over magnesium sulfate, filtered and concentrated in vacuo to give the crude product.

D.

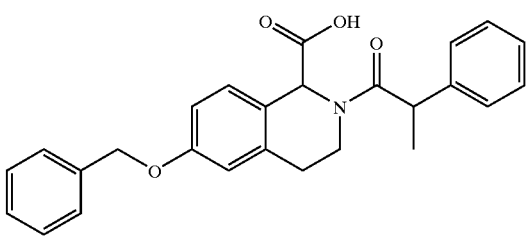

To a solution of Part C compound (1.5 g, 2.9 mmol) in methanol (1 mL), THF (1 mL), was added 10 M sodium hydroxide (0.7 mL, 7 mmol) and the mixture was stirred for 16 hours. The reaction mixture was transferred to a separatory funnel, acidified with 1 N HCl and extracted with ethyl acetate. The organic layers were combined, washed with brine, and dried over magnesium sulfate. The mixture was filtered and concentrated to give the product as a white solid.

E.

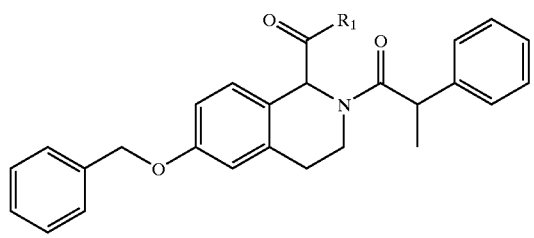

The compounds shown in the table below were synthesized in library format starting with Part D compound. Part D compound (200 µL of a 0.225 M solution in dichloromethane, 0.045 mmol), the appropriate amine (150 µL of a 0.20 M solution in dichloromethane, 0.030 mmol), and 1-hydroxybenzotriazole (0.045 mmol) and diisopropylcarbodiimide (0.045 mmol) in 250 µL DMF were stirred at room temperature for 16 hours. The reaction mixtures were loaded onto ion exchange cartridges (SCX, 0.5 g), washed with methanol (2×1.5 mL), 0.1 N $NH_3$ in methanol (2×1.5 mL), 2 M $NH_3$ in methanol. The concentrated ammonia fractions were collected and concentrated to give the desired products which gave the analytical data shown.

| Example No. | $X_1$—$R_1$ | Calc MW | LC/MS (M + H)+ |
|---|---|---|---|
| 351 | | 547.7 | 548.5 |
| 352 | | 522.7 | 523.48 |
| 353 | | 522.7 | 523.48 |
| 354 | | 569.8 | 570.55 |
| 355 | | 554.7 | 555.55 |
| 356 | | 553.8 | 554.53 |
| 357 | | 553.8 | 554.77 |
| 358 | | 541.7 | 542.51 |
| 359 | | 539.7 | 540.51 |
| 360 | | 527.7 | 528.52 |
| 361 | | 527.7 | 528.49 |
| 362 | | 525.7 | 526.51 |

-continued
= X₁—R₁
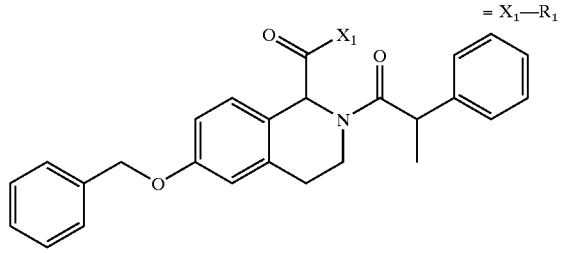
| Example No. | X₁—R₁ | Calc MW | LC/MS (M + H)⁺ |
|---|---|---|---|
| 363 | 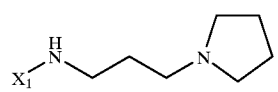 | 525.7 | 526.49 |
| 364 | 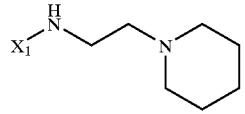 | 525.7 | 526.51 |
| 365 | 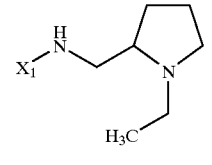 | 525.7 | 526.5 |
| 366 | 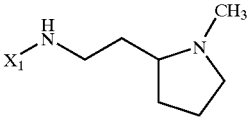 | 525.7 | 526.5 |
| 367 | 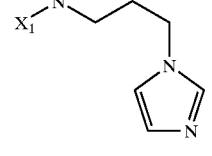 | 525.7 | 526.52 |
| 368 | 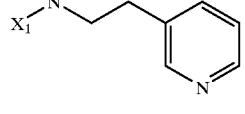 | 522.7 | 523.46 |
| 369 | 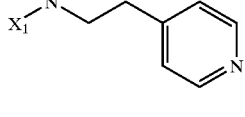 | 519.7 | 520.45 |
| 370 | 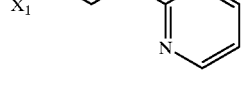 | 519.7 | 520.48 |
| 371 | 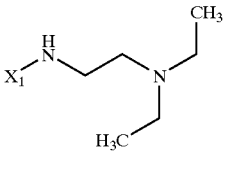 | 519.7 | 520.44 |
-continued
= X₁—R₁
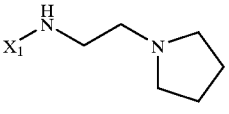
| Example No. | X₁—R₁ | Calc MW | LC/MS (M + H)⁺ |
|---|---|---|---|
| 372 | 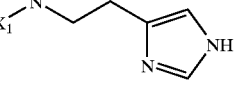 | 513.7 | 514.53 |
| 373 | 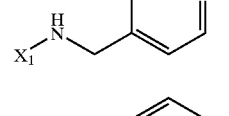 | 511.7 | 512.53 |
| 374 | 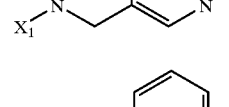 | 508.6 | 509.45 |
| 375 | 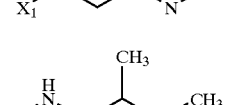 | 505.6 | 506.44 |
| 376 | 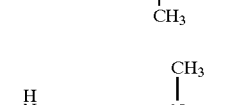 | 505.6 | 506.48 |
| 377 | 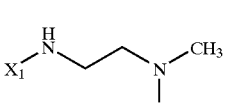 | 505.6 | 506.45 |
| 378 | 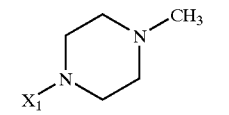 | 499.7 | 500.51 |
| 379 |  | 499.7 | 500.48 |
| 380 | | 485.6 | 486.47 |
| 381 | | 497.6 | 498.49 |

-continued

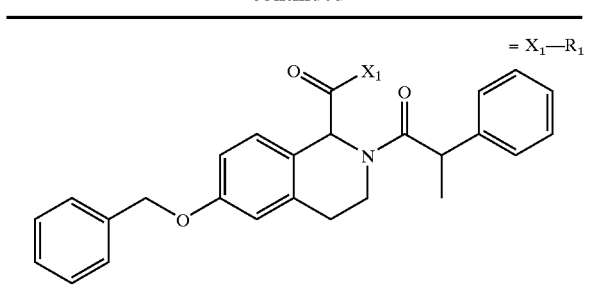

= X$_1$—R$_1$

| Example No. | X$_1$—R$_1$ | Calc MW | LC/MS (M + H)$^+$ |
|---|---|---|---|
| 382 | 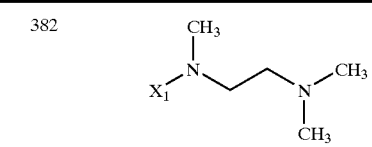 | 499.7 | 500.52 |
| 383 | 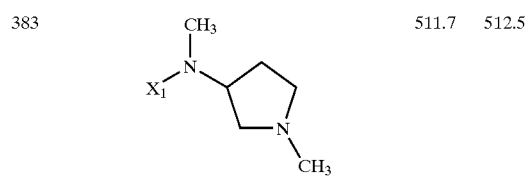 | 511.7 | 512.5 |
| 384 | 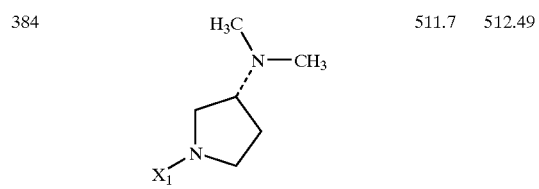 | 511.7 | 512.49 |
| 385 | 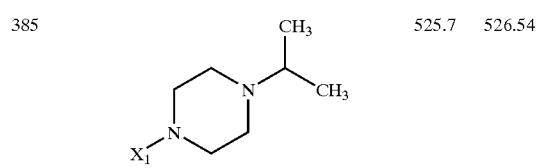 | 525.7 | 526.54 |
| 386 | 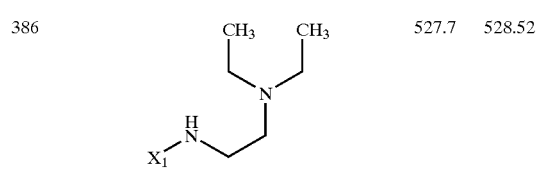 | 527.7 | 528.52 |
| 387 | 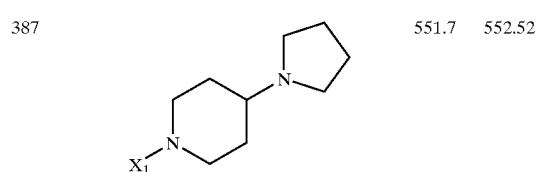 | 551.7 | 552.52 |
| 388 | 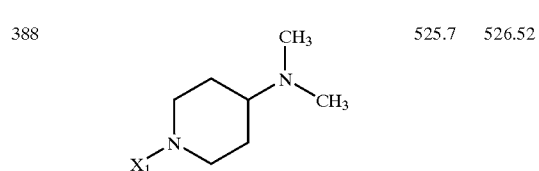 | 525.7 | 526.52 |

EXAMPLE 389

Isomer A and Isomer B

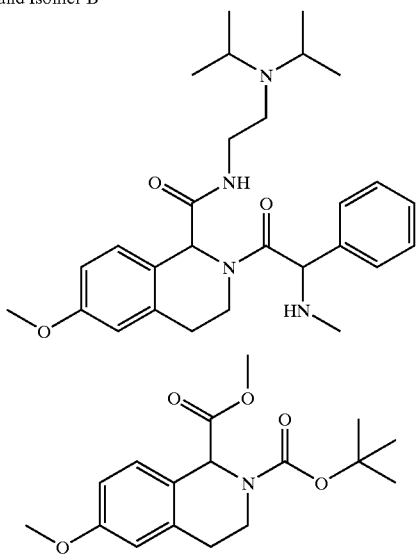

A.

To a solution of Part A compound from Example 232 (2 g, 6.8 mmol) and potassium carbonate (3.8 g, 27 mmol) in DMF (5 mL) was added methyl iodide (0.877 mL, 14 mmol) and the reaction stirred at room temperature for 4 hours. The mixture was concentrated in vacuo, the residue dissolved in ethyl acetate and washed with water. The organic layer was dried over magnesium sulfate, filtered, and concentrated to give the crude product (2 g).

B.

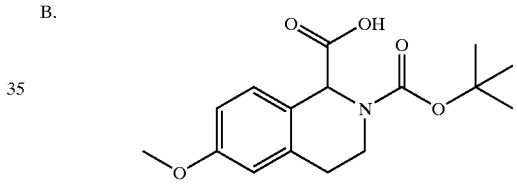

To a solution of Part A compound (2.0 g, 6.2 mmol) in methanol (10 mL), THF (10 mL), and water (10 mL) was added NaOH (820 mg, 20 mmol) and the mixture was stirred for 25 hours. The reaction mixture was transferred to a separatory funnel, acidified with 1 N HCl and extracted with ethyl acetate. The organic layers were combined, dried over magnesium sulfate, filtered and concentrated to give the product as a white solid (1.8 g).

C.

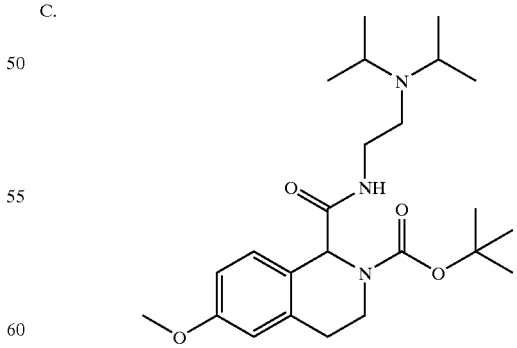

A solution of Part B compound (0.1 g, 0.3 mmol), diisopropylethylenediamine (52 mg, 0.36 mmol), and hydroxybenzotriazole (62 mg, 0.46 mmol) in DMF (2 mL) was stirred for 10 minutes. To this solution was added 1-(3-dimethylaminopropyl)-3-ethylcarbodiimide hydrochloride (72 mg, 0.36 mmol) and the mixture was stirred at room temperature for 20 hours. The reaction was diluted with ethyl acetate and washed with water, saturated NaHCO₃, and brine. The organic layer was dried over magnesium sulfate, filtered and concentrated in vacuo to give the crude product (0.15 g).

D.

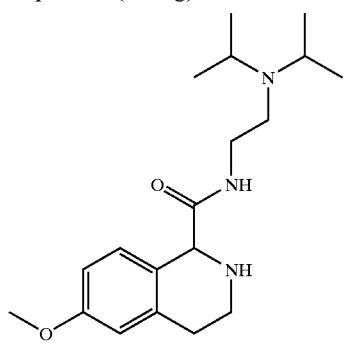

Part C compound (0.15 g, 0.35 mmol) was dissolved in 4 M HCl in dioxane (1 mL) and stirred at room temperature for 1 hour. Concentration in vacuo gave the crude hydrochloride salt. This was purified using an ion exchange column (SCX) eluting with 2 N NH₃ in methanol, followed by chromatography (silica gel, 15% MeOH in CH₂Cl₂ with 0.5% triethylamine, and a second pass through ion exchange resin to give the pure amine as the free base.

E.

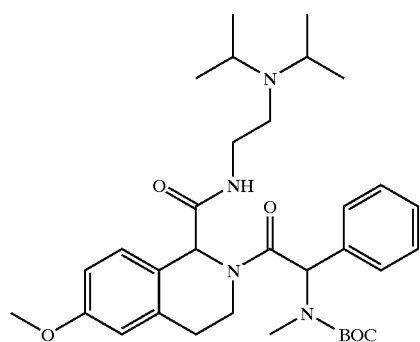

A solution of Part D compound (11 mg, 0.033 mmol), N-BOC—N-methylphenylglycine (12 mg, 0.045 mmol), diisopropylcarbodiimide (7 mL, 0.45 mmol) and 1-hydroxy-7-azabenzotriazole (6.1 mg, 0.45 mmol) in DMF (0.5 mL) and dichloromethane (0.5 mL) was stirred at room temperature for 16 hours. The reaction mixture was loaded onto an ion exchange cartridge (SCX, 0.5 g), washed with methanol (2×1.5 mL), 0.1 N NH₃ in methanol (2×1.5 mL), 2 M NH₃ in methanol. The concentrated ammonia fractions were collected and concentrated to give the desired product (6.5 mg).

F.

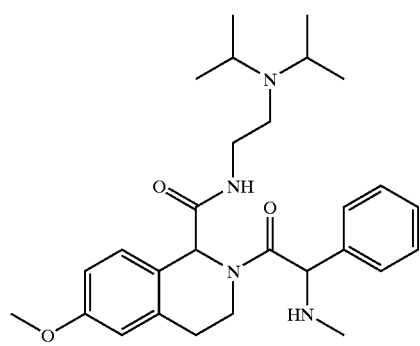

A solution of Part E compound (6.5 mg, 0.014 mmol) in 4 M HCl in dioxane (0.3 mL) was stirred at room temperature for 4 hours. The reaction mixture was loaded onto an ion exchange cartridge (SCX, 0.5 g), washed with methanol (2×1.5 mL), 0.1 N NH₃ in methanol (2×1.5 mL), 2 M NH₃ in methanol. The concentrated ammonia fractions were collected and concentrated to give the desired product (5 mg): HPLCb rt=1.8 and 2.0 min; LC/MS (electrospray, +ions) m/z 481.5 (M+H).

EXAMPLES 390–437

The compounds shown in the table below were synthesized in library format starting with Part D compound from Example 389. Part D compound from Example 61 (500 μL of a 0.06 M solution in dichloromethane, 0.03 mmol), the appropriate acid (300 μL of a 0.15 M solution in dichloromethane, 0.045 mmol), 1-hydroxy-7-azabenzotriazole (0.045 mmol), and diisopropylcarbodiimide (0.045 mmol) in 200 μL DMF were stirred at room temperature for 16 hours. The reaction mixtures were loaded onto ion exchange cartridges (SCX, 0.5 g), washed with methanol (2×1.5 mL), 0.1 N NH₃ in methanol (2×1.5 mL), 2 M NH₃ in methanol. The concentrated ammonia fractions were collected and concentrated to give the desired products which gave the analytical data shown.

| Example No. | X₁—R₁ | Calc MW | LC/MS (M + H)⁺ |
|---|---|---|---|
| 390 | | 465.64 | 466.5 |
| 391 | | 481.6 | 480.49 (M − H)⁻ |
| 392 | | 465.6 | 466.61 |

-continued

= X₁—R₁

[Structure: 6-methoxy-1,2,3,4-tetrahydroisoquinoline-1-carboxamide with N-(2-(diisopropylamino)ethyl) group and N2-X₁ substituent]

| Example No. | X₁—R₁ | Calc MW | LC/MS (M + H)⁺ |
|---|---|---|---|
| 393 | X₁-C(O)-CH(Et)-Ph | 479.7 | 480.62 |
| 394 | X₁-C(O)-(3-furyl) | 427.6 | 428.68 |
| 395 | X₁-C(O)-CH₂CH₂-C(O)-Ph | 493.7 | 494.75 |
| 396 | X₁-C(O)-CH₂-(3-methoxyphenyl) | 481.6 | 482.75 |
| 397 | X₁-C(O)-(2,3-dihydrobenzofuran-5-yl) | 479.6 | 480.75 |
| 398 | X₁-C(O)-(benzofuran-2-yl) | 477.6 | 478.72 |

-continued

= X₁—R₁

[Structure: 6-methoxy-1,2,3,4-tetrahydroisoquinoline-1-carboxamide with N-(2-(diisopropylamino)ethyl) group and N2-X₁ substituent]

| Example No. | X₁—R₁ | Calc MW | LC/MS (M + H)⁺ |
|---|---|---|---|
| 399 | X₁-C(O)-(4-(dimethylamino)phenyl) | 480.7 | 479.52 (M − H)⁻ |
| 400 | X₁-C(O)-(4-methoxyphenyl) | 467.6 | 468.45 |
| 401 | X₁-C(O)-(4-(trifluoromethyl)phenyl) | 505.6 | 506.56 |
| 402 | X₁-C(O)-CH₂-(3-pyridyl) | 452.6 | 453.59 |
| 403 | X₁-C(O)-CH₂CH₂-C(O)-(4-chlorophenyl) | 527.3 | 528.46 |
| 404 | X₁-C(O)-(4-pyridyl) | 438.6 | 439.74 |

-continued

= X₁—R₁

| Example No. | X₁—R₁ | Calc MW | LC/MS (M + H)⁺ |
|---|---|---|---|
| 405 | X₁-C(O)-pyrazin-2-yl | 439.6 | 440.46 |
| 406 | X₁-C(O)-pyridin-3-yl | 438.6 | 439.51 |
| 408 | X₁-C(O)-(4-phenoxyphenyl) | 529.7 | 530.59 |
| 409 | X₁-C(O)-CH(Ph)-CH₂OH | 481.6 | 482.74 |
| 410 | X₁-C(O)-CH₂-(pyridin-3-yl) | 451.6 | 452.73 |
| 411 | X₁-C(O)-CH₂-(2,4-dichlorophenyl) | 519.2 | 520.43 |
| 412 | X₁-C(O)-CH₂-(2-methoxyphenyl) | 481.6 | 482.61 |
| 413 | X₁-C(O)-(2-methylphenyl) | 451.6 | 452.59 |
| 414 | X₁-C(O)-CH₂-(3-chlorophenyl) | 485.2 | 486.55 |
| 415 | X₁-C(O)-CH₂-(3,4-dichlorophenyl) | 519.2 | 520.41 |
| 416 | X₁-C(O)-CH₂-(3,4-dimethoxyphenyl) | 511.7 | 512.75 |
| 417 | X₁-C(O)-CH₂-(3-methylphenyl) | 465.6 | 466.61 |

-continued

= X₁—R₁

[Structure: 6-methoxy-tetrahydroisoquinoline-1-carboxamide with N-(2-(diisopropylamino)ethyl) group and N2-X₁ substituent]

| Example No. | X₁—R₁ | Calc MW | LC/MS (M + H)⁺ |
|---|---|---|---|
| 418 | [4-methoxyphenylacetyl] | 481.6 | 482.58 |
| 419 | [4-methylphenylacetyl] | 465.6 | 466.62 |
| 420 | [1H-indol-3-ylcarbonyl] | 476.6 | 477.5 |
| 421 | [4-nitrophenylacetyl] | 496.6 | 497.48 |
| 422 | [1-phenylcyclopropyl carbonyl] | 477.7 | 478.62 |
| 423 | [1-(4-chlorophenyl)cyclopropyl carbonyl] | 511.3 | 512.58 |

-continued

= X₁—R₁

[Structure: 6-methoxy-tetrahydroisoquinoline-1-carboxamide with N-(2-(diisopropylamino)ethyl) group and N2-X₁ substituent]

| Example No. | X₁—R₁ | Calc MW | LC/MS (M + H)⁺ |
|---|---|---|---|
| 424 | [5-methyl-3-phenylisoxazole-4-carbonyl] | 518.7 | 519.6 |
| 425 | [3-(trifluoromethyl)phenylacetyl] | 519.6 | 520.58 |
| 426 | [4-chlorophenylacetyl] | 485.2 | 486.57 |
| 427 | [quinoline-3-carbonyl] | 488.6 | 489.45 |
| 428 | [1H-imidazole-4-carbonyl] | 427.6 | 426.46 (M − H)⁻ |
| 429 | [benzo[d][1,3]dioxol-5-ylacetyl] | 495.6 | 496.6 |

-continued
= X₁—R₁
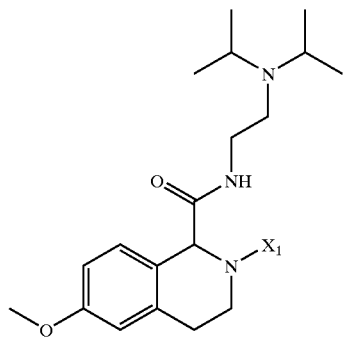
| Example No. | X₁—R₁ | Calc MW | LC/MS (M + H)⁺ |
|---|---|---|---|
| 430 | 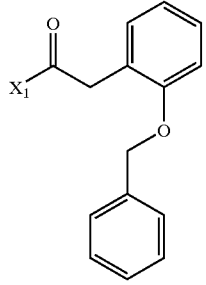 | 557.7 | 558.63 |
| 431 | 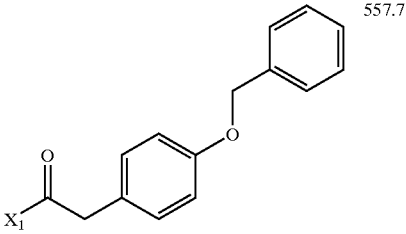 | 557.7 | 558.64 |
| 432 | 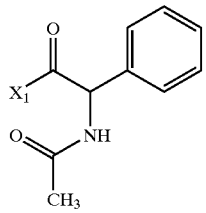 | 508.7 | 509.63 |
| 433 | 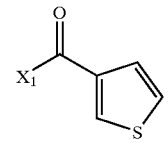 | 443.6 | 444.54 |
-continued
= X₁—R₁
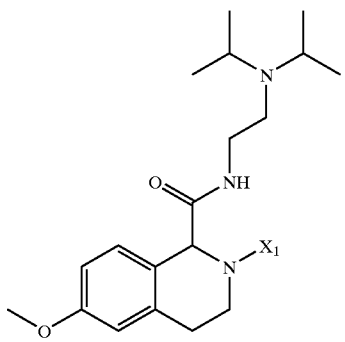
| Example No. | X₁—R₁ | Calc MW | LC/MS (M + H)⁺ |
|---|---|---|---|
| 434 | 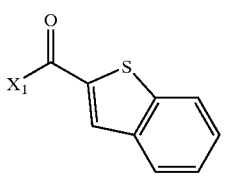 | 493.7 | 494.55 |
| 435 | 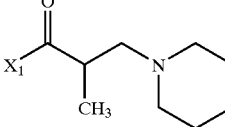 | 456.6 | 457.59 |
| 436 | 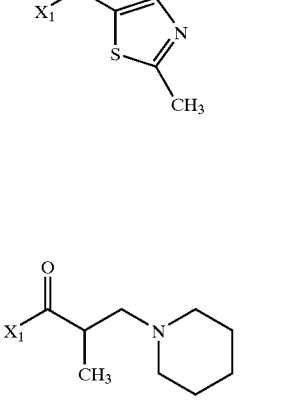 | 472.7 | 473.45 |
| 437 | | 486.7 | 487.58 |

EXAMPLE 438

Isomer A and Isomer B

A.

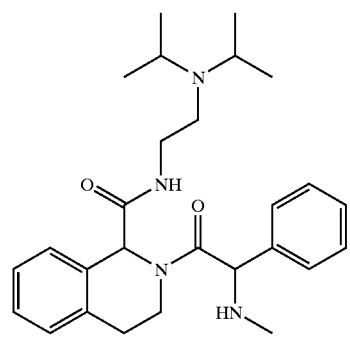

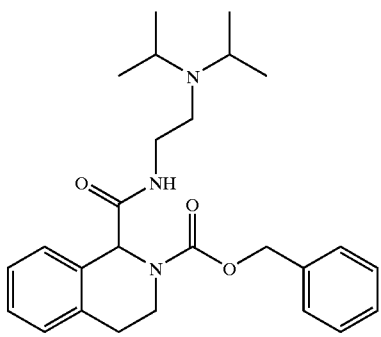

A solution of N-benzyloxycarbonyl-DL-1,2,3,4-tetrahydro-isoquinoline-1-carboxylic acid (0.31 g, 1 mmol), prepared according to a published procedure in WO9312091, diisopropylethylenediamine (0.16 g, 1.1 mmol), and hydroxybenzotriazole (0.19 mg, 1.4 mmol) in DMF (3 mL) was stirred for 10 minutes. To this solution was added 1-(3-dimethylaminopropyl)-3-ethylcarbodiimide hydrochloride (0.21 g, 1.1 mmol) and the mixture was stirred at room temperature for 20 hours. The reaction was diluted with ethyl acetate and washed with water, saturated NaHCO₃, and brine. The organic layer was dried over magnesium sulfate, filtered and concentrated in vacuo to give the crude product (0.5 g).

B.

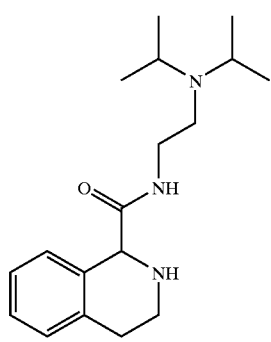

To a solution of Part A compound (2.2 g, 5.0 mmol) in ethanol (10 mL) and acetic acid (1 mL) was added 10% palladium on carbon (0.3 g). The flask was charged with hydrogen at atmospheric pressure and stirred for 16 hours. The reaction mixture was filtered through a pad of celite and concentrated to give the crude product (1.5 g). Purification using chromatography (silica gel, 15% methanol/ dichloromethane with 0.5% triethylamine) gave the desired product as a white solid.

C.

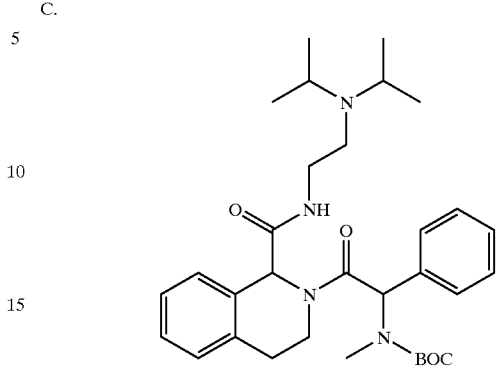

A solution of Part B compound (10 mg, 0.033 mmol), N-BOC—N-methylphenylglycine (12 mg, 0.045 mmol), diisopropylcarbodiimide (7 mL, 0.45 mmol) and 1-hydroxy-7-azabenzotriazole (6.1 mg, 0.45 mmol) in DMF (0.5 mL) and dichloromethane (0.5 mL) was stirred at room temperature for 16 hours. The reaction mixture was loaded onto an ion exchange cartridge (SCX, 0.5 g), washed with methanol (2×1.5 mL), 0.1 N NH₃ in methanol (2×1.5 mL), and 2 M NH₃ in methanol. The concentrated ammonia fractions were collected and concentrated to give the desired product (10 mg).

D.

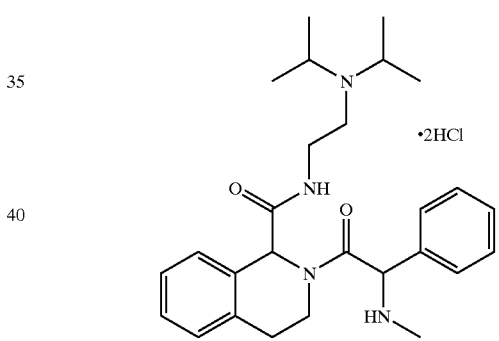

A solution of Part C compound (10 mg, 0.018 mmol) in 4 M HCl in dioxane (0.4 mL) was stirred at room temperature for 1 hour. The reaction mixture was concentrated to give the desired product as an oil (11 mg): HPLCb rt=1.77 and 2.0 min; LC/MS (electrospray, +ions) m/z 451.5 (M+H)

EXAMPLES 439–486

The compounds shown in the table below were synthesized in library format starting with Part B compound from Example 109. Part B compound from Example 109 (500 μL of a 0.06 M solution in dichloromethane, 0.03 mmol), the appropriate acid (300 μL of a 0.15 M solution in dichloromethane, 0.045 mmol), 1-hydroxy-7-azabenzotriazole (0.045 mmol), and diisopropylcarbodiimide (0.045 mmol) in 200 μL DMF were stirred at room temperature for 16 hours. The reaction mixtures were loaded onto ion exchange cartridges (SCX, 0.5 g), washed with methanol (2×1.5 mL), 0.1 N NH₃ in methanol (2×1.5 mL), and 2 M NH₃ in methanol. The concentrated ammonia fractions were collected and concentrated to give the desired products which gave the analytical data shown.

| Example No. | X₁-R₁ | Calc MW | LC/MS (M + H)⁺ |
|---|---|---|---|
| 439 | (2-phenylpropanoyl) | 435.61 | 436.5 |
| 440 | (4-ethoxybenzoyl) | 451.6 | 452.61 |
| 441 | (2-(2-methylphenyl)acetyl) | 435.6 | 436.61 |
| 442 | (2-phenylbutanoyl) | 449.6 | 450.62 |
| 443 | (furan-3-carbonyl) | 397.5 | 398.54 |
| 444 | (4-oxo-4-phenylbutanoyl) | 463.6 | 464.61 |
| 445 | (2-(3-methoxyphenyl)acetyl) | 451.6 | 452.61 |
| 446 | (2,3-dihydrobenzofuran-5-carbonyl) | 449.6 | 450.58 |
| 447 | (benzofuran-2-carbonyl) | 447.6 | 448.57 |
| 448 | (4-(dimethylamino)benzoyl) | 450.6 | 451.63 |
| 449 | (4-methoxybenzoyl) | 437.6 | 438.59 |
| 450 | (4-(trifluoromethyl)benzoyl) | 475.6 | 476.57 |

-continued
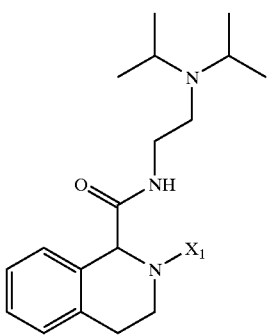
= X₁-R₁
| Example No. | X₁-R₁ | Calc MW | LC/MS (M + H)⁺ |
|---|---|---|---|
| 451 | 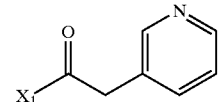 | 422.6 | 423.6 |
| 452 | 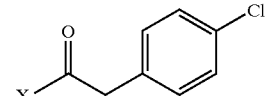 | 497.2 | 498.57 |
| 453 | 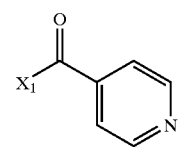 | 408.6 | 409.61 |
| 454 | 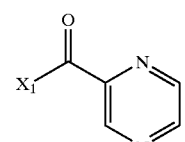 | 409.5 | 410.57 |
| 455 | 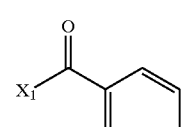 | 408.6 | 409.59 |
| 456 | 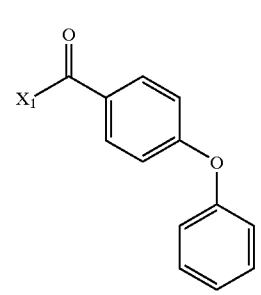 | 499.7 | 500.61 |
| 457 | 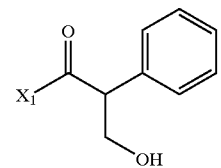 | 451.6 | 452.63 |
-continued
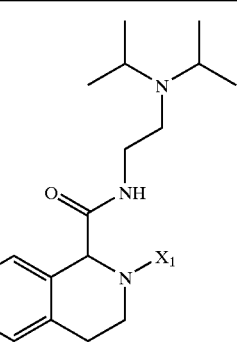
= X₁-R₁
| Example No. | X₁-R₁ | Calc MW | LC/MS (M + H)⁺ |
|---|---|---|---|
| 458 |  | 421.6 | 422.59 |
| 459 | 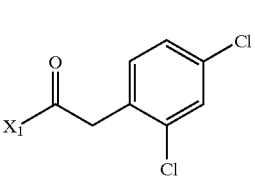 | 489.2 | 490.52 |
| 460 | 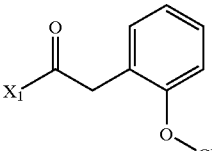 | 451.6 | 452.6 |
| 461 | 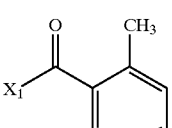 | 421.6 | 422.59 |
| 462 | 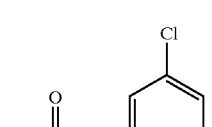 | 455.2 | 456.56 |
| 463 | 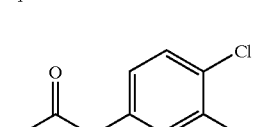 | 489.2 | 490.53 |
| 464 | 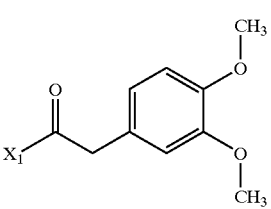 | 481.6 | 482.62 |

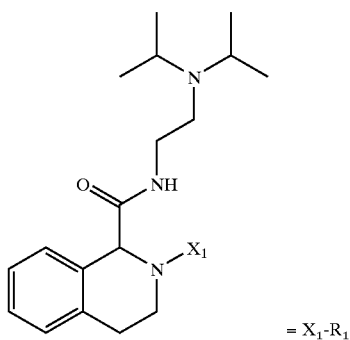

= X₁-R₁

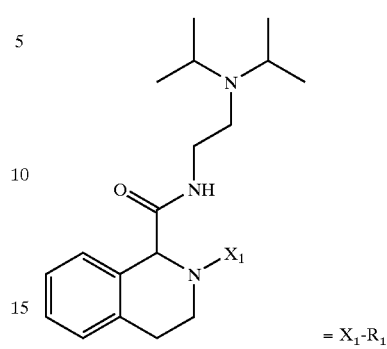

= X₁-R₁

| Example No. | X₁-R₁ | Calc MW | LC/MS (M + H)⁺ | Example No. | X₁-R₁ | Calc MW | LC/MS (M + H)⁺ |
|---|---|---|---|---|---|---|---|
| 465 | 3-methylbenzyl C(=O)- | 435.6 | 436.61 | 472 | 5-methyl-3-phenylisoxazole-4-carbonyl | 488.6 | 489.62 |
| 466 | 4-methoxybenzyl C(=O)- | 451.6 | 452.6 | 473 | 3-(trifluoromethyl)benzyl C(=O)- | 489.6 | 490.59 |
| 467 | 4-methylbenzyl C(=O)- | 435.6 | 436.62 | 474 | 4-chlorobenzyl C(=O)- | 455.2 | 456.57 |
| 468 | indole-3-carbonyl | 446.6 | 447.59 | 475 | quinoline-3-carbonyl | 458.6 | 459.49 |
| 469 | 4-nitrobenzyl C(=O)- | 466.6 | 467.57 | 476 | benzo[1,3]dioxol-5-ylmethyl C(=O)- | 465.6 | 466.61 |
| 470 | 1-phenylcyclopropanecarbonyl | 447.6 | 448.63 | 477 | 2-(benzyloxy)benzyl C(=O)- | 527.7 | 528.63 |
| 471 | 1-(4-chlorophenyl)cyclopropanecarbonyl | 481.3 | 482.58 | | | | |

-continued
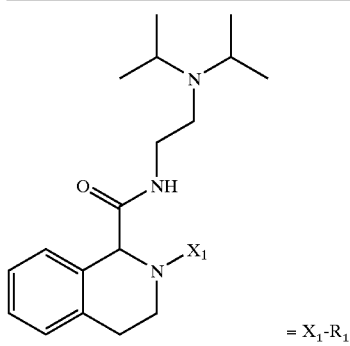
= X₁-R₁
| Example No. | X₁-R₁ | Calc MW | LC/MS (M + H)⁺ |
|---|---|---|---|
| 478 | 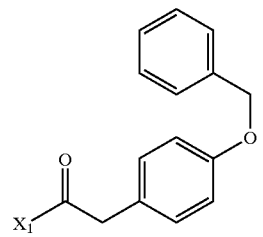 | 527.7 | 528.64 |
| 479 | | 422.6 | 423.59 |
| 480 | | 422.6 | 423.49 |
| 481 | | 478.6 | 479.52 |
| 482 | | 413.6 | 414.55 |
-continued
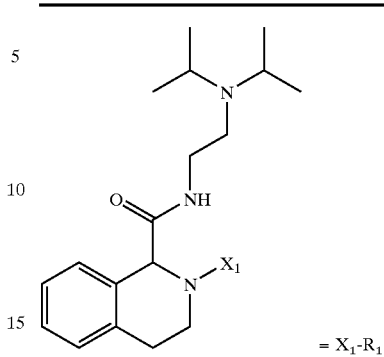
= X₁-R₁
| Example No. | X₁-R₁ | Calc MW | LC/MS (M + H)⁺ |
|---|---|---|---|
| 483 | 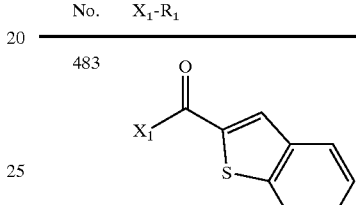 | 463.6 | 464.57 |
| 484 | | 426.6 | 427.59 |
| 485 | | 442.6 | 443.56 |
| 486 | | 456.7 | 457.58 |

EXAMPLE 487

Isomer A and Isomer B

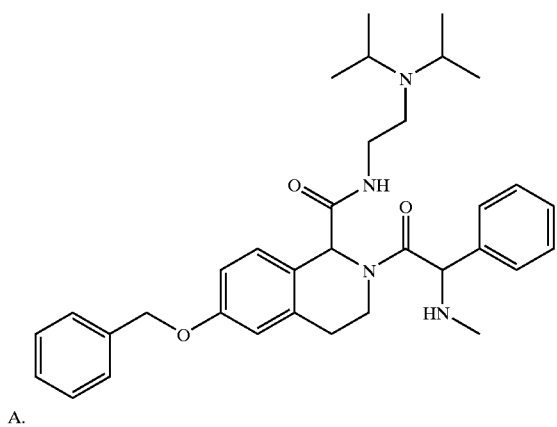

A.

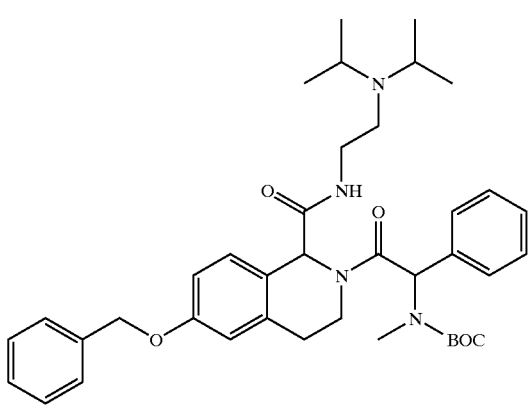

A solution of Part A compound from Example 64 (0.25 g, 0.60 mmol), N-BOC-N-methylphenylglycine (0.24 g, 0.90 mmol), diisopropylcarbodiimide (143 μL, 0.90 mmol) and 1-hydroxy-7-azabenzotriazole (0.12 g, 0.90 mmol) in DMF (2 mL) and dichloromethane (2 mL) was stirred at room temperature for 16 hours. The reaction mixture was loaded onto an ion exchange cartridge (SCX, 0.5 g), washed with methanol (2×1.5 mL), 0.1 N NH₃ in methanol (2×1.5 mL), and 2 M NH₃ in methanol. The concentrated ammonia fractions were collected and concentrated to give the desired product (0.1 g).

B.

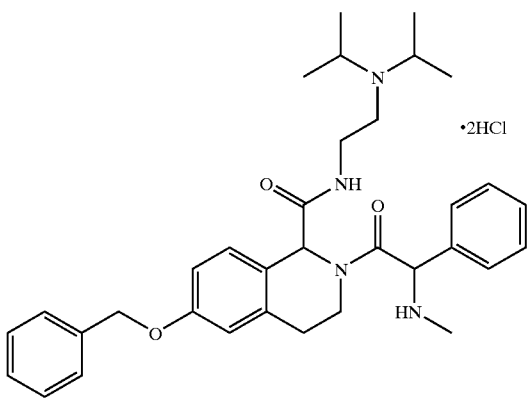

A solution of Part A compound (130 mg, 0.20 mmol) in 4 M HCl in dioxane (2 mL) was stirred at room temperature for 1 hour. The reaction mixture was concentrated to give the desired product as a light brown solid (11 mg): HPLCb rt=2.44 and 2.68 min; LC/MS (electrospray, +ions) m/z 557.5 (M+H).

EXAMPLE 488 AND 489

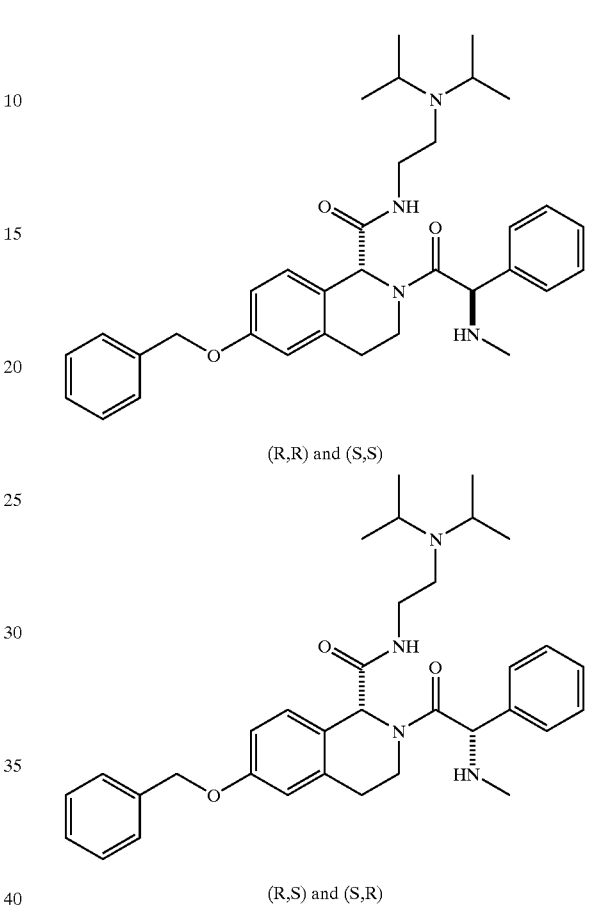

(R,R) and (S,S)

(R,S) and (S,R)

A sample of Part B compound from Example 487 (0.6 g) was purified using preparative chromatography and the two bands corresponding to the diastereomer pairs were isolated. The material in each band was isolated from the fractions by loading the corresponding fractions onto an ion exchange cartridge (SCX, 0.5 g), washing with methanol (2×1.5 mL), 0.1 N NH₃ in methanol (2×1.5 mL), and 2 M NH₃ in methanol. The concentrated ammonia fractions were collected and concentrated to give the desired product. Isomer pair A (110 mg): HPLCb rt=2.71 min; LC/MS (electrospray, +ions) m/z 557.5 (M+H); Isomer pair B (80 mg):HPLCb rt=2.90 min; LC/MS (electrospray, +ions) m/z 557.5 (M+H).

EXAMPLES 490–503

The compounds shown in the table below were synthesized in library format starting with Part A compound from Example 7. Part A compound from Example 7 (500 μL of a 0.06 M solution in dichloromethane, 0.03 mmol), the appropriate acid (300 μL of a 0.15 M solution in dichloromethane, 0.045 mmol), 1-hydroxy-7-azabenzotriazole (0.045 mmol), and diisopropylcarbodiimide (0.045 mmol) in 200 μL DMF were stirred at room temperature for 16 hours. The reaction mixtures were loaded onto ion exchange cartridges (SCX, 0.5 g), washed with methanol (2×1.5 mL), 0.1 N NH₃ in methanol (2×1.5 mL), and 2 M NH₃ in methanol. The concentrated ammonia fractions were collected and concentrated to give the desired products which gave the analytical data shown.
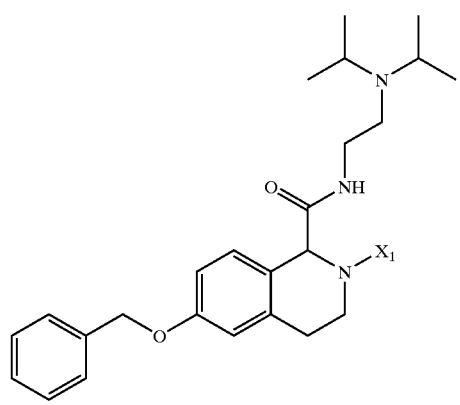
= X$_1$-R$_1$
| Example No | X$_1$-R$_1$ | Calc MW | LC/MS (M + H)$^+$ |
|---|---|---|---|
| 490 | 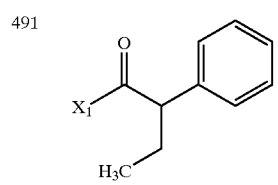 | 527.7 | 528.74 |
| 491 | | 555.8 | 556.78 |
| 492 | 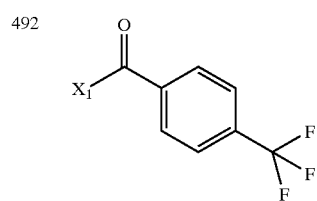 | 581.7 | 582.72 |
| 493 | | 528.7 | 529.74 |
| 494 | 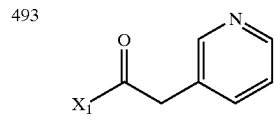 | 603.3 | 604.72 |
| 495 | 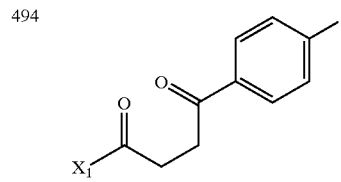 | 595.2 | 596.67 |
-continued
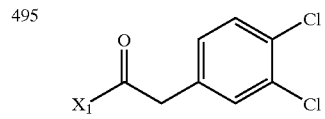
= X$_1$-R$_1$
| Example No | X$_1$-R$_1$ | Calc MW | LC/MS (M + H)$^+$ |
|---|---|---|---|
| 496 | | 587.8 | 588.76 |
| 497 | | 541.7 | 542.76 |
| 498 | | 541.7 | 542.75 |
| 499 | | 587.3 | 588.71 |
| 500 | | 561.3 | 562.7 |
| 501 | | 564.7 | 565.74 |
| 502 | | 555.8 | 556.78 |

-continued

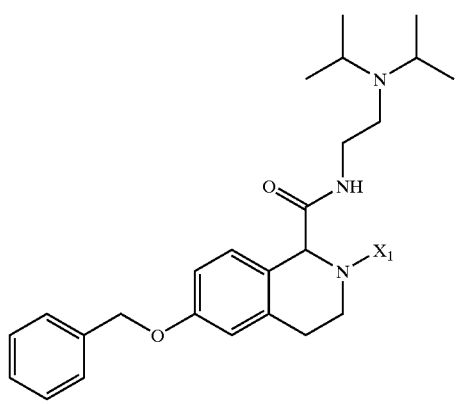

| Example No | $X_1$-$R_1$ = $X_1$-$R_1$ | Calc MW | LC/MS $(M + H)^+$ |
|---|---|---|---|
| 503 | 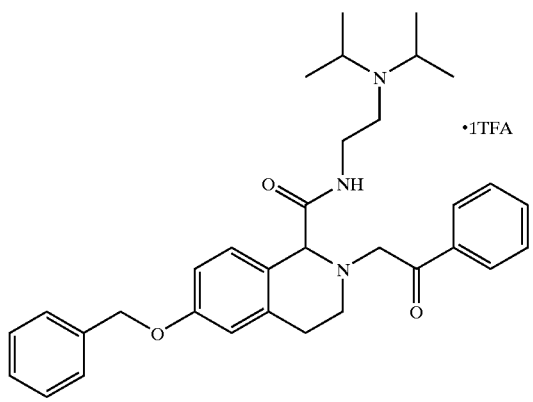 (not this) | 548.8 | 549.73 |

EXAMPLE 504

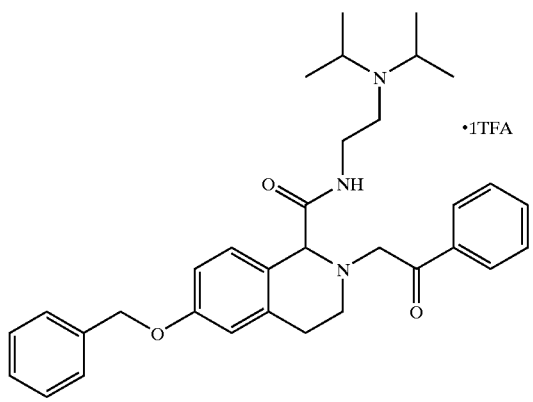

To a solution of Part A compound from Example 64 (50 mg, 0.12 mmol) and 2-bromoacetophenone (26 mg, 0.13 mmol) in acetone (2 mL) was added potassium carbonate (0.15 g) and the mixture was stirred at room temperature for 16 hours. The solution was diluted with ethyl acetate and washed with water. The organic layer was dried over sodium sulfate, filtered, and concentrated in vacuo to give the crude product. Some of this product was purified using preparative HPLC to give the trifluroacetate salt (6.5 mg): HPLCb rt=2.71; LC/MS (electrospray, +ions) m/z 528.47 (M+H).

EXAMPLE 505

Isomer A and Isomer B

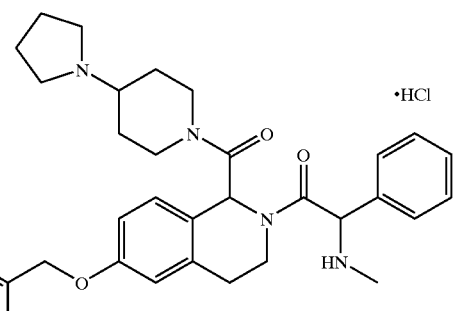

A.

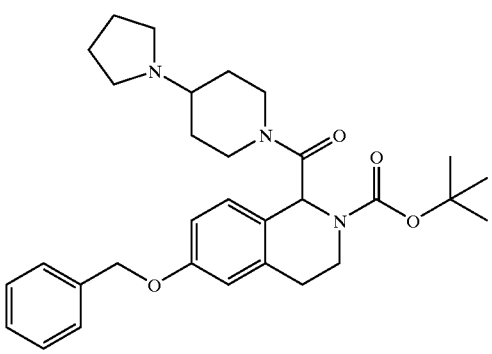

To a solution of Part E compound from Example 1 (0.6 g, 1.56 mmol), 4-(1-pyrrolidinyl)piperidine (0.29 g, 1.9 mmol), and 1-hydroxy-7-azabenzotriazole (0.21 g, 1.9 mmol) in DMF (3 mL) was added 1-(3-dimethylaminopropyl)-3-ethylcarbodiimide hydrochloride (0.3 g, 1.9 mmol) and the mixture was stirred at room temperature for 20 hours. The reaction mixture was loaded onto an ion exchange cartridge (SCX, 0.5 g), washed with methanol (2×1.5 mL), 0.1 N $NH_3$ in methanol (2×1.5 mL), and 2 M $NH_3$ in methanol. The concentrated ammonia fractions were collected and concentrated to give the desired product (0.7 g).

B.

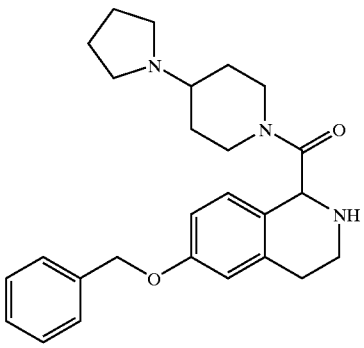

Part A compound (0.7 g, 1.3 mmol) was dissolved in 4 M HCl in dioxane (1 mL) and stirred at room temperature for 1 hour. Concentration in vacuo gave the crude hydrochloride salt. The reaction mixture was loaded onto an ion exchange cartridge (SCX, 0.5 g), washed with methanol (2×1.5 mL), 0.1 N NH₃ in methanol (2×1.5 mL), and 2 M NH₃ in methanol. The concentrated ammonia fractions were collected and concentrated to give the desired product (0.5 g).

C.

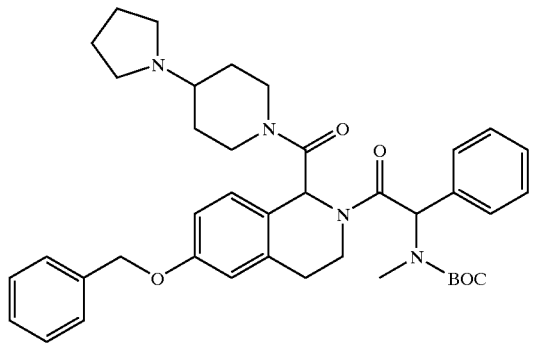

A solution of Part B compound (0.1 g, 0.24 mmol), N-BOC—N-methylphenylglycine (76 mg, 0.28 mmol), diisopropylcarbodiimide (45 μL, 0.28 mmol) and 1-hydroxy-7-azabenzotriazole (39 mg, 0.28 mmol) in DMF (2 mL) and dichloromethane (2 mL) was stirred at room temperature for 16 hours. The reaction mixture was loaded onto an ion exchange cartridge (SCX, 0.5 g), washed with methanol (2×1.5 mL), 0.1 N NH₃ in methanol (2×1.5 mL), and 2 M NH₃ in methanol. The concentrated ammonia fractions were collected and concentrated to give the crude product. This was further purified using chromatography (silica gel, 10% methanol/dichloromethane) to give the desired product (0.1 g).

D.

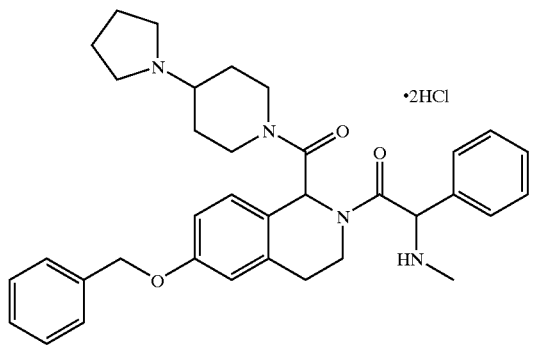

A solution of Part C compound (250 mg, 0.37 mmol) in 4 M HCl in dioxane (1 mL) was stirred at room temperature for 1 hour. The reaction mixture was concentrated to give the crude product (200 mg): HPLCb rt=2.45 and, 2.66 min; LC/MS (electrospray, +ions) m/z 567.5 (M+H).

EXAMPLES 506–528

The compounds shown in the table below were synthesized in library format starting with Part B compound from Example 505. Part B compound from Example 505 (500 μL of a 0.06 M solution in dichloromethane, 0.03 mmol), the appropriate acid (300 μL of a 0.15 M solution in dichloromethane, 0.045 mmol), 1-hydroxy-7-azabenzotriazole (0.045 mmol), and diisopropylcarbodiimide (0.045 mmol) in 200 μL DMF were stirred at room temperature for 16 hours. The reaction mixtures were loaded onto ion exchange cartridges (SCX, 0.5 g), washed with methanol (2×1.5 mL), 0.1 N NH₃ in methanol (2×1.5 mL), and 2 M NH₃ in methanol. The concentrated ammonia fractions were collected and concentrated to give the desired products which gave the analytical data shown.

= X₁-R₁

| Example No | X₁-R₁ | Calc MW | LC/MS (M + H)⁺ |
|---|---|---|---|
| 506 | (2-methylbenzoyl) | 537.7 | 538.71 |
| 507 | (2-phenylbutanoyl) | 565.8 | 566.77 |
| 508 | (4-trifluoromethylbenzoyl) | 591.7 | 592.7 |
| 509 | (pyridin-3-ylacetyl) | 538.7 | 539.73 |
| 510 | (4-(4-chlorobenzoyl)propanoyl) | 613.3 | 614.71 |

-continued
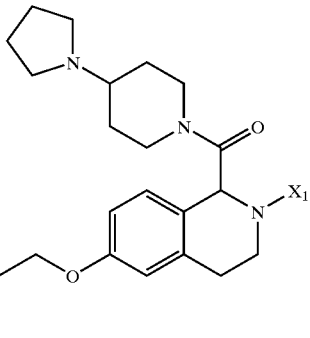
= X₁-R₁
| Example No | X₁-R₁ | Calc MW | LC/MS (M + H)⁺ |
|---|---|---|---|
| 511 | 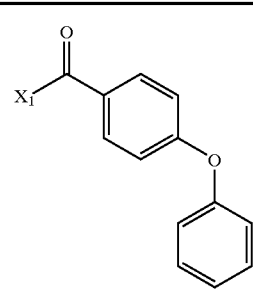 | 615.8 | 616.73 |
| 512 | 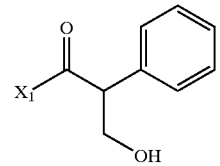 | 567.7 | 568.75 |
| 513 | 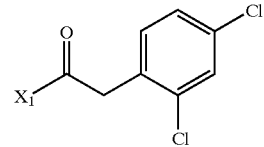 | 605.2 | 606.19 |
| 514 | 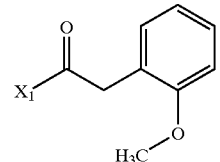 | 567.7 | 568.3 |
| 515 | 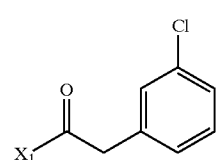 | 571.3 | 572.71 |
| 516 | 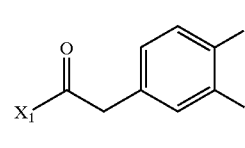 | 605.2 | 606.65 |
-continued
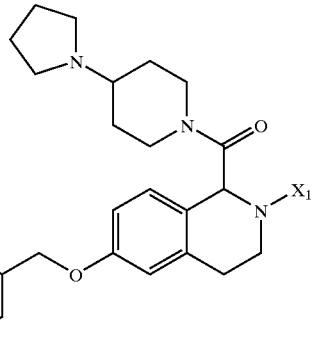
= X₁-R₁
| Example No | X₁-R₁ | Calc MW | LC/MS (M + H)⁺ |
|---|---|---|---|
| 517 | 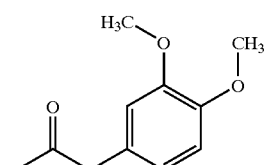 | 597.8 | 598.76 |
| 518 | 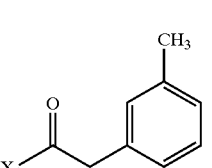 | 551.7 | 552.74 |
| 519 | 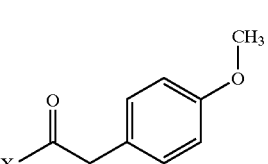 | 567.7 | 568.74 |
| 520 | 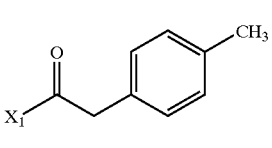 | 551.7 | 552.73 |
| 521 | 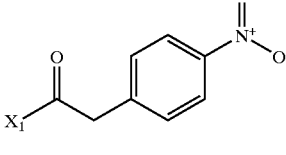 | 582.7 | 583.25 |
| 522 | 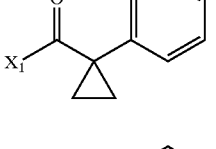 | 563.7 | 564.74 |
| 523 | 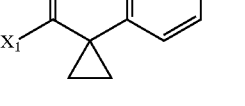 | 597.3 | 598.26 |

-continued

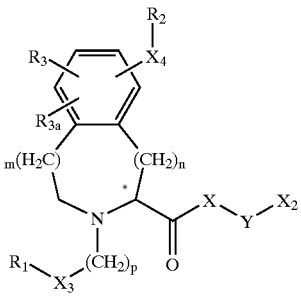

= $X_1$-$R_1$

| Example No | $X_1$-$R_1$ | Calc MW | LC/MS $(M + H)^+$ |
|---|---|---|---|
| 524 | | 605.7 | 606.25 |
| 525 | | 571.3 | 572.69 |
| 526 | | 643.8 | 644.79 |
| 527 | | 643.8 | 644.77 |
| 528 | | 565.8 | 566.31 |

We claim:

1. A method of treating chemokinereceptor-mediated disorders comprising administering to a patient in need thereof a therepeutically effective amount of at least one compound of formula I

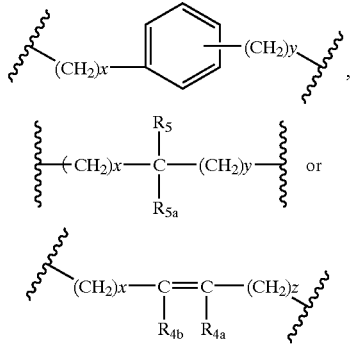

including enantiomers, diastereomers, and salts thereof, wherein $R_1$ is alkyl, aryl, alkenyl, alkynyl, arylalkyl, arylalkenyl, cycloalkyl, arylcycloalkyl cycloalkylalkyl, cycloalkylalkoxy, alkoxyalkyl, alkylthioalkyl, aryloxyalkyl, arylalkoxyalkyl, cycloheteroalkyl, cycloheteroalkylalkyl, heteroaryl, or heteroarylalkyl, and where these groups may be optionally substituted with 1 to 3 J1 groups which may be the same or different and the $R_1$ aryls may be further optionally substituted with 1 to 5 halogens, aryl, —$CF_3$, —$OCF_3$, 1–3 hydroxyls, 2 of which substituents where possible, may be joined by a methylene bridge;

$R_2$ is H, alkyl, aryl, alkenyl, alkynyl, arylalkyl, arylalkenyl, cycloalkyl, cycloalkylalkyl, alkoxyalkyl, aryloxyalkyl, arylalkoxyalkyl, cycloheteroalkyl, cycloheteroalkylalkyl, cycloalkylalkoxy, heteroaryl, or heteroarylalkyl, and where these groups may be optionally substituted with a J1a group and the aryls may be further optionally substituted with 1 to 5 halogens, —$CF_3$, —$OCF_3$, or 1–3 hydroxyls;

X is a bond, —O—, or —$NR_4$—;

$R_3$ and $R_{3a}$ are the same or different and are independently selected from H, alkoxy, halogen, —$CF_3$, alkyl, or aryl;

$R_4$, $R_{4a}$, $R_{4b}$, $R_{4c}$, $R_{4d}$, $R_{4e}$, $R_{4f}$, $R_{4g}$, $R_{4h}$, $R_{4i}$, $R_{4j}$, $R_{4k}$, and $R_{4l}$ are the same or different and are independently selected from H, $C_1$–$C_6$alkyl, or aryl;

m, n and p are the same or different and are independently 0 or 1;

Y is a bond,

![structures]

where x and y are the same or different and are independently 0 to 3 and z is 1 to 3;

$R_5$ and $R_{5a}$ are the same or different and are independently H, alkyl, alkoxy, hydroxyl, halogen, —$CF_3$, aryl, alkaryl, and cycloalkyl; or $R_5$ and $R_{5a}$ can be independently joined to one or both of $R_6$ and $R_7$ groups (see $X_2$) to form an alkylene bridge of 1 to 5 carbon atoms; or $R_5$ and $R_{5a}$ can be joined together to form a ring of from 4–7 carbon atoms;

X₂ is aryl optionally substituted with 1 to 3 J1 groups which may be the same or different, cycloheteroalkyl optionally substituted with 1 to 3 J1 groups which may be the same or different, pyridinyl optionally substituted with 1 to 3 J1 groups which may be the same or different,

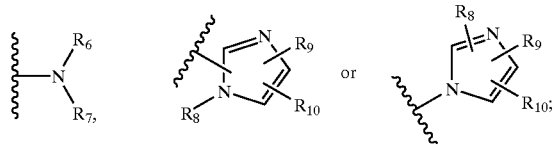

R₆ and R₇ are the same or different and are independently H or alkyl where the alkyl may be optionally substituted with halogen, 1 to 3 hydroxys, 1 to 3 C₁–C₁₀alkanoyloxy, 1 to 3 C₁–C₆ alkoxy, phenyl, phenoxy, or C₁–C₆alkoxycarbonyl; or R₆ and R₇ can together form —(CH₂)ₜX₅(CH₂)ᵤ— where X₅ is —C(R₄c)(R₄d)—, —C(R₄c)(NT₁T₁ₐ)—, —O— or —N(R₄ₑ)—, t and u are the same or different and are independently 0 to 4;

R₈ is H, C₁–C₆alkyl, —CF₃, alkaryl, or aryl, and with the alkyl and aryl groups being optionally substituted with 1 to 3 hydroxys, 1 to 3 C₁–C₁₀alkanoyloxy, 1 to 3 C₁–C₆ alkoxy, phenyl, phenoxy or C₁–C₆alkoxycarbonyl;

R₉ and R₁₀ are the same or different and are independently H, C₁–C₆alkyl, —CF₃, alkaryl, aryl, or halogen, and with the alkyl and aryl groups being optionally substituted with 1 to 3 hydroxys, 1 to 3 C₁–C₁₀ alkanoyloxy, 1 to 3 C₁₋₆ alkoxy, phenyl, phenoxy or C₁–C₆ alkoxycarbonyl;

X₃ is a bond, —C(O)—, —C(O)O—, —C(O)N(R₄f)—, —S(O)₂—, or —S(O)₂N(R₄f)—;

X₄ is a bond, —O—, —OC(O)—, —N(R₄g)—, —N(R₄g)C(O)—, —N (R₄g)C(O)N(R₄h)—, —N(R₄g)S(O)₂—, —N(R₄g)S(O)₂N(R₄h), —OC(O)N(R₄g)—, —C(O)—, —C(O)N(R₄g)—, —S—, —S(O)₂—, or —S(O)₂N(R₄g)—;

J1 and J1a are the same or different and are independently nitro, halogen, hydroxyl, —OCF₃, —CF₃, alkyl, aryl, —(CH₂)ᵥ CN, —(CH₂)ᵥN(T₁ₐ)C(O)T₁, —(CH₂)ᵥN(T₁ₐ)C(O)OT₁, —(CH₂)ᵥN(T₁ₐ)C(O)N(T₁ₐ)T₁, —(CH₂)ᵥNT₁(T₁ₐ), —(CH₂)ᵥN(T₁ₐ)SO₂T₁, —(CH₂)ᵥC(O)N(T₁)T₁, —(CH₂)ᵥC(O)OT₁, —(CH₂)ᵥOC(O)OT₁, —(CH₂)ᵥOC(O)T₁, —(CH₂)ᵥOC(O)OT₁, —(CH₂)ᵥOC(O)T₁, —(CH₂)ᵥOC(O)N(T₁ₐ)T₁, —(CH₂)ᵥN(T₁ₐ)SO₂N(T₁ᵦ)T₁, —(CH₂)ᵥOT₁, —(CH₂)ᵥSO₂T₁, —(CH₂)ᵥSO₂N(T₁ₐ)T₁, —(CH₂)ᵥC(O)T₁, —(CH₂)ᵥCH(OH)T₁, or heteroaryl as defined below, with v being 0–3;

T₁, T₁ₐ and T₁ᵦ are the same or different and are independently H, alkyl, alkenyl, alkynyl, lower alkythioalkyl, alkoxyalkyl, aryl, arylalkyl, heteroaryl, heteroarylalkyl, cycloheteroalkyl, or cycloalkyl, each of which may be optionally substituted with halogen, hydroxyl, —C(O)NR₄ᵢR₄ⱼ, —NR₄ᵢC(O)R₄ⱼ, —CN, —N(R₄ᵢ)SO₂R₁₁, —OC(O)R₄ᵢ, —SO₂ NR₄ᵢR₄ⱼ, —SOR₁₁, —SO₂R₁₁, alkoxy, —COOH, cycloheteroalkyl, or —C(O)OR₁₁; with the proviso that T₁ cannot be hydrogen when it is connected to sulfur, as in SO₂T₁; or T₁ and T₁ₐ or T₁ and T₁ᵦ can together form —(CH₂)ᵣX₅ₐ(CH₂)ₛ— where X₅ₐ is —C(R₄k)(R₄l)—, —C(R₄k)(NT₁T₁ₐ)—, —O— or —N(R₄k)—, r and s are the same or different and are independently 0 to 4;

R₁₁ is C₁–C₆alkyl or aryl; with the proviso that
(1) where m is 0 and n is 1, the moiety —X₄—R₂ is other than alkyl or alkoxy; and
(2) where X is a bond and X₂ is amino, then m is 1.

2. The method of claim 1 wherein the chemokine receptor-mediated disorder is selected from asthma, COPD, allergic disease, allergic rhinitis, rheumatoid arthritis, atherosclerosis, psoriasis, solid organ transplant rejection, osteoarthritis and inflammatory bowel syndrome.

3. The method of claim 1 wherein the compound of formula I has the structure

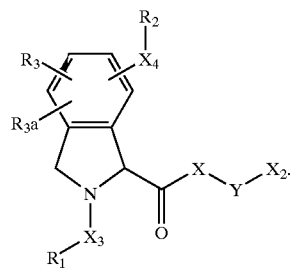

4. The method of claim 1 wherein the compound of formula I has the structure

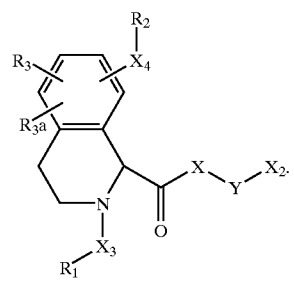

5. The method of claim 1 wherein the compound of formula I has the structure

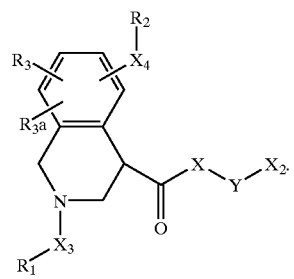

6. The method of claim 1 wherein the compound of formula I has the structure

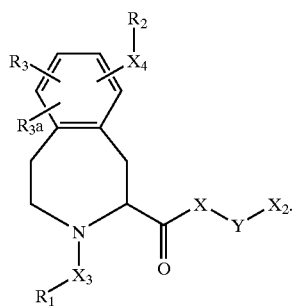

7. A compound of formula I

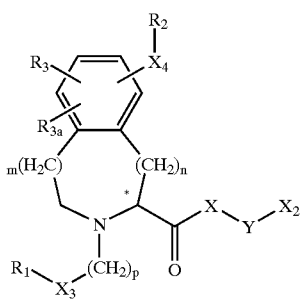

including enantiomers, diastereomers, and salts thereof, wherein $R_1$ is alkyl, aryl, alkenyl, alkynyl, arylalkyl, arylalkenyl, cycloalkyl, arylcycloalkyl cycloalkylalkyl, cycloalkylalkoxy, alkoxyalkyl, alkylthioalkyl, aryloxyalkyl, arylalkoxyalkyl, cycloheteroalkyl, cycloheteroalkylalkyl, heteroaryl, or heteroarylalkyl, and where these groups may be optionally substituted with 1 to 3 J1 groups which may be the same or different and the $R_1$ aryls may be further optionally substituted with 1 to 5 halogens, aryl, —$CF_3$, —$OCF_3$, 1–3 hydroxyls, 2 of which substituents where possible, may be joined by a methylene bridge;

$R_2$ is H, alkyl, aryl, alkenyl, alkynyl, arylalkyl, arylalkenyl, cycloalkyl, cycloalkylalkyl, alkoxyalkyl, aryloxyalkyl, arylalkoxyalkyl, cycloheteroalkyl, cycloheteroalkylalkyl, cycloalkylalkoxy, heteroaryl, or heteroarylalkyl, and where these groups may be optionally substituted with a J1a group and the aryls may be further optionally substituted with 1 to 5 halogens, —$CF_3$, —$OCF_3$, or 1–3 hydroxyls;

X is a bond, —O—, or —$NR_4$—;

$R_3$ and $R_{3a}$ are the same or different and are independently selected from H, alkoxy, halogen, —$CF_3$, alkyl, or aryl;

$R_4$, $R_{4a}$, $R_{4b}$, $R_{4c}$, $R_{4d}$, $R_{4e}$, $R_{4f}$, $R_{4g}$, $R_{4h}$, $R_{4i}$, $R_{4j}$, $R_{4k}$, and $R_{4l}$ are the same or different and are independently selected from H, $C_1$–$C_6$alkyl, or aryl;

m, n and p are the same or different and are independently 0 or 1;

Y is a bond,

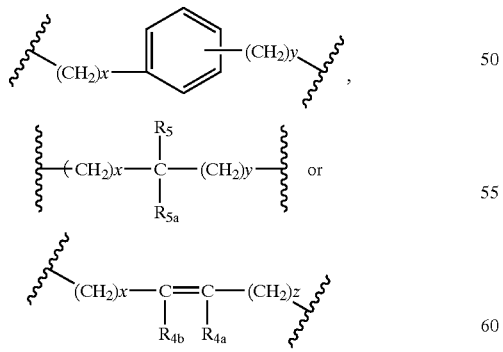

where x and y are the same or different and are independently 0 to 3 and z is 1 to 3;

$R_5$ and $R_{5a}$ are the same or different and are independently H, alkyl, alkoxy, hydroxyl, halogen, —$CF_3$, aryl, alkaryl, and cycloalkyl; or $R_5$ and $R_{5a}$ can be independently joined to one or both of $R_6$ and $R_7$ groups (see $X_2$) to form an alkylene bridge of 1 to 5 carbon atoms; or $R_5$ and $R_{5a}$ can be joined together to form a ring of from 4–7 carbon atoms;

$X_2$ is aryl optionally substituted with 1 to 3 J1 groups which may be the same or different, cycloheteroalkyl optionally substituted with 1 to 3 J1 groups which may be the same or different, or pyridinyl optionally substituted with 1 to 3 J1 groups which may be the same or different;

$R_6$ and $R_7$ are the same or different and are independently H or alkyl where the alkyl may be optionally substituted with halogen, 1 to 3 hydroxys, 1 to 3 $C_1$–$C_{10}$alkanoyloxy, 1 to 3 $C_1$–$C_6$ alkoxy, phenyl, phenoxy, or $C_{1–6}$alkoxycarbonyl; or $R_6$ and $R_7$ can together form —$(CH_2)_tX_5(CH_2)_u$— where $X_5$ is —$C(R_{4c})(R_{4d})$—, —$C(R_{4c})(NT_1T_{1a})$—, —O— or —$N(R_{4e})$—, t and u are the same or different and are independently 0 to 4;

$R_8$ is H, $C_1$–$C_6$alkyl, —$CF_3$, alkaryl, or aryl, and with the alkyl and aryl groups being optionally substituted with 1 to 3 hydroxys, 1 to 3 $C_1$–$C_{10}$alkanoyloxy, 1 to 3 $C_1$–$C_6$ alkoxy, phenyl, phenoxy or $C_1$–$C_6$alkoxycarbonyl;

$R_9$ and $R_{10}$ are the same or different and are independently H, $C_1$–$C_6$alkyl, —$CF_3$, alkaryl, aryl, or halogen, and with the alkyl and aryl groups being optionally substituted with 1 to 3 hydroxys, 1 to 3 $C_1$–$C_{10}$ alkanoyloxy, 1 to 3 $C_{1–6}$ alkoxy, phenyl, phenoxy or $C_1$–$C_6$ alkoxycarbonyl;

$X_3$ is a bond, —C(O)—, —C(O)O—, —C(O)N($R_{4f}$)—, —$S(O)_2$—, or —$S(O)_2N(R_{4f})$—;

$X_4$ is a bond, —O—, —OC(O)—, —N($R_{4g}$)—, —N($R_{4g}$)C(O)—, —N($R_{4g}$)C(O)$_vN(R_{4h})$—, —N($R_{4g}$)S(O)$_2$—, —N($R_{4g}$)S(O)$_2N(R_{4h})$, —OC(O)N($R_{4g}$)—, —C(O)—, —C(O)N($R_{4g}$)—, —S—, —S(O)$_2$—, or —$S(O)_2N(R_{4g})$—;

J1 and J1a are the same or different and are independently nitro, halogen, hydroxyl, —$OCF_3$, —$CF_3$, alkyl, aryl, —$(CH_2)_vCN$, —$(CH_2)_vN(T_{1a})C(O)T_1$, —$(CH_2)_vN(T_{1a})C(O)OT_1$, —$(CH_2)_vN(T_{1a})C(O)N(T_{1a})T_1$, —$(CH_2)_vNT_1(T_{1a})$, —$(CH_2)_vN(T_{1a})SO_2T_1$, —$(CH_2)C(O)N(T_{1a})T_1$, —$(CH_2)_vC(O)OT_1$, —$(CH_2)_vOC(O)OT_1$, —$(CH_2)_vOC(O)T_1$, —$(CH_2)_vOC(O)OT_1$, —$(CH_2)_vOC(O)T_1$, —$(CH_2)_vOC(O)N(T_{1a})T_1$, —$(CH_2)_vN(T_{1a})SO_2N(T_{1b})T_1$, —$(CH_2)_vOT_1$, —$(CH_2)_vSO_2T_1$, —$(CH_2)_vSO_2N(T_{1a})T_1$, —$(CH_2)_vC(O)T_1$, —$(CH_2)_vCH(OH)T_1$, or heteroaryl as defined below, with v being 0–3;

$T_1$, $T_{1a}$ and $T_{1b}$ are the same or different and are independently H, alkyl, alkenyl, alkynyl, lower alkythioalkyl, alkoxyalkyl, aryl, arylalkyl, heteroaryl, heteroarylalkyl, cycloheteroalkyl, or cycloalkyl, each of which may be optionally substituted with halogen, hydroxyl, —$C(O)NR_{4i}R_{4j}$, —$NR_{4i}C(O)R_{4j}$, —CN, —$N(R_{4i})SO_2R_{11}$, —$OC(O)R_{4i}$, —$SO_2NR_{4i}R_{4j}$, —$SOR_{11}$, —$SO_2R_{11}$, alkoxy, —COOH, cycloheteroalkyl, or —$C(O)OR_{11}$; with the proviso that $T_1$ cannot be hydrogen when it is connected to sulfur, as in $SO_2T_1$; or $T_1$ and $T_{1a}$ or $T_1$ and $T_{1b}$ can together form —$(CH_2)_rX_{5a}(CH_2)_s$— where $X_{5a}$ is —$C(R_{4k})(R_{4l})$—, —$C(R_{4k})(NT_1T_{1a})$—, —O— or —$N(R_{4k})$—, r and s are the same or different and are independently 0 to 4;

$R_{11}$ is $C_1$–$C_6$alkyl or aryl; with the proviso that (1) where m is 0 and n is 1, the moiety —$X_4$—$R_2$ is other than alkyl or alkoxy; and (2) where X is a bond and $X_2$ is amino, then m is 1.

8. A compound of claim 7 having the structure
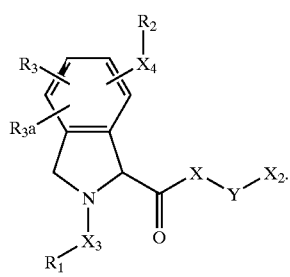
9. A compound of claim 7 having the structure
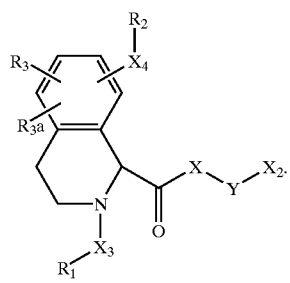
10. A compound of claim 7 having the structure
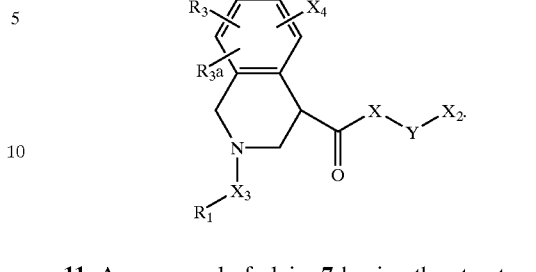
11. A compound of claim 7 having the structure
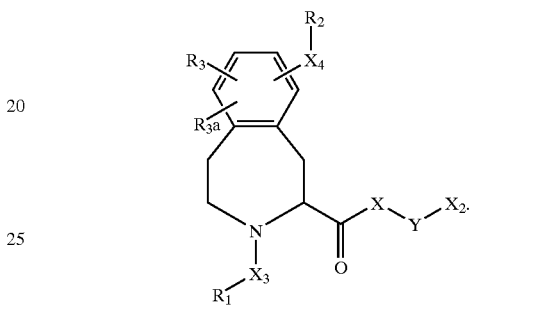
12. A pharmaceutical composition comprising at least one compound of claim 7 and a pharmaceutically acceptable vehicle or carrier therefor.
* * * * *